United States Patent  (10) Patent No.: US 12,376,918 B2
DeFonzo et al.  (45) Date of Patent: Aug. 5, 2025

(54) SYSTEMS AND TECHNIQUES FOR PROVIDING MULTIPLE PERSPECTIVES DURING MEDICAL PROCEDURES

(71) Applicant: Auris Health, Inc., Redwood City, CA (US)

(72) Inventors: Joshua F. DeFonzo, San Carlos, CA (US); Andrew F. O'Rourke, Los Angeles, CA (US); Travis Michael Schuh, Los Altos, CA (US); Yanan Huang, Sunnyvale, CA (US); Jason Tomas Wilson, Redwood City, CA (US)

(73) Assignee: Auris Health, Inc., Redwood City, CA (US)

( * ) Notice: Subject to any disclaimer, the term of this patent is extended or adjusted under 35 U.S.C. 154(b) by 1424 days.

(21) Appl. No.: 16/848,721

(22) Filed: Apr. 14, 2020

(65) Prior Publication Data

US 2020/0237458 A1 Jul. 30, 2020

Related U.S. Application Data

(63) Continuation of application No. 16/386,098, filed on Apr. 16, 2019, now Pat. No. 10,667,875.

(Continued)

(51) Int. Cl.
*A61B 34/00* (2016.01)
*A61B 34/30* (2016.01)
*A61B 90/00* (2016.01)

(52) U.S. Cl.
CPC .............. *A61B 34/30* (2016.02); *A61B 34/25* (2016.02); *A61B 34/70* (2016.02); *A61B 90/361* (2016.02);

(Continued)

(58) Field of Classification Search
CPC ......... A61B 34/30; A61B 34/25; A61B 34/70; A61B 90/361; A61B 90/37;

(Continued)

(56) References Cited

U.S. PATENT DOCUMENTS 5,199,417 A  4/1993  Muller et al.
5,876,325 A  3/1999  Mizuno et al.
(Continued)

FOREIGN PATENT DOCUMENTS

WO  WO 17/048194  3/2017

OTHER PUBLICATIONS

Darwiche, 2015, Operative technique and early experience for robotic assisted laparoscopic nephroureterectomy (RALNU) using da Vinci Xi, SpringerPlus, 4:298.

(Continued)

*Primary Examiner* — Anh Tuan T Nguyen
*Assistant Examiner* — Rynae E Boler
(74) *Attorney, Agent, or Firm* — Frost Brown Todd LLP

(57) ABSTRACT

Provided are systems and techniques for providing multiple perspectives during medical procedures. In one aspect, a method includes positioning a plurality of cannulas in a plurality of anatomical quadrants of a patient, inserting first and second surgical tools coupled to corresponding robotic arms into the respective cannulas. The method may include inserting an articulatable camera coupled to another robotic arm into another of the cannulas, where the articulatable camera is capable of showing a first view including the first surgical tool in a first anatomical quadrant and articulating to show a second view including the second surgical tool in a second anatomical quadrant. The method may further involve performing a surgical procedure in at least one of the first anatomical quadrant or the second anatomical quadrant.

19 Claims, 56 Drawing Sheets

Related U.S. Application Data

(60) Provisional application No. 62/690,868, filed on Jun. 27, 2018.

(52) U.S. Cl.
CPC ......... *A61B 2034/302* (2016.02); *A61B 90/37* (2016.02)

(58) Field of Classification Search
CPC ...... A61B 2034/302; A61B 2034/2065; A61B 17/3421; A61B 34/74; A61B 5/743
See application file for complete search history.

(56) References Cited

U.S. PATENT DOCUMENTS

| | | | |
|---|---|---|---|
| 8,021,326 B2 | 9/2011 | Moll et al. |
| 8,652,030 B2 | 2/2014 | Matsuura et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,668,768 B2 | 6/2017 | Piron et al. |
| 9,713,509 B2 | 7/2017 | Schuh et al. |
| 9,717,563 B2 | 8/2017 | Tognaccini |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,667,875 B2 | 6/2020 | DeFonzo |
| 2002/0082612 A1 | 6/2002 | Moll et al. |
| 2003/0181809 A1 | 9/2003 | Hall et al. |
| 2006/0178556 A1 | 8/2006 | Hasser et al. |
| 2008/0147089 A1 | 6/2008 | Loh |
| 2009/0005768 A1 | 1/2009 | Sharareh |
| 2009/0048611 A1 | 2/2009 | Funda |
| 2009/0326318 A1 | 12/2009 | Tognaccini |
| 2009/0326322 A1* | 12/2009 | Diolaiti ................. A61B 34/30 600/112 |
| 2010/0100045 A1 | 4/2010 | Pravongviengkham et al. |
| 2010/0234857 A1 | 9/2010 | Itkowitz |
| 2011/0277775 A1 | 11/2011 | Holop et al. |
| 2012/0283747 A1* | 11/2012 | Popovic ................. A61B 34/30 606/130 |
| 2012/0302869 A1 | 11/2012 | Koyrakh |
| 2014/0051049 A1 | 2/2014 | Jarc |
| 2014/0142591 A1 | 5/2014 | Alvarez et al. |
| 2014/0243801 A1 | 8/2014 | Fanelli et al. |
| 2014/0357984 A1 | 12/2014 | Wallace et al. |
| 2014/0364870 A1 | 12/2014 | Alvarez et al. |
| 2015/0025549 A1 | 1/2015 | Kilroy et al. |
| 2015/0045675 A1 | 2/2015 | Chernomorsky |
| 2015/0073265 A1* | 3/2015 | Popovic ................. A61B 5/066 600/424 |
| 2015/0297299 A1 | 10/2015 | Yeung |
| 2016/0001038 A1 | 1/2016 | Romo et al. |
| 2016/0270865 A1 | 9/2016 | Landey et al. |
| 2016/0287279 A1 | 10/2016 | Bovay et al. |
| 2017/0007337 A1 | 1/2017 | Dan |
| 2017/0071456 A1* | 3/2017 | Ratnakar ................. A61B 1/126 |
| 2017/0143442 A1 | 5/2017 | Tesar |
| 2017/0189118 A1 | 7/2017 | Chopra |
| 2017/0189131 A1 | 7/2017 | Weir |
| 2017/0202627 A1 | 7/2017 | Sramek et al. |
| 2017/0209073 A1 | 7/2017 | Sramek et al. |
| 2017/0290631 A1 | 10/2017 | Lee et al. |
| 2018/0025666 A1 | 1/2018 | Ho et al. |
| 2018/0098817 A1* | 4/2018 | Nichogi ................. A61B 34/37 |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0338799 A1 | 11/2018 | Hladio et al. |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0110839 A1 | 4/2019 | Rafii-Tari et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |

(56) References Cited

U.S. PATENT DOCUMENTS

| | | |
|---|---|---|
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |

OTHER PUBLICATIONS

Sasaki, 2017, Laparoscopic hemicolectomy for a patient with situs inversus totalis: A case report, Int. J. Surg. Case Rep. 41:93-96.
International search report and written opinion dated Jul. 5, 2019 for PCT/US2019/27718.

* cited by examiner

SYSTEMS AND TECHNIQUES FOR PROVIDING MULTIPLE PERSPECTIVES DURING MEDICAL PROCEDURES

CROSS-REFERENCE TO RELATED APPLICATION(S)

This application is a continuation of U.S. application Ser. No. 16/386,098, filed Apr. 16, 2019, issued as U.S. Pat. No. 10,667,875 on Jun. 2, 2020, which claims the benefit of U.S. Provisional Application No. 62/690,868, filed Jun. 27, 2018, each of which is hereby incorporated by reference in its entirety.

TECHNICAL FIELD

The systems and methods disclosed herein are directed to medical procedures, and more particularly to systems and techniques which can provide multiple perspectives of an anatomical region during a medical procedure.

BACKGROUND

Certain medical procedures may be performed in multiple regions of a patient. For example, a patient's abdomen may be divided into four regions or quadrants. These quadrants may include a left lower quadrant (LLQ), a left upper quadrant (LUQ), a right upper quadrant (RUQ), and a right lower quadrant (RLQ). To perform a minimally invasive procedure in the abdomen, a plurality of cannulas may be placed into the patient through one or more incisions or access points, allowing medical tools access to multiple quadrants. The medical tools may include one or more surgical tools (e.g., a grasper or scissors) and an optical camera to provide a view of the internal anatomical space and the surgical tools.

SUMMARY

The systems, methods and devices of this disclosure each have several innovative aspects, no single one of which is solely responsible for the desirable attributes disclosed herein.

In one aspect, there is provided a surgical method comprising positioning a plurality of cannulas in a plurality of anatomical quadrants of a patient, wherein a first of the plurality of cannulas is positioned in a first anatomical quadrant and a second of the plurality of cannulas is positioned in a second anatomical quadrant, wherein each of the plurality of cannulas is capable of receiving therein at least one of a surgical tool or an articulatable camera; inserting a first surgical tool coupled to a first of a plurality of robotic arms into the first of the plurality of cannulas in the first anatomical quadrant; inserting a second surgical tool coupled to a second of the plurality of robotic arms into the second of the plurality of cannulas in the second anatomical quadrant; inserting an articulatable camera coupled to a third of the plurality of robotic arms into a third of the plurality of cannulas, wherein the articulatable camera is capable of showing a first view including the first surgical tool in the first anatomical quadrant and articulating to show a second view including the second surgical tool in the second anatomical quadrant; and performing a surgical procedure in at least one of the first anatomical quadrant or the second anatomical quadrant.

In another aspect, there is provided a system comprising a first robotic arm configured to be coupled to a first cannula positioned in a first anatomical location of a patient and drive an articulatable camera, the articulatable camera configured to be driven in a first number of degrees-of-freedom (DoF); a second robotic arm configured to be coupled to a second cannula positioned in a second anatomical location of the patient and drive a first tool; a user input device configured to be manipulated by a user in a second number of DoFs; one or more processors; and memory storing computer-executable instructions to cause the one or more processors to: receive an image from the articulatable camera including a view of a target site in the patient, receive, via the user input device, a user command to drive the articulatable camera, and determine instructions to robotically drive the articulatable camera via the first robotic arm based on the user command, wherein at least one of the DoFs of the user input device is constrained so as to maintain orientation alignment between the first tool and the user input device.

In yet another aspect, there is provided a surgical method comprising positioning a plurality of cannulas in a plurality of anatomical quadrants of a patient, wherein each of the plurality of cannulas is capable of receiving therein at least one of a surgical tool or a camera; inserting a camera coupled to a first one of a plurality of robotic arms into a first of the plurality of cannulas positioned in a first quadrant, the camera being configured to generate an image including a first view; detaching the camera from the first robotic arm; attaching the camera to a second one of the plurality of robotic arms; inserting the camera coupled to the second one of the plurality of robotic arms into a second of the plurality of cannulas positioned in a second quadrant; and setting a view of the camera via movement of the second robotic arm to obtain a second view, wherein the first robotic arm is docked to the first of the plurality of cannulas in the first quadrant, and wherein the second robotic arm is docked to the second of the plurality of cannulas in the second quadrant.

In still yet another aspect, there is provided a surgical method comprising positioning a plurality of cannulas in a plurality of anatomical quadrants of a patient, wherein each of the plurality of cannulas is capable of receiving therein at least one of a surgical tool or a camera; docking a first tool to a first of the plurality of cannulas, wherein the first tool is coupled to a first of a plurality of robotic arms; docking a second tool to a second of the plurality of cannulas, wherein the second tool is coupled to a second of the plurality of robotic arms; docking a camera to a third of the plurality of cannulas; and undocking the camera from the third of the plurality of cannulas and transferring the camera such that the camera can be docked to a fourth of the plurality of cannulas, wherein the first tool is capable of remaining docked to the first of the plurality of cannulas and the second tool is capable of remaining docked to the second of the plurality of cannulas while undocking the camera from the third of the plurality of cannulas and transferring the camera to the fourth of the plurality of cannulas.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
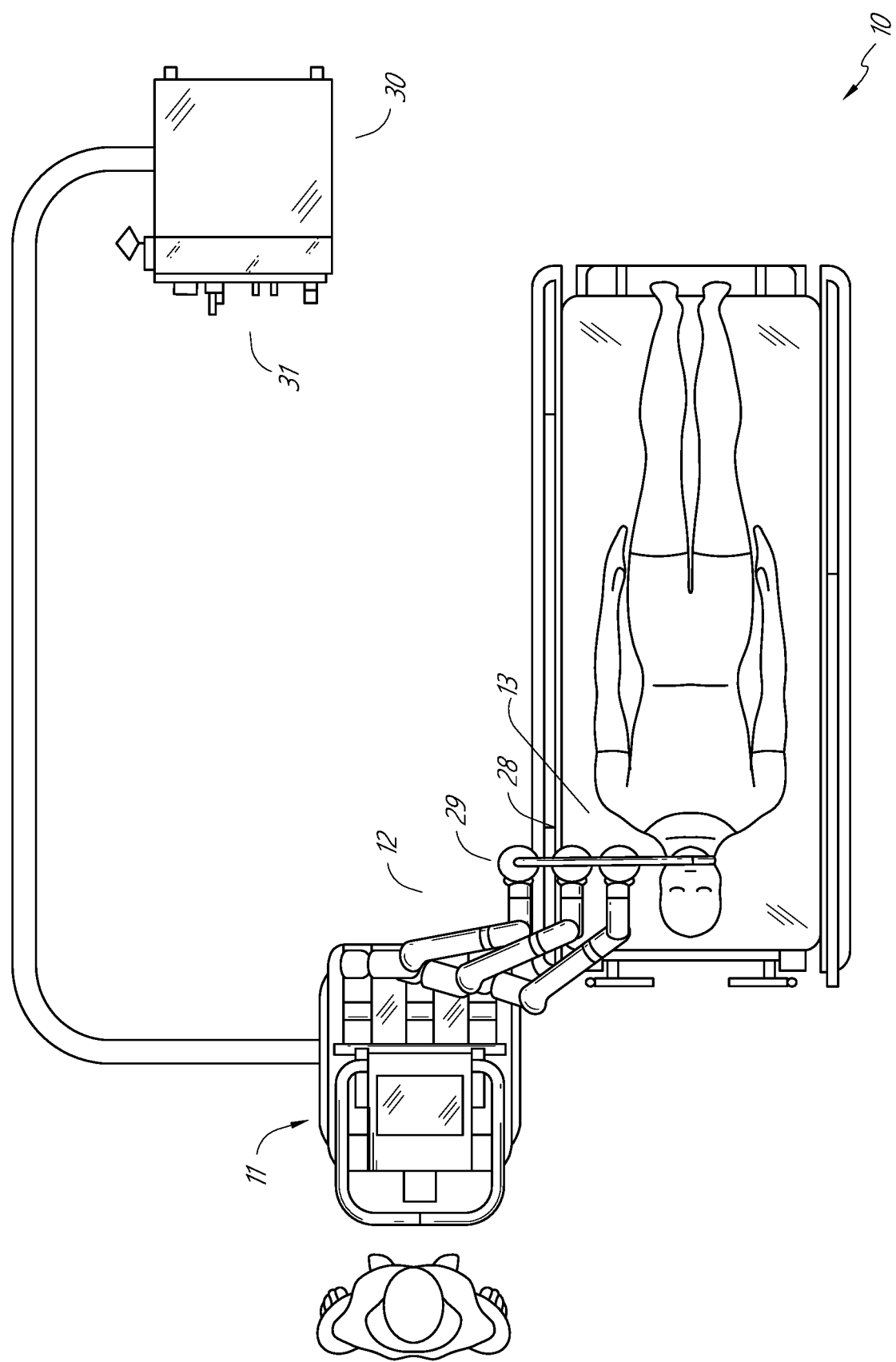
FIG. 1 illustrates an embodiment of a cart-based robotic system arranged for diagnostic and/or therapeutic bronchoscopy procedure(s).
Figure 2:
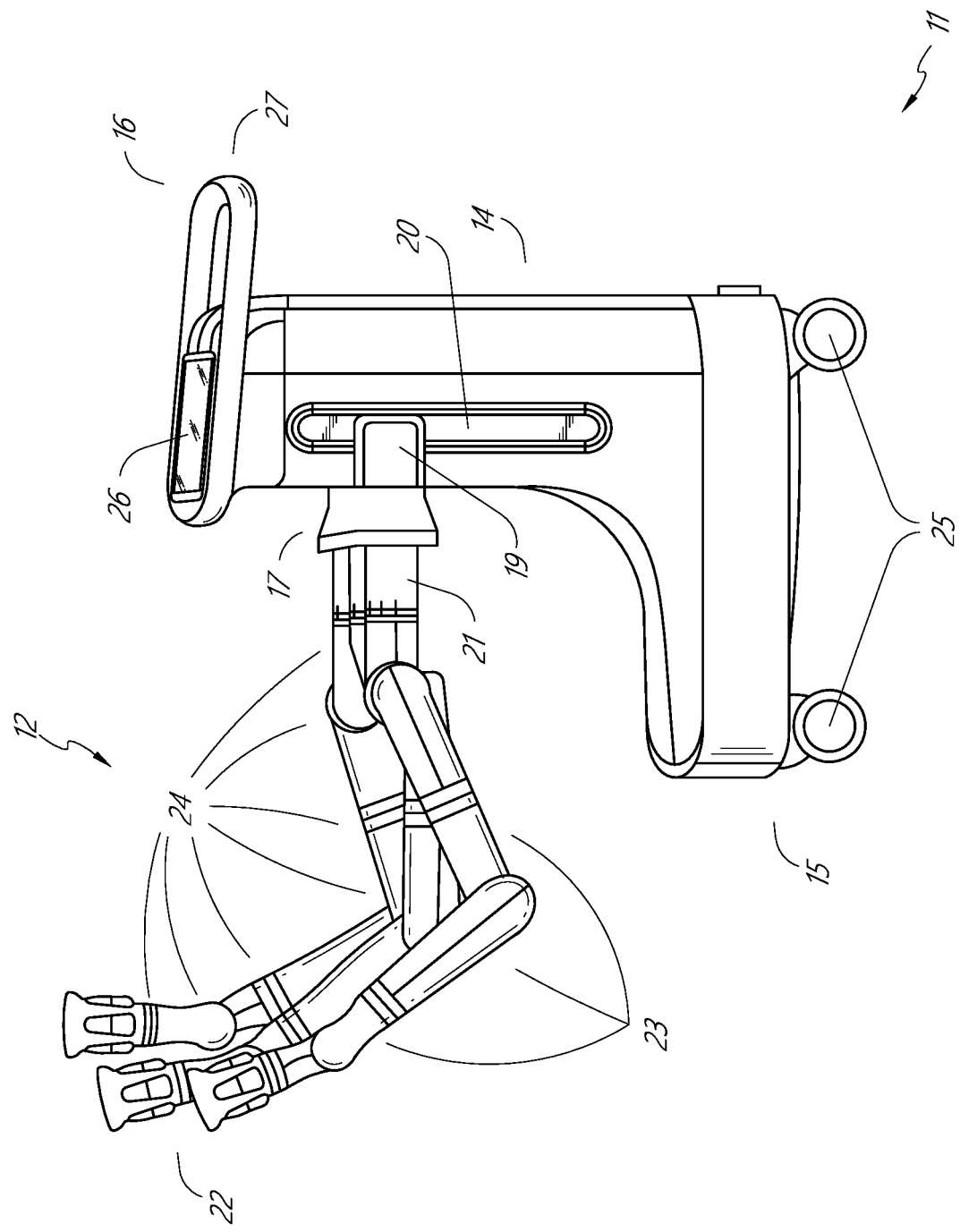
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees-of-freedom (DoF). A multitude of joints result in a multitude of DoF, allowing for "redundant" DoF. Redundant DoF allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
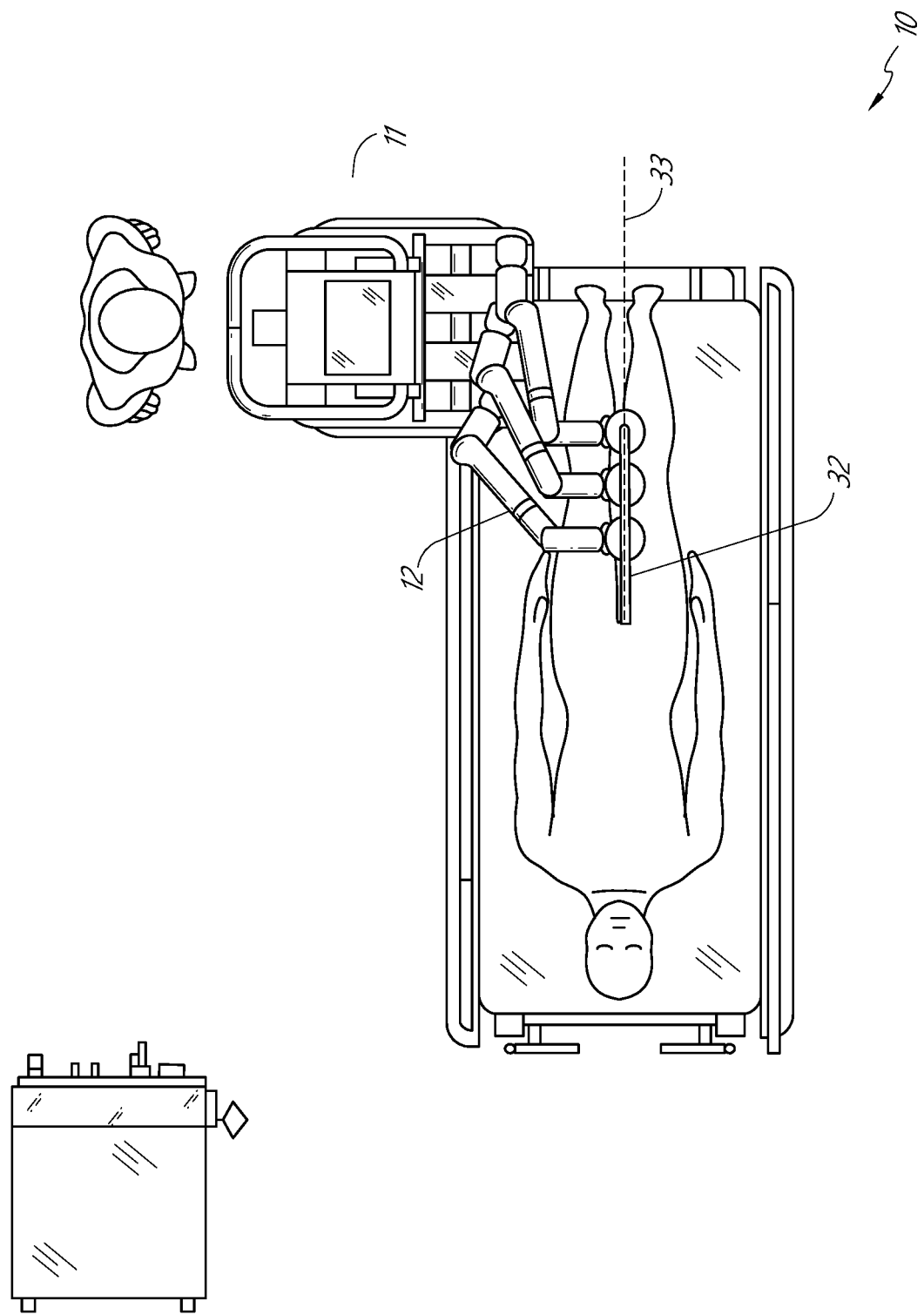
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
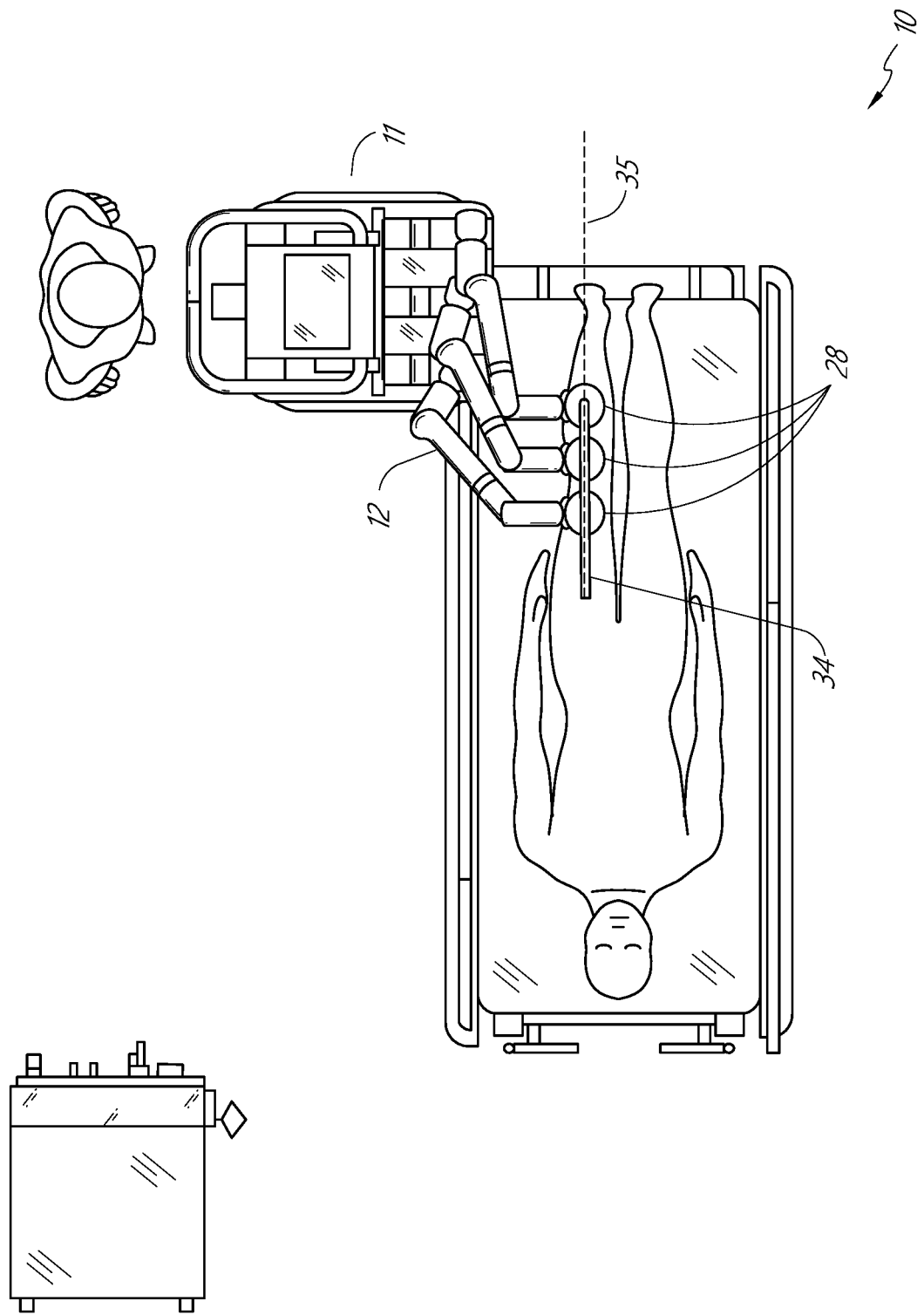
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
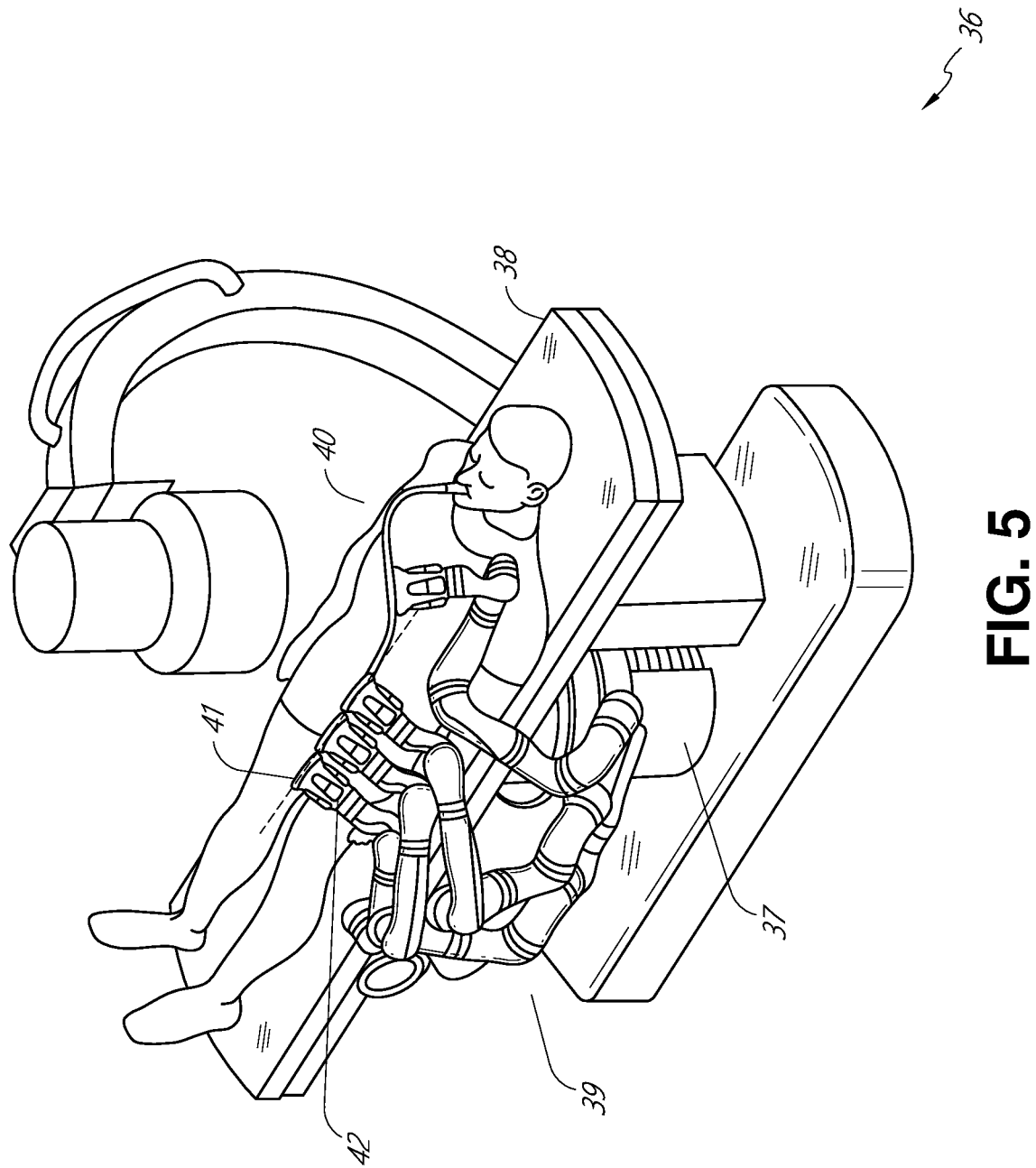
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
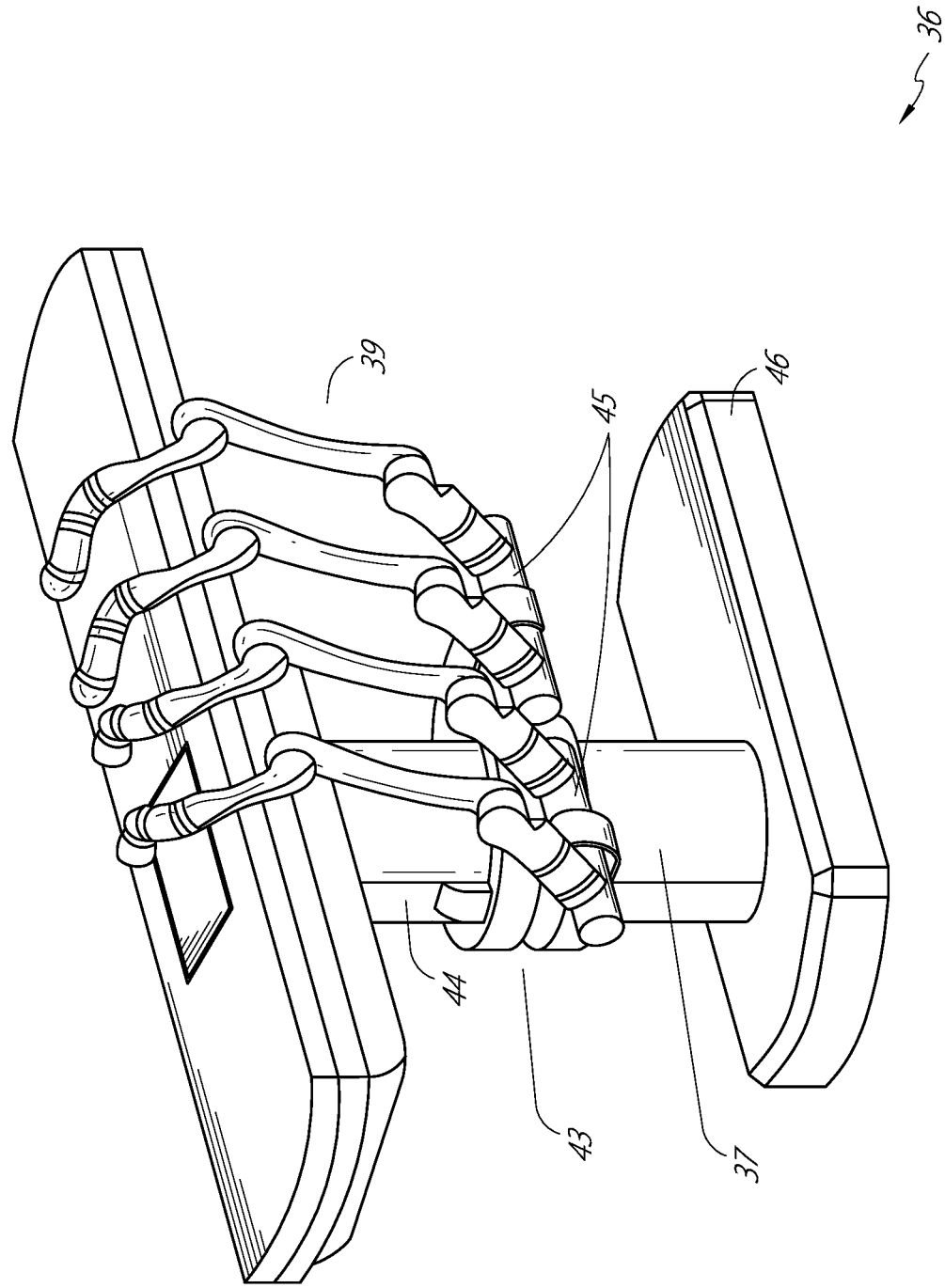
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
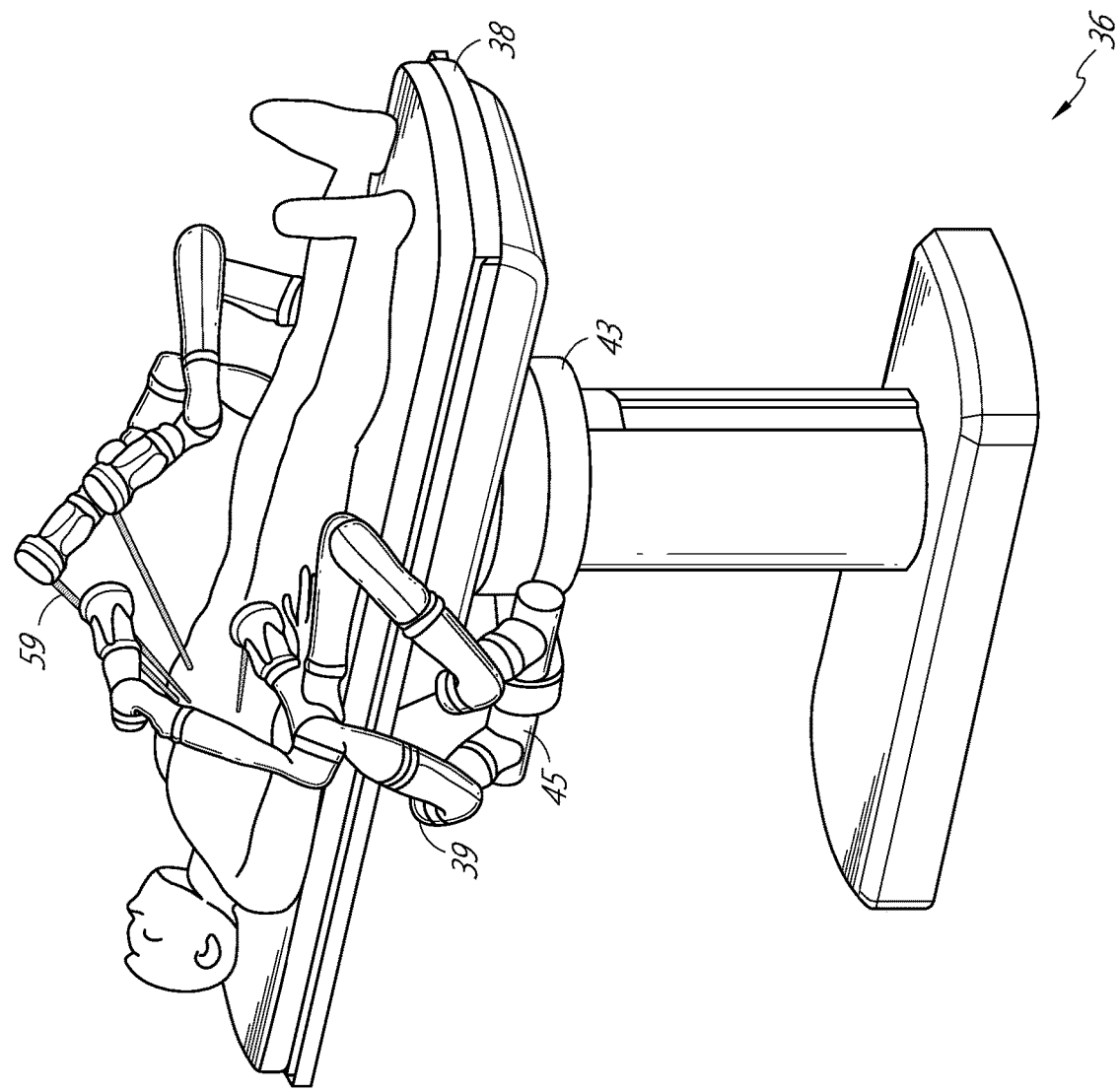
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
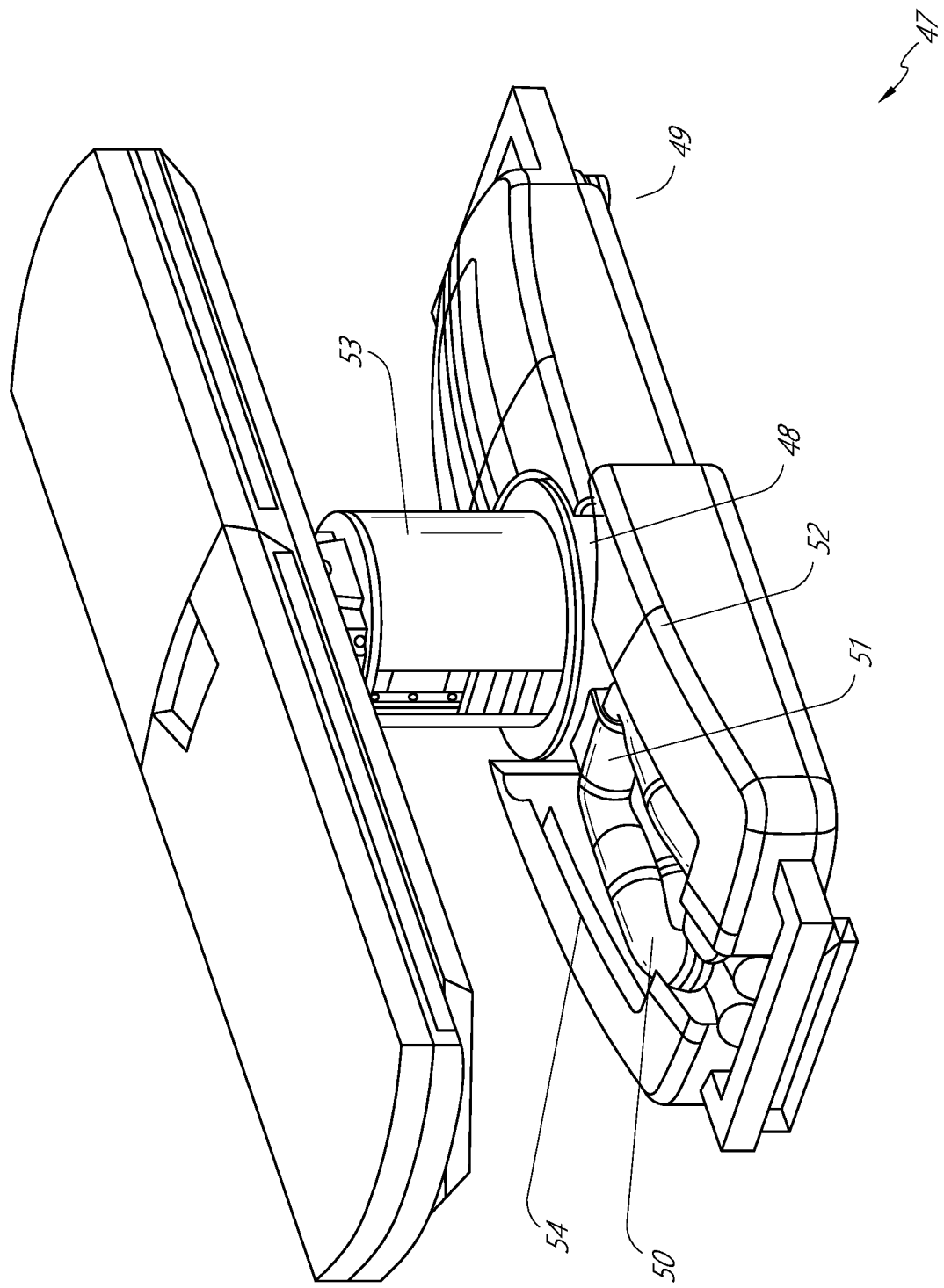
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
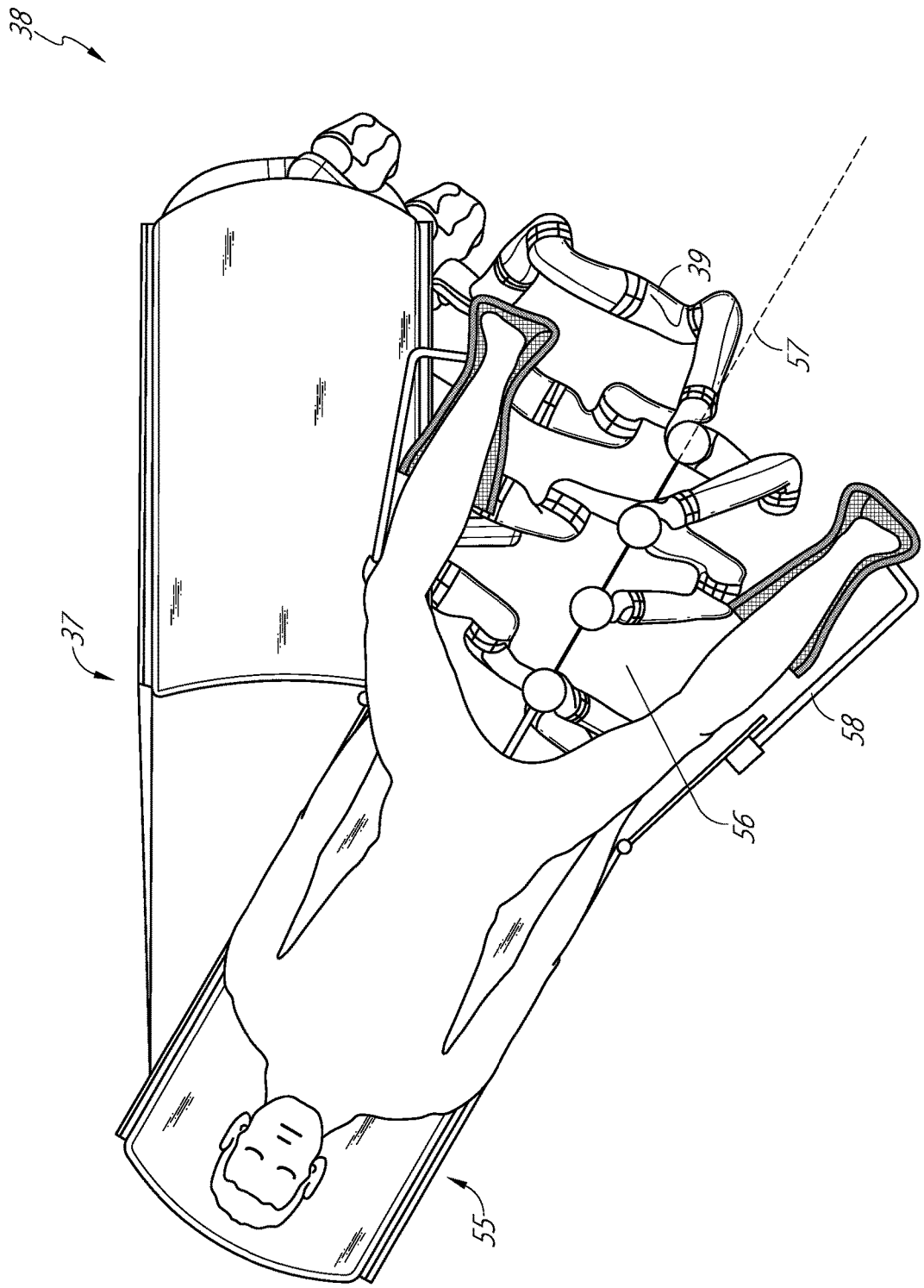
FIG. 8 illustrates an embodiment of a table-based robotic system configured for a ureteroscopy procedure.

FIG. 8 illustrates an embodiment of a robotically-enabled table-based system configured for a ureteroscopic procedure. During ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. During ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
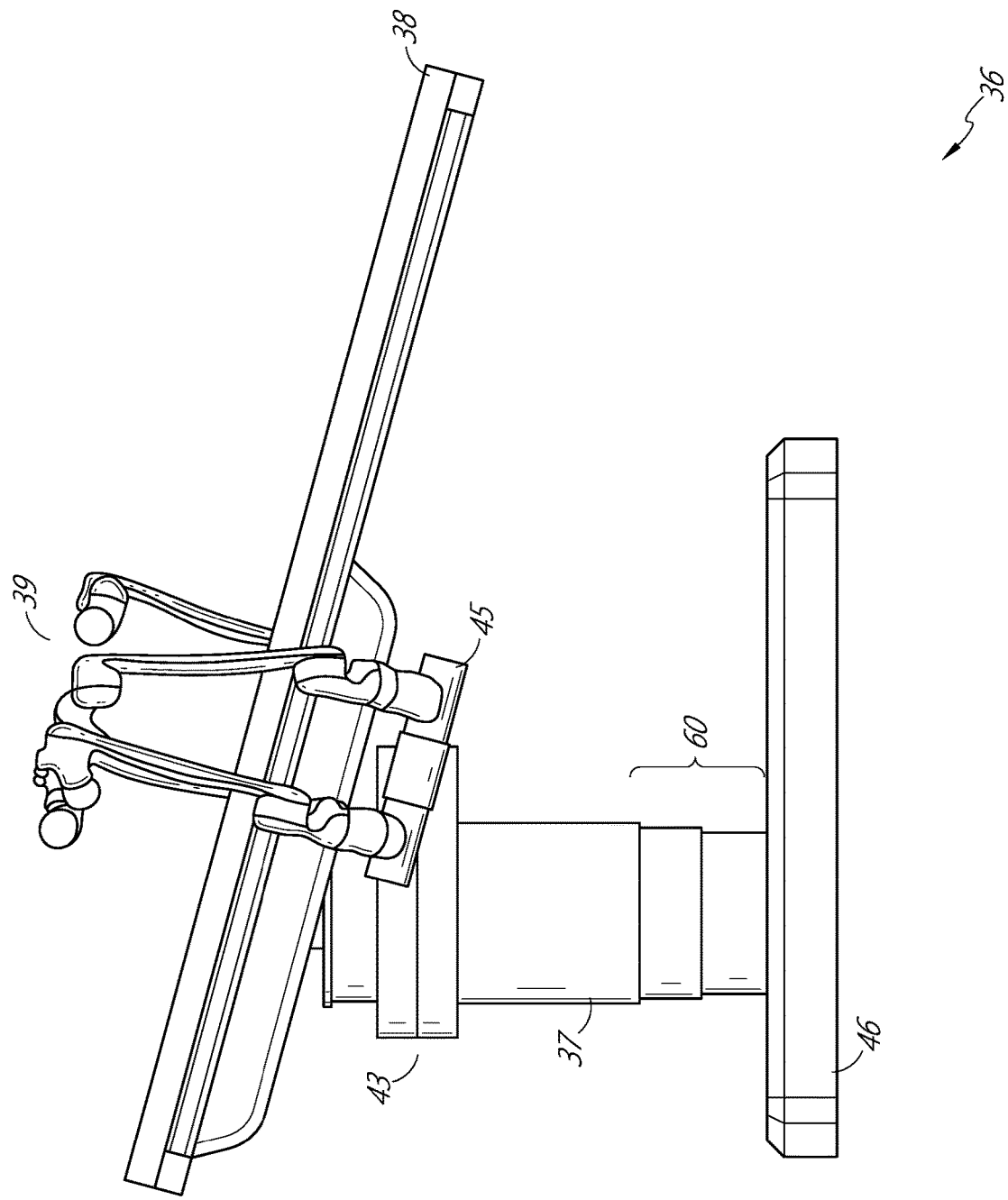
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
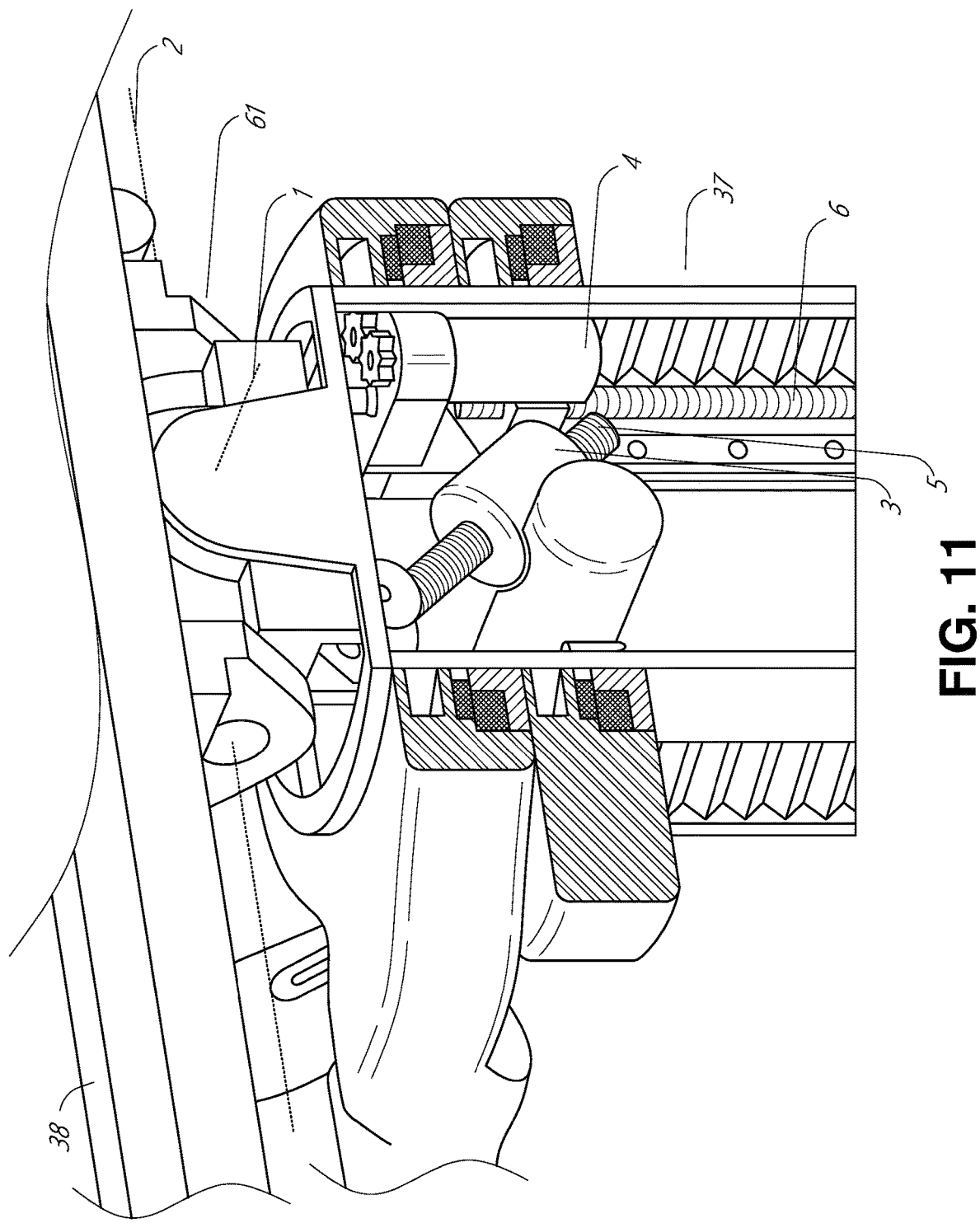
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple DoF. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
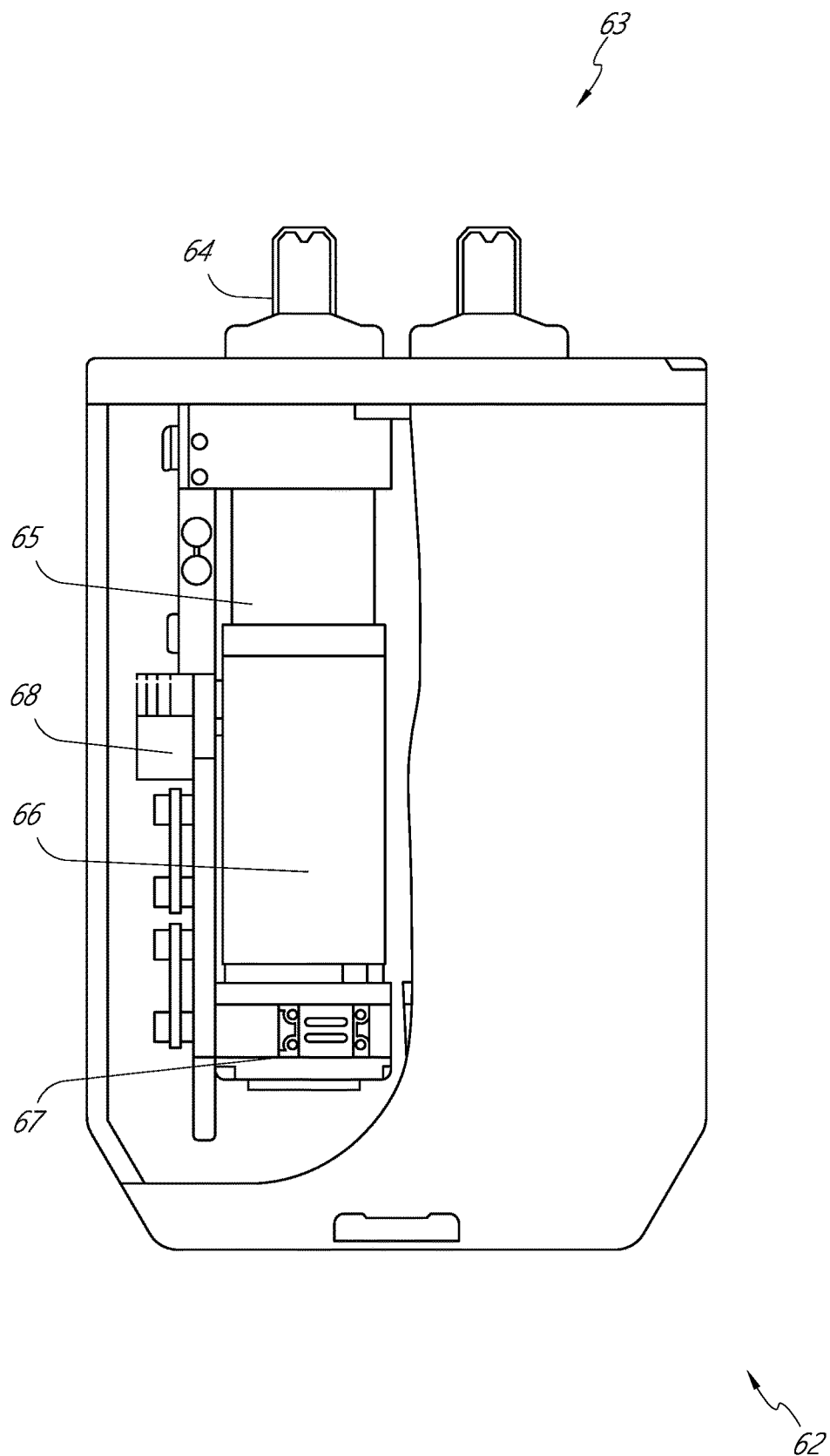
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
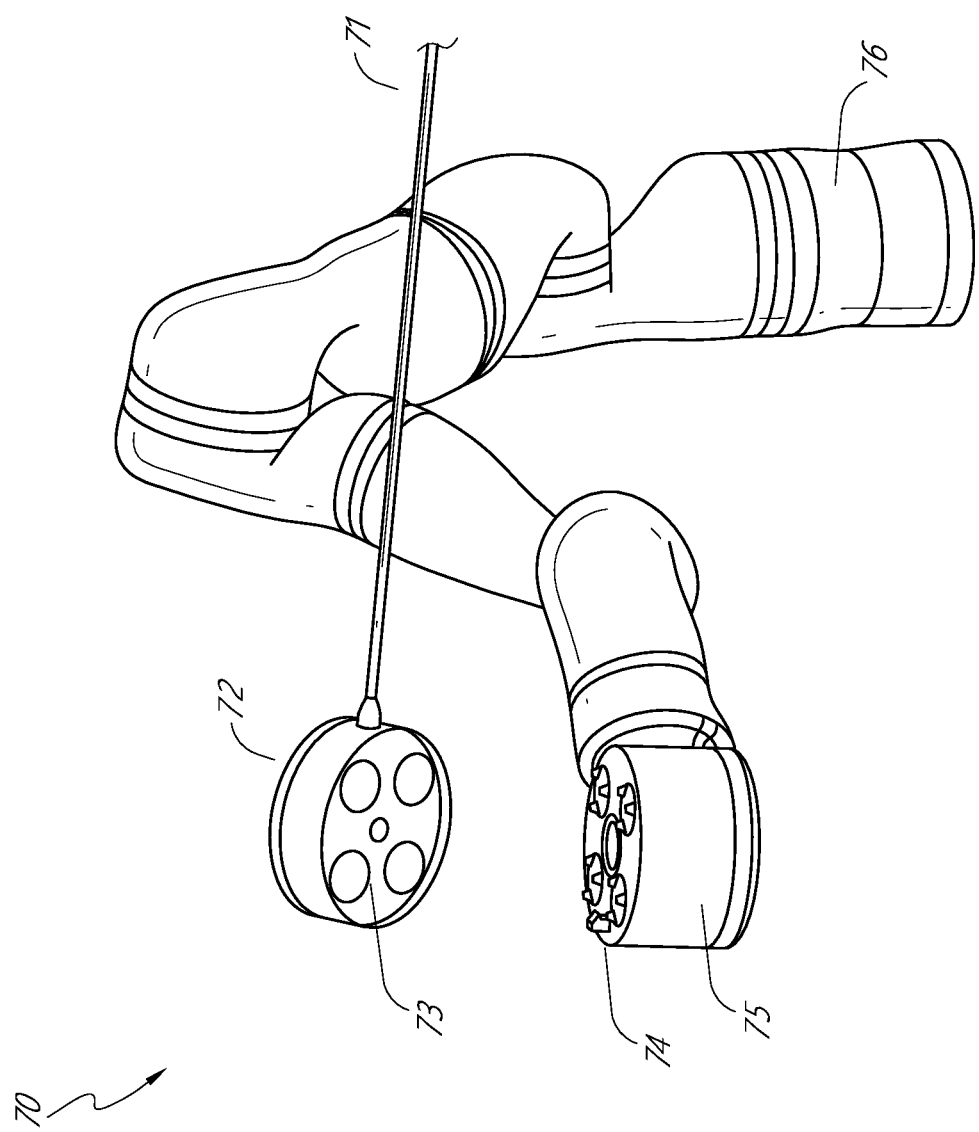
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
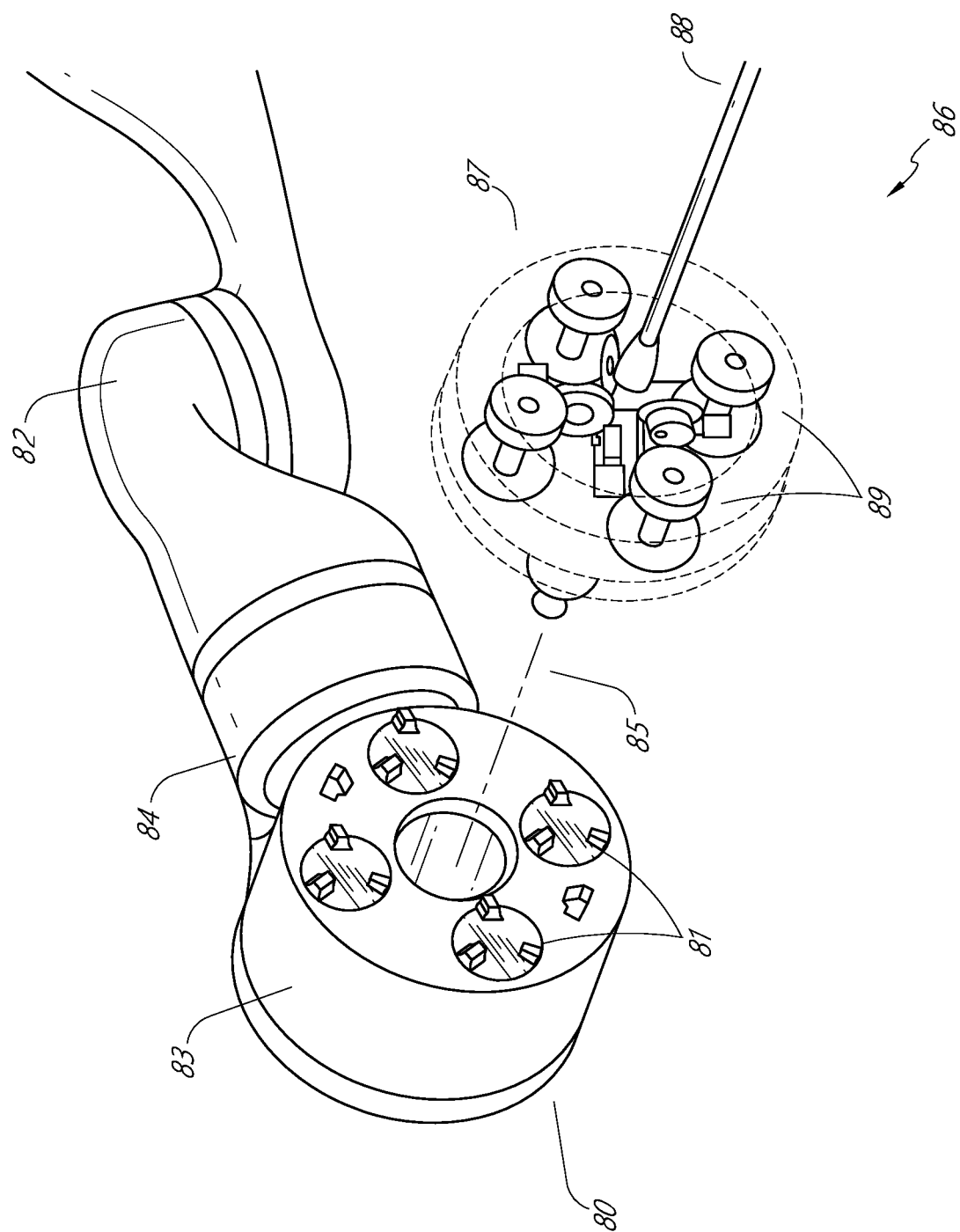
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
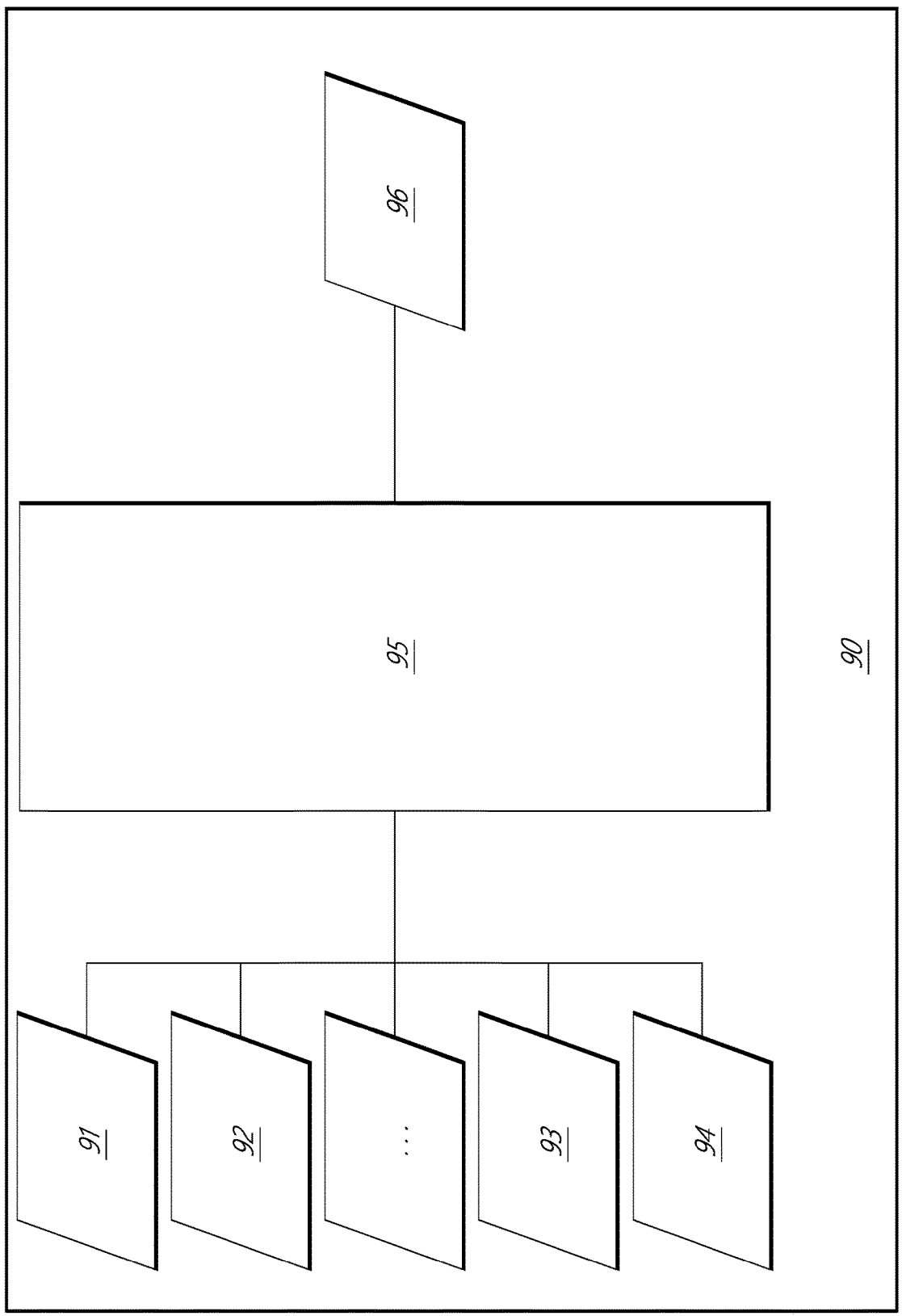
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator). The location data 96 may also be referred to herein as "state data" which describes a current state of the distal tip of the medical instrument with respect to a model (e.g., a skeletal model) of the anatomy of the patient. The state data may include information such as a position and orientation of the distal tip of the medical instrument for a given sample period. For example, when the patient's anatomy is modeled using a skeletal model based on a midpoint of the luminal network, the position may take the form of a segment ID and a depth along the segment.

The various input data 91-94 are now described in greater detail. Pre-operative mapping may be accomplished through the use of the collection of low dose CT scans. Pre-operative CT scans are reconstructed into three-dimensional (3D) images, which are visualized, e.g., as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a 3D volume of the patient's anatomy, referred to as preoperative model data 91. The use of center-line geometry is discussed in U.S. patent application Ser. No. 14/523,760, issued as U.S. Pat. No. 9,763,741 on Sep. 19, 2017, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Multi-Region Medical Procedures.

Embodiments of the disclosure relate to systems and techniques for providing multiple perspectives of an anatomical region during medical procedures.

During a minimally invasive procedure, one or more medical tools may be inserted into the patient via one or more respective access points (e.g., cannulas placed in the patient). In contrast to open medical procedures, a minimally invasive procedure may involve the use of a camera to provide a view of the targeted anatomy and the medical tool(s). For example, a medical tool may be inserted into the patient via a first cannula inserted into a first access point and a camera may be inserted into the patient via a second cannula inserted into a second access point.

Certain medical procedures may involve accessing a plurality of anatomical regions (e.g., anatomical quadrants of the patient). Due to the structure of the medical tools, it may be necessary to place additional access points in the patient to provide access to the different portions of the targeted anatomies. After changing the point(s) of entry for a subsequent stage(s) of the medical procedure, the camera may no longer provide an adequate view of the target anatomies and/or the medical tools. That is, the view provided by the camera may be obstructed by part of the patient's anatomy and/or the camera may be oriented in a direction that does not provide a view of the target location for the subsequent portion of the procedure. This disclosure provides a number of embodiments to address such situations.

Specifically, certain embodiments provide for systems and techniques for operating from multiple surgical perspectives using a robotic surgical system, which may include a telemanipulated control system. One advantage of such a technique includes the capability to view multiple quadrants (e.g., the left lower quadrant, left upper quadrant, right upper quadrant, and right lower quadrant of a patient's abdomen) during a medical procedure without undocking the robotic arms from cannulas positioned into the patient. The undocking and redocking of robotic arms can interrupt surgical workflow.

Figure 16A:
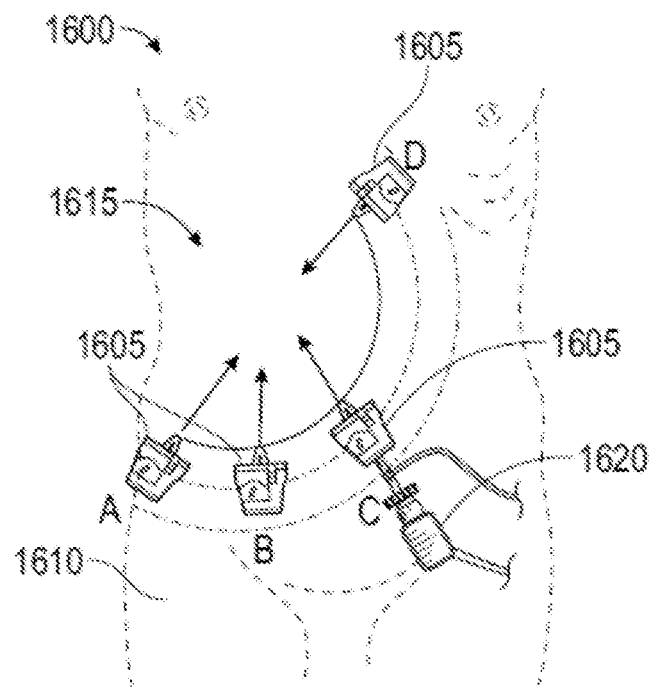
FIGS. 16A-16C illustrate exemplary cannula placement for different surgical procedures which may be used for medical procedures in accordance with aspects of this disclosure.
Figure 16B:
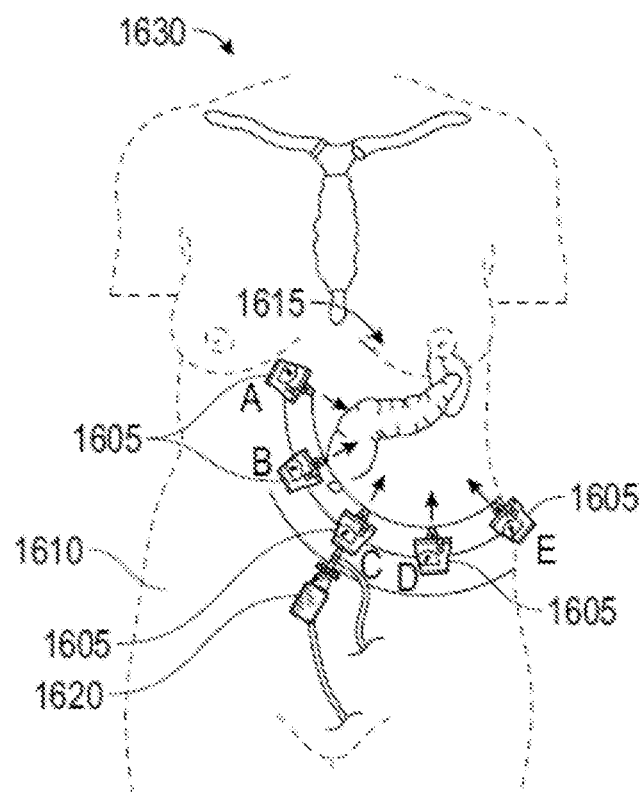
Figure 16C:
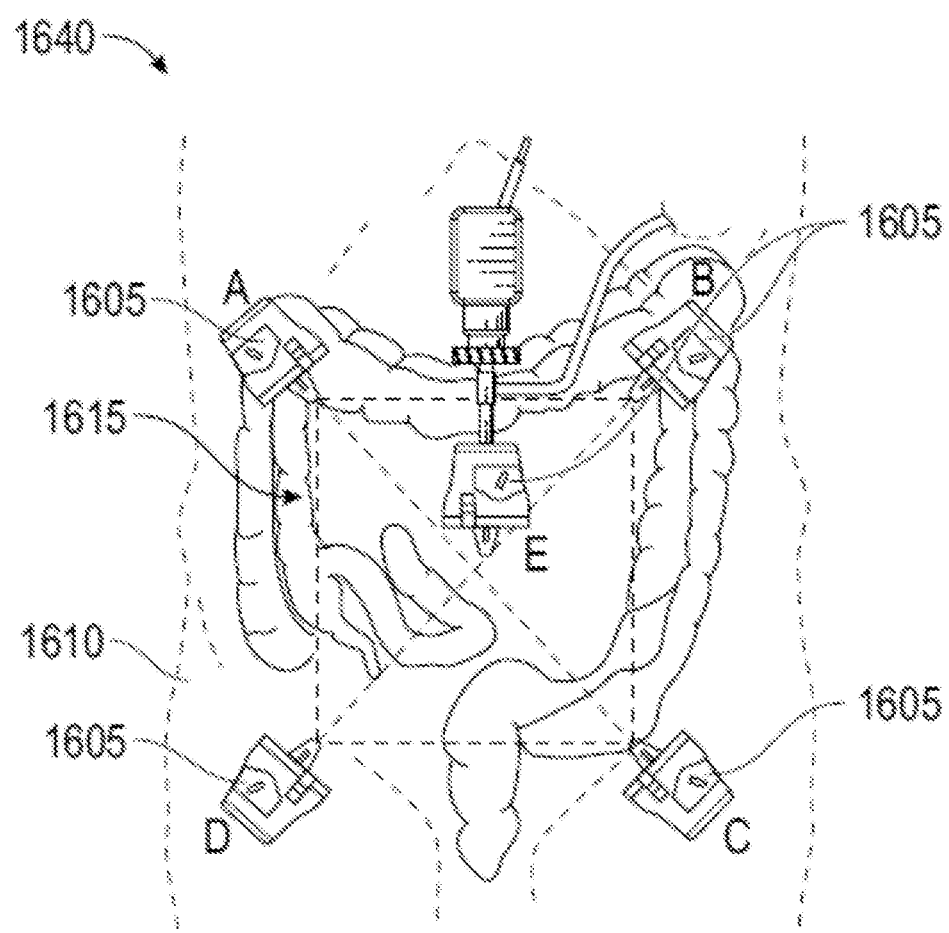

Manual and robotic medical procedures may include performing a medical procedure, such as a surgical procedure, in different regions of a patient. FIGS. 16A-16C illustrate exemplary cannula placements for various types of surgical procedures in accordance with aspects of this disclosure. In particular, FIG. 16A illustrates an example surgical environment 1600 including the placement of four cannulas 1605 (labeled A, B, C, and D) placed at a number of anatomical locations within a patient 1610 to provide access to at least a portion of the patient's anatomy 1615. In the example of FIG. 16A, the illustrated placement of the cannulas may allow access to the right upper quadrant of the patient's abdomen.

A camera may be docked to one of the cannulas 1605 (e.g., cannula C) to provide a view of the right upper quadrant. Although not illustrated, medical instruments may be docked to one or more of the cannulas 1605 labeled A, B, and D. Each of the cannulas provides access to the patient's anatomy 1615 from a unique location and/or orientation, allowing for flexibility in the manner in which the medical procedure is performed. The angles from which medical tools may access the patient's anatomy 1615 from the cannulas 1605 are illustrated by arrows extending from the respective cannulas 1605. In one example, during an initial stage of a medical procedure a physician may use medical tools docked to the cannulas 1605 labeled A and B, and at a subsequent stage may use medical tools docked to the cannulas 1605 labeled B and D. By using medical tools docked to different cannulas 1605, the physician may be able to access the patient's anatomy 1615 from different angles, allowing more options for direct access to various portions of the patient's anatomy 1615. As an example, as shown in FIG. 16A, the cannulas 1605 labeled A and D may provide access to the patient's anatomy 1615 from substantially opposite sides, allowing the physician access to both sides of the anatomy 1615 by simply selecting the medical tools docked to the cannulas 1605 labeled A and D.

FIGS. 16B and 16C provide additional example surgical environments 1630 and 1640 including the placement of a plurality of cannula 1605 for access to other regions of a patient's abdomen. Features which are the same or similar to those described in connection with FIG. 16A are given the same or similar labels in FIGS. 16B and 16C. In the example surgical environment 1630 of FIG. 16B, five cannulas 1605 labeled A, B, C, D, and E are placed in anatomical locations of the patent 1610 to provide access to a left upper quadrant of the patient's 1610 abdomen. Likewise, in FIG. 16C, the surgical environment 1640 includes the placement of five cannulas 1605 labeled A, B, C, D, and E in anatomical locations of the patent 1610 to provide access to a multiple quadrants of the patient's 1610 abdomen. The cannula 1605 placement of FIG. 16C may be provided to perform a colectomy as an example surgical procedure.

For manual surgeries, the physician may have the flexibility to view and perform a medical procedure in any quadrant of a patient. However, during a manual surgery the physician may be required to physically walk around the surgical platform to adjust the camera and tools for different workspaces, which can be time consuming and inconvenient, and may interrupt surgical workflow. Moreover, manual surgeries may lack the precision of robotic surgeries, thereby increasing a risk of harm to the patient.

For robotic surgeries, robotic surgical systems may allow a user to perform a surgery from a master console. However, a limitation of some surgical robotic systems is that the systems do not provide an adequate range of options for viewing and performing surgery in multi-quadrants. One problem is that the robotic arms may be arranged to fan out in a way that makes collisions between robotic arms more likely, such that multi-quadrant viewing for a medical procedure can be inconvenient if not impossible in some scenarios. To view or perform surgeries in multiple-quadrants, it may be the case that either the cart base or the boom (which moves the robot arms) of a given surgical robotic system may need to be moved to provide an adequate view of an anatomical quadrant, which may involve undocking the robotic arms from cannulas, leading to interruption in surgical workflow. These problems may be particularly pronounced in surgical robotic systems in which the robotic arms are generally oriented in a similar fashion (e.g., in a unilateral robotic arm arrangement in which the angle of entry for the robotic arms is directed towards the cart base).

In view of the above, aspects of this disclosure relate to systems and techniques which can provide multiple perspectives of a given surgical procedure while improving the efficiency of the surgical workflow.

A. Camera Port Hopping.

The present embodiments address the ability of a robotic system that is capable of "camera hopping" without the need to undock a robotic arm. The term "camera hopping" refers to moving a camera from one cannula to another to obtain a different viewpoint. In other robotic systems, in order to perform camera hopping, robotic arms will often need to be undocked, thereby interrupting a surgical operation. In contrast, the robotic system described herein advantageously allows camera hopping to be performed with ease, without having to undock robotic arms from their respective cannulas.

Figure 17:
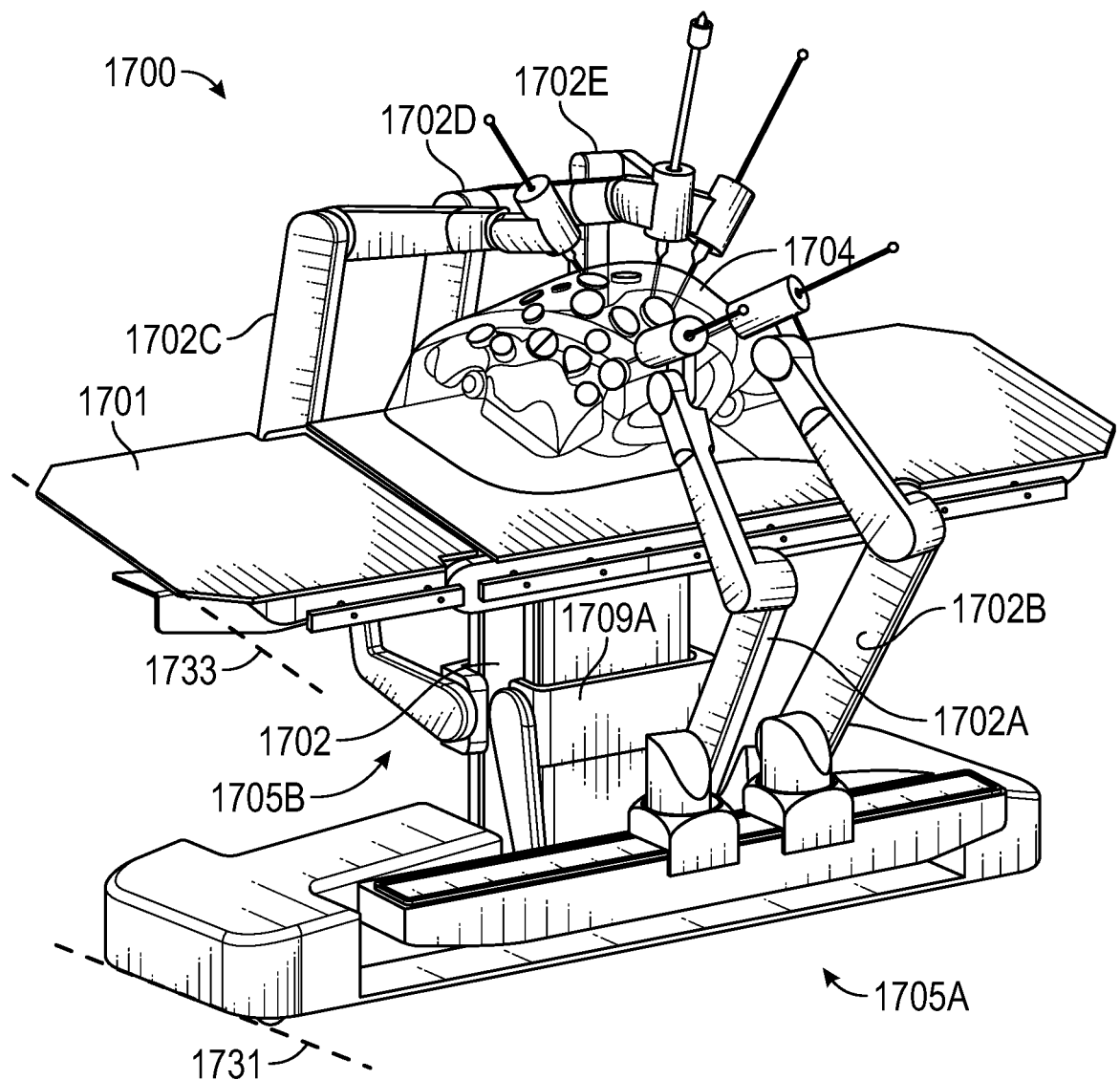
FIG. 17 illustrates an embodiment of a surgical robotic system configured to provide multiple perspectives during a medical procedure in accordance with aspects of this disclosure.

Certain embodiments for providing multiple perspectives for a medical procedure as disclosed herein may involve camera port hopping. FIG. 17 illustrates an embodiment of a surgical robotic system configured to provide multiple perspectives during a medical procedure in accordance with aspects of this disclosure. In particular, FIG. 17 is an isometric view of a surgical robotics system 1700 with two adjustable arm supports 1705A, 1705B and a plurality of robotic arms 1702A, 1702B, 1702C, 1702D, 1702E configured for a medical procedure (e.g., a laparoscopic procedure) according to one embodiment. In the illustrated embodiment, a first adjustable arm support 1705A supports a first robotic arm 1702A and a second robotic arm 1702B, and a second adjustable arm support 1705B supports a third robotic arm 1702C, a fourth robotic arm 1702D, and a fifth robotic arm 1702E.

In the illustrated embodiment, the table 1701 supporting the patient 1704 is positioned at an angle relative to the floor. That is, rather than being parallel, a table surface plane 1733 may be angled with respect to a support surface plane 1731. The first adjustable arm support 1705A, positioned on the lower side of the table 1701, can be positioned in a low position such that the first robotic arm 1702A and the second robotic arm 1702B can access the patient 1704. As illustrated, the second adjustable arm support 1705B is positioned at a higher position (which may be lower than the table support surface 1733) such that the third robotic arm 1702C, the fourth robotic arm 1702D, and the fifth robotic arm 1702E can reach over and access the patient 1704.

In some embodiments, the adjustable arm supports 1705A and 1705B are attached to the bed with a support structure that provides several DoF (e.g., lift, lateral translation, tilt, etc.). A first degree of freedom allows for adjustment of the adjustable arm support in the z-direction ("Z-lift"). For example, as will be described below, the adjustable arm support 1705A can include a carriage 1709A configured to move up or down along or relative to a column 1702 supporting the table 1701. A second degree of freedom can allow the adjustable arm supports 1705A and 1705B to tilt. For example, the adjustable arm supports 1705A and 1705B can include a rotary joint, which can, for example, permit the arm supports 1705A and 1705B to be aligned with a bed in a Trendelenburg position. A third degree of freedom can allow the adjustable arm supports 1705A and 1705B to "pivot up." This degree of freedom can be used to adjust a distance between the side of the table 1701 and the adjustable arm supports 1705A and 1705B. A fourth degree of freedom can permit translation of the adjustable arm supports 1705A and 1705B along a longitudinal length of the table. The adjustable arm supports 1705A and 1705B can allow for adjustment of the position of the robotic arms relative to, for example, the table 1701. In some embodiments, these DoF can be controlled serially, in which one movement is performed after another. In other embodiments, different DoF can be controlled in parallel. For example, in some embodiments, one or more linear actuators can provide both Z-lift and tilt. Additional example embodiments of surgical robotic systems which may be configured to perform the camera port hopping techniques described herein are described in U.S. Provisional Patent Application No. 62/618,489, filed on Jan. 17, 2018, and in U.S. patent application Ser. No. 16/234,975, filed Dec. 28, 2018, issued as U.S. Pat. No. 10,517,692 on Dec. 31, 2019, each of which is herein incorporated by reference in its entirety.

As will be clear from the embodiment described herein, the bilateral location of the robotic arms 1702A, 1702B, 1702C, 1702D, 1702E on opposing sides of the table 1701 allows the robotic arms 1702A, 1702B, 1702C, 1702D, 1702E to be deployed on each side of a patient 1704, which makes it easier to dock the robotic arms 1702A, 1702B, 1702C, 1702D, 1702E to cannulas in different anatomical quadrants. The robotic system may include robotic arms 1702A, 1702B, 1702C, 1702D, 1702E capable of being deployed from a stowed position via vertically adjustable bars/arm supports placed on each side of the bed 1701. The robotic arms 1702A, 1702B, 1702C, 1702D, 1702E may be capable of translating along rails formed on the vertically adjustable bars/arm supports, which allows them to maintain spacing during surgical procedures.

Figure 18:
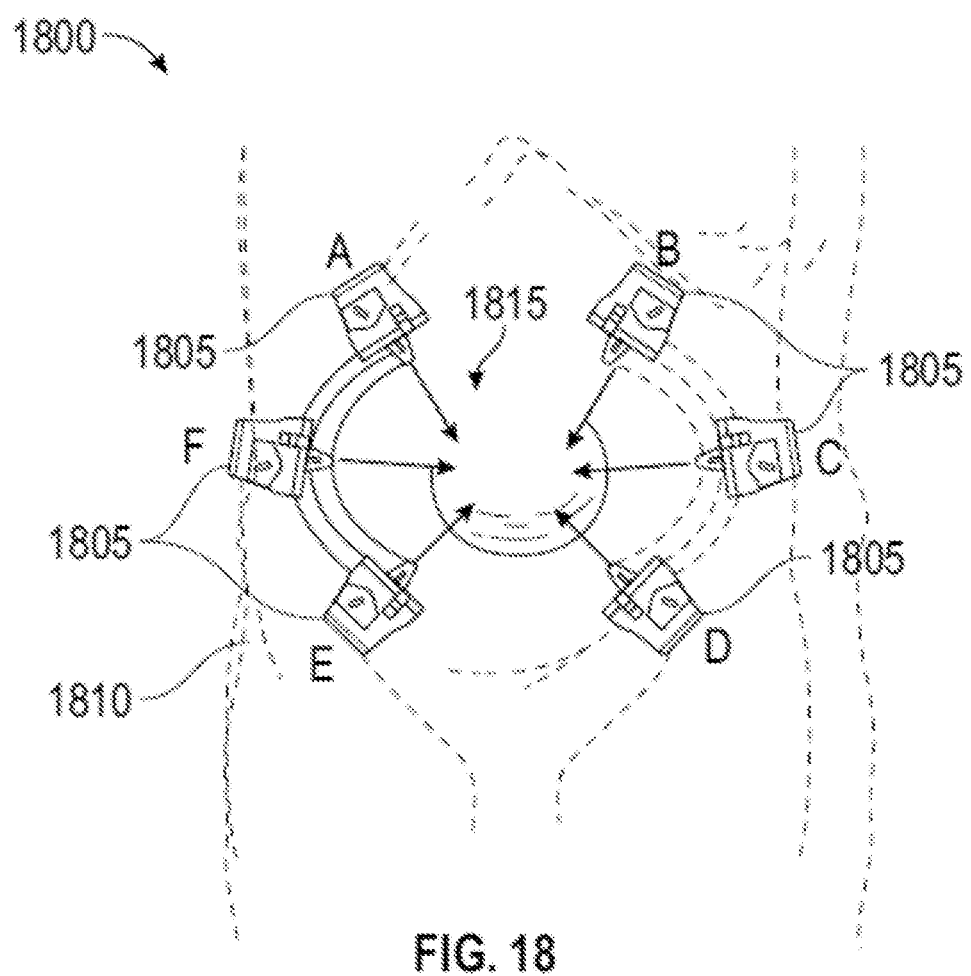
FIG. 18 illustrates an exemplary cannula placement which may be used for camera hopping during a medical procedure in accordance with aspects of this disclosure.

One technique which may be used to provide multiple surgical perspectives using a bilateral robotic surgical system such as the system 1700 illustrated in FIG. 17 involves camera port hopping. In a procedure using camera port hopping, a number of cannulas may be placed in a number of anatomical positions in a patient such that a camera may be moved between two of more of the cannulas. In some embodiments, the camera can be rigid, while in other embodiments, the camera can be articulatable. FIG. 18 illustrates an exemplary cannula placement in which a camera may hop from a first position to a second position during a medical procedure in accordance with aspects of this disclosure. In particular, FIG. 18 illustrates an example surgical environment 1800 as set up for an example midline abdominal medical procedure. The surgical environment 1800 includes the placement of six cannulas 1805 (labeled A, B, C, D, E, and F) placed at a number of anatomical locations within a patient 1810. The cannulas 1805 may provide access to at least a portion of the patient's anatomy 1815.

In exemplary embodiments, the surgical robotic system is advantageously configured to enable a robotically controlled camera (e.g., a rigid or articulatable camera) to achieve multiple perspectives without having to undock the robotic arms from cannulas. For example, in the example of FIG. 18, a physician may place six cannulas 1805 into a patient 1810, including placing a cannula 1805 in each of the quadrants (e.g., a right upper quadrant, a left upper quadrant, a right lower quadrant and a left lower quadrant) for tools, as well as a pair of additional cannulas 1805 for receiving a camera therein. Robotic arms, which can used to deliver cameras or working tools, can be attached or docked to each of the cannulas 1805. Thus, four surgical tools (not illustrated) may be respectively coupled to four robotic arms (not illustrated) and the robotic arms may insert the surgical tools into the cannulas 1805 labeled A, B, D, and E. In some embodiments, the robotic arms can be configured to extend bilaterally on two sides of a patient or platform, as in the system in FIG. 17. In some embodiments, the bilateral nature of the robotic arms assists in facilitating the ability to camera hop with ease, without having to undock robotic arms. Examples of surgical tools that may be held by the robotic arms and docked to the cannulas 1805 include graspers, cutters, hooks, staplers, sealers and/or catheters. The cannulas labeled C and F may be positioned so as to receive a scope or camera configured to provide a view of one or more of the patient's abdominal quadrants.

Figure 19A:
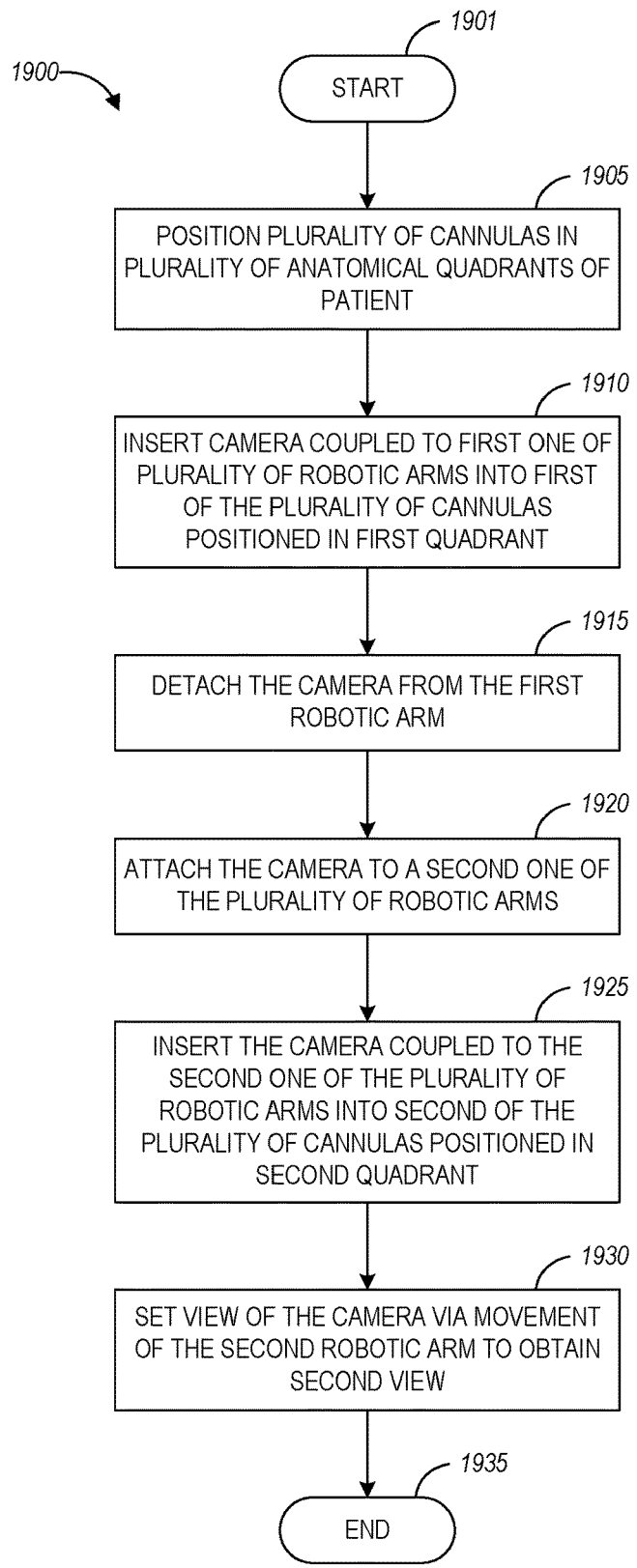
FIG. 19A is a flowchart illustrating an example method operable by a robotic system, or component(s) thereof, for camera hopping to obtain multiple perspectives of a medical procedure in accordance with aspects of this disclosure.

Using an environment set up in a manner similar to the environment 1800 illustrated in FIG. 18, the surgical robotic system may be configured to move the camera between two cannulas (also referred to generally as camera hopping) to provide multiple perspectives of the patient's anatomy 1815. FIG. 19A is a flowchart illustrating an example method operable by a robotic system, or component(s) thereof, for camera hopping to obtain multiple perspectives of a medical procedure in accordance with aspects of this disclosure. For example, the steps of method 1900 illustrated in FIG. 19A may be performed by processor(s) and/or other component(s) of a medical robotic system (e.g., robotically-enabled system 10 or the surgical robotics system 1700) or associated system(s). For convenience, the method 1900 is described as performed by the "system" in connection with the description of the method 1900.

The method 1900 begins at block 1901. At block 1905, the method 1900 may involve positioning a plurality of cannulas in a plurality of anatomical quadrants of a patient. In some embodiments, there is at least one cannula positioned in each of the anatomical quadrants (upper left quadrant, upper right quadrant, lower left quadrant, lower right quadrant) of a patient. Each of the plurality of cannulas is capable of receiving therein at least one of a surgical tool or a camera. When performed in the example environment 1800 of FIG. 18, the cannulas 1805 labeled A, B, D, and E may be positioned in each of the abdominal quadrants of the patient 1810 by a physician or an assistant. Cannulas 1805 labeled C and F may also be positioned on the patient 1810 substantially in line with the patient's 1810 midline.

At block 1910, the method 1900 may involve the system inserting a camera coupled to a first one of a plurality of robotic arms into a first of the plurality of cannulas positioned in a first quadrant. The camera may be configured to generate an image including a first view. Referring again to the environment 1800, the camera may be inserted into the cannula 1805 labeled F and positioned in a first quadrant of the patient 1810. The first robotic arm may be positioned on the patient's 1810 right side such that the camera can be inserted into the cannula 1805 labeled F. Thus, the first robotic arm may be docked to the cannula 1805 labeled F which is located in the first quadrant.

At block 1915, the method 1900 may involve detaching the camera from the first robotic arm. At block 1920, the method 1900 may involve attaching the camera to a second one of the plurality of robotic arms. Blocks 1915 and 1920 may involve the physician or assistant manually detaching the camera from the first robotic arm and attaching the camera to the second robotic arm.

At block 1925, the method 1900 may involve inserting the camera coupled to the second one of the plurality of robotic arms into a second of the plurality of cannulas positioned in a second quadrant. Here, the second robotic arm may be positioned on the patient's 1810 left side such that the camera can be inserted into the cannula 1805 labeled C. Thus, the second robotic arm may be docked to the cannula 1805 labeled C, which is located in the second quadrant.

At block 1930, the method 1900 may involve the system setting a view of the camera via movement of the second robotic arm to obtain a second view. As is discussed in greater detail below, the second robotic arm may be configured to reposition the camera to adjust the view of the patient's anatomy 1815. The view may include a view of at least a portion of the patient's anatomy 1815 and one or more surgical tools inserted through one or more of the cannulas 1805 labeled A, B, D, and E. The physician may then be able to perform at least a portion of a surgical procedure using the surgical tool(s) based on the view of the camera as visual feedback. The method 1900 ends at block 1935.

Since in the example environment 1800, the first and second robotic arms are positioned on opposing sides of the patient's body, the insertion of the camera into the respective cannulas 1805 labeled F and C may provide views of different areas of the patient's 1810 anatomy. By moving the camera between the two cannulas 1805 labeled F and C, the physician may be able to reposition the camera to obtain a desired view of the patient's anatomy 1815. The perspectives provided by the different views obtained by docking the camera to the two cannulas 1805 labeled F and C may correspond to different portions of a medical procedure being performed by the physician.

For example, while the camera is in the first position docked to the cannula 1805 labeled F, the physician may use surgical tools docked to the cannulas labeled A and E to perform a procedure accessible from the patient's 1810 right side. Using the surgical tools docked to the cannulas labeled A and E, the physician may be able to navigate the tools to one of the patient's 1810 the left upper quadrant and left lower quadrant. With the camera docked to the cannula 1805 labeled F, the camera may provide a perspective view of the left upper quadrant and/or left lower quadrant. Further, at block 1930, the physician may be able to set the view of the camera to focus the view on a desired region of the patient's anatomy 1815. For example, when performing a medical procedure in the left upper quadrant, the physician may, via commands to move the first robotic arm, adjust the perspective view of the camera such that the left upper quadrant is substantially within the view of the camera.

When the medical procedure involves performing a portion of the procedure in one of the patient's 1810 right upper quadrant and right lower quadrant, the physician may select one or more of the surgical tools docked to the cannulas 1805 labeled B and D. However, since the camera located in the first position is docked to the cannula 1805 labeled F, the camera may not provide a view of the patient's 1810 right upper quadrant and right lower quadrant. By camera hopping from the cannula 1805 labeled F to the cannula labeled C, for example, via blocks 1915 to 1930 of the method 1900, the physician may be able to obtain a view of one of more of the patient's 1810 right upper quadrant and right lower quadrant.

Using one of more of the disclosed techniques, the camera can hop from one cannula to another during a surgical procedure. Throughout the procedure, including the camera hopping, the robotic arms coupled with the surgical tools may remain docked to their respective cannulas 1805, which is novel compared to other robotic systems. The robotic system herein provides an advantage over other robotic systems which may not be able to dock robotic arms to cannulas in each of the four quadrants (e.g., since the arms may collide with one another). Further, due to the limited docking capabilities of the surgical system of other robotic systems, if a physician wanted to camera hop between the two cannulas, the physician would have to undock one or more robotic arms from a first set of cannulas, adjust the cart or boom, then re-dock the robotic arms to a different set of cannulas, thereby interrupting surgeon workflow. In contrast, by employing the method 1900 in connection with a robotic surgical system having a bilateral configuration as illustrated in the example of FIG. 17, the robotic arms can stay docked to the respective cannulas 1805 located in each of the quadrants throughout the entire medical procedure, even while camera hopping. Accordingly, the physician can achieve multiple perspectives and different lines of sight-all without having to undock the robot arm(s) during the medical procedure.

Figure 19B:
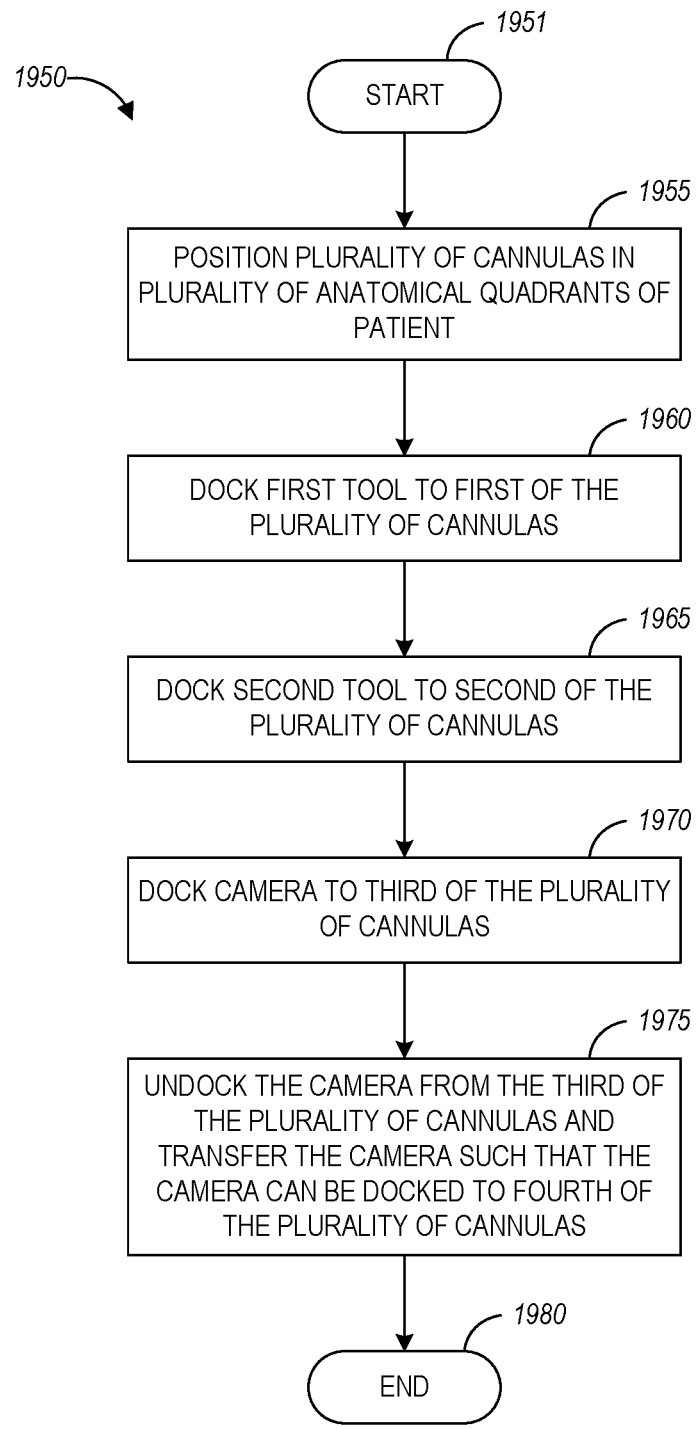
FIG. 19B is a flowchart illustrating another example method operable by a robotic system, or component(s) thereof, for camera hopping to obtain multiple perspective of a medical procedure in accordance with aspects of this disclosure.

Another example approach to camera hopping may involve moving the camera between cannulas without detaching the camera from the robotic arm. In other words, rather than performing camera hopping by moving a camera from a first robotic arm docked to a first cannula to a second robotic arm docked to a second cannula, in the present embodiment, camera hopping can be performed by moving both the camera and a coupled robotic arm from a first cannula to a second cannula. FIG. 19B is a flowchart illustrating another example method operable by a robotic system, or component(s) thereof, for camera hopping to obtain multiple perspective of a medical procedure in accordance with aspects of this disclosure. For example, the steps of method 1950 illustrated in FIG. 19B may be performed by processor(s) and/or other component(s) of a medical robotic system (e.g., robotically-enabled system 10 or the surgical robotics system 1700) or associated system(s). For convenience, the method 1950 is described as performed by the "system" in connection with the description of the method 1950.

The method 1950 begins at block 1951. At block 1955, the method 1950 may involve positioning a plurality of cannulas in a plurality of anatomical quadrants of a patient. Each of the plurality of cannulas may be capable of receiving therein at least one of a surgical tool or a camera. As described above, when performed in the example environment 1800 of FIG. 18, the cannulas 1805 labeled A, B, D, and E may be positioned in each of the abdominal quadrants of the patient 1810 by a physician or an assistant. Cannulas 1805 labeled C and F may also be placed on the positioned on the patient 1810 substantially in line with the patient's 1810 midline.

At block 1960, the method 1950 may involve the system docking a first tool to a first of the plurality of cannulas. The first tool may be coupled to a first of a plurality of robotic arms. At block 1965, the method 1950 may involve the system docking a second tool to a second of the plurality of cannulas. The second tool may be coupled to a second of the plurality of robotic arms. With continuing reference to FIG. 18, in one example, the first robotic tool and the second tool may be respectively docked to the cannulas 1805 labeled D and E. This may allow the physician access to perform a medical procedure on the patient's 1810 right upper quadrant and/or left upper quadrant.

At block 1970, the method 1950 may involve the system docking a camera to a third of the plurality of cannulas. Continuing with the above example, the camera may be docked to the cannula 1805 labeled F. Based on the view provided by the camera when docked to the cannula 1805 labeled F, the camera may provide a view of the left upper quadrant. However, the medical procedure may involve the physician performing a procedure on the patient's 1810 right upper quadrant, for which the camera may not be able to provide a view when docked to the cannula 1805 labeled F.

Accordingly, at block 1975, the method 1950 may involve the system undocking the camera from the third of the plurality of cannulas and transferring the camera such that the camera can be docked to a fourth of the plurality of cannulas. The fourth cannula 1805 may correspond to the cannula 1805 labeled C which may enable the camera to provide a view of the right upper quadrant, enabling the physician to continue with the medical procedure. In some embodiments, the camera and a coupled robotic arm can be undocked from the third of the plurality of cannulas and docked to the fourth of the plurality of cannulas. While the camera is undocked from the third cannula (e.g., the cannula 1805 labeled F) and transferred to the fourth cannula (e.g., the cannula 1805 labeled C), the first tool is advantageously capable of remaining docked to the first cannula 1805 labeled D and the second tool is advantageously capable of remaining docked to the second cannula labeled E. The method 1950 ends at block 1980.

B. Multiple Perspective Views without Undocking Robotic Arms.

One or more of the disclosed embodiments, which provide the physician with multiple perspective views of a patient's anatomy, enable a physician to perform a medical procedure in multiple quadrants without undocking the robotic arms from cannulas placed into the patient. FIGS. 20A-20D illustrate a number of operational perspectives which may be selected in accordance with aspects of this disclosure. As shown in these figures, six robotic arms can be positioned bilaterally-three on each side of the patient. A surgeon is advantageously capable of achieving multiple operational perspectives while keeping the robotic arms docked to their respective cannulas.

Figure 20A:
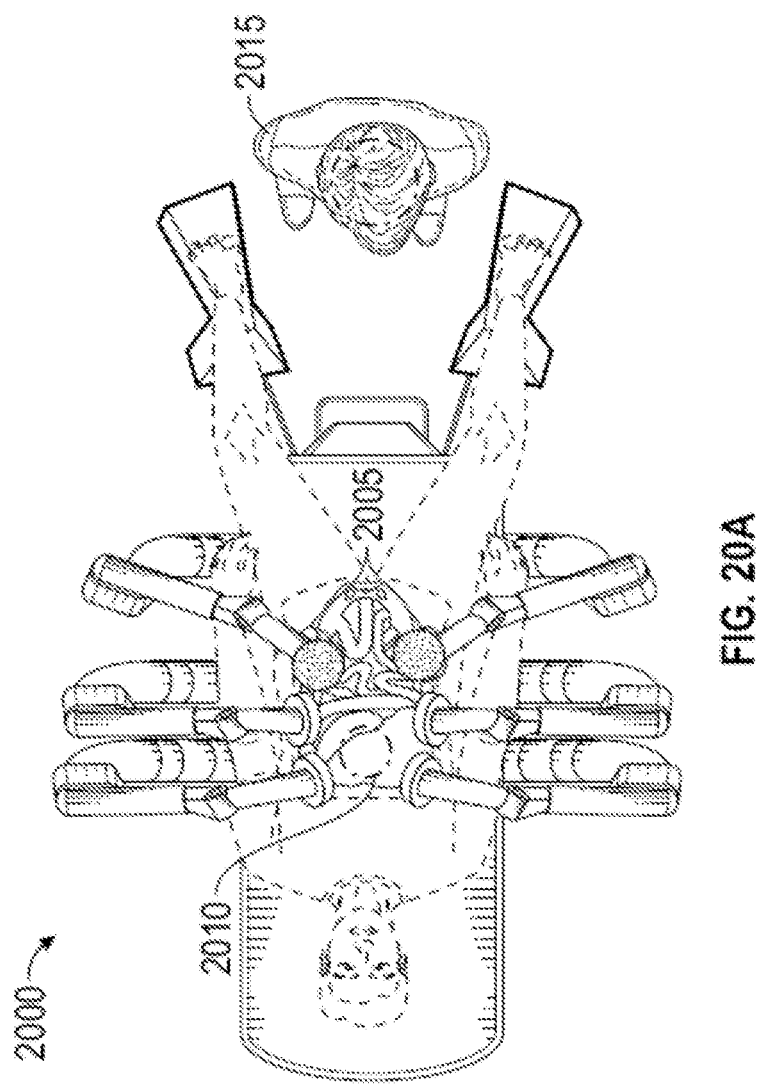
FIGS. 20A-20D illustrate a number of operational perspectives which may be selected in accordance with aspects of this disclosure.

FIG. 20A illustrates a first perspective 2000 which includes a selection of two robotic arms 2005 which may enable the physician to operate in a first anatomical space 2010. In the present embodiment, the two robotic arms 2005 are positioned bilaterally on opposite sides of the patient. While the physician may control the robotic arms 2005 from a control console (e.g., the console 31 of FIG. 1), the selection of the robotic arms 2005 may correspond to a first virtual or phantom operating position 2015 analogous to a traditional non-robotic operational perspective. The first perspective 2000 may correspond to a midline working cephalad operating position 2015.

Figure 20B:
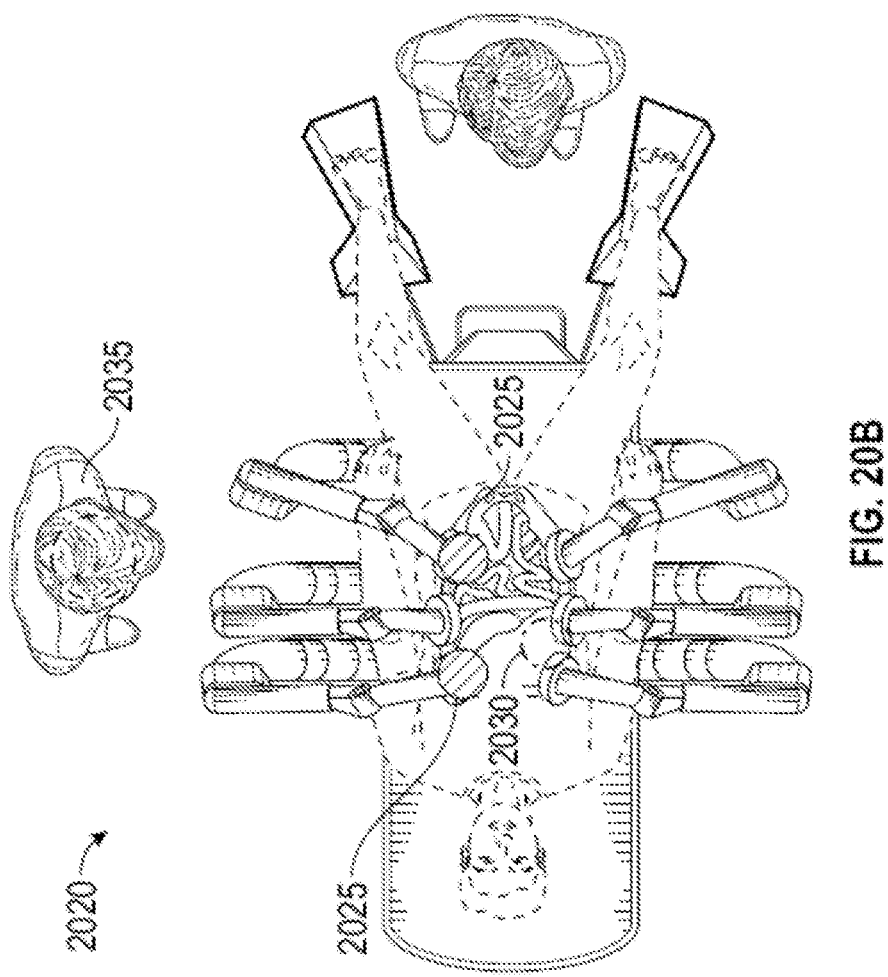

FIG. 20B illustrates a second perspective 2020 which includes a selection of two robotic arms 2025 which may enable the physician to operate in a second anatomical space 2030. In the second perspective 2020, the selection of the robotic arms 2025 may correspond to a second virtual operating position 2035 analogous to a traditional non-robotic operational perspective. The second perspective 2020 may correspond to a patient left side working toward patient right operating position 2035.

Figure 20C:
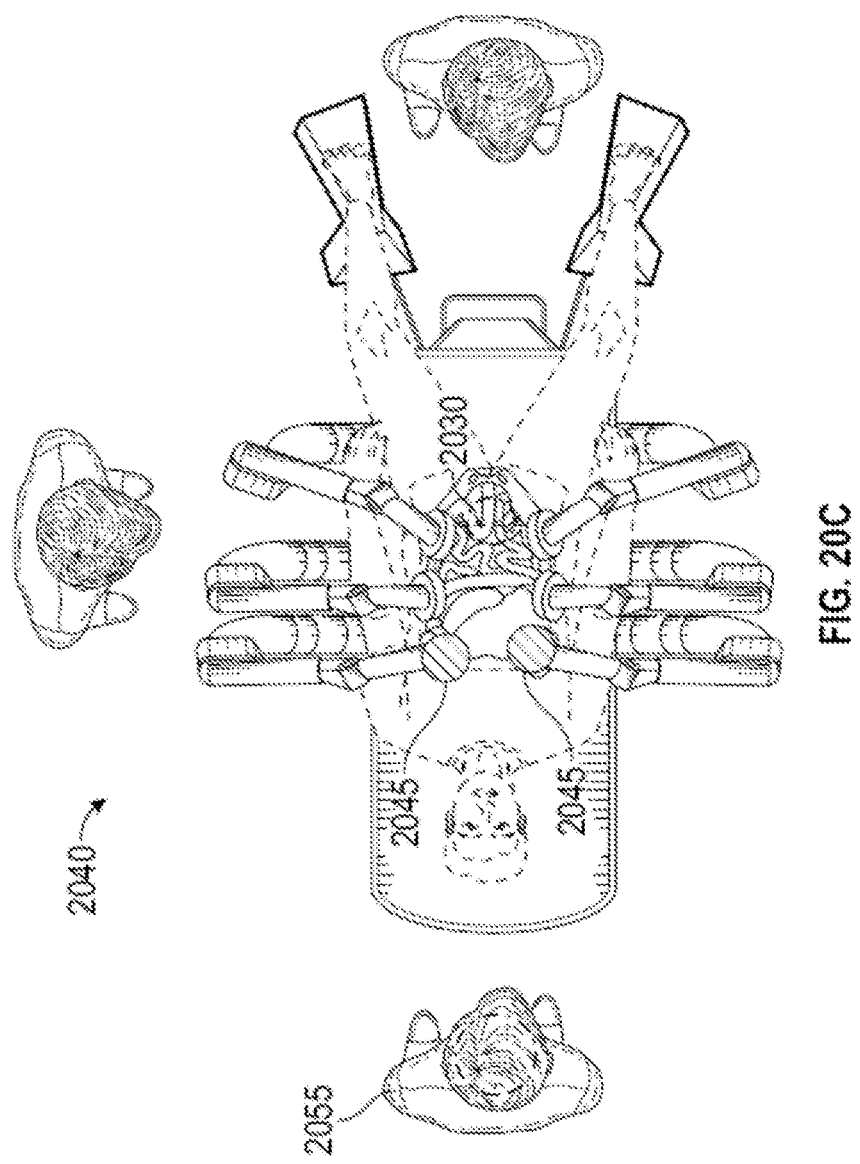
Figure 20D:
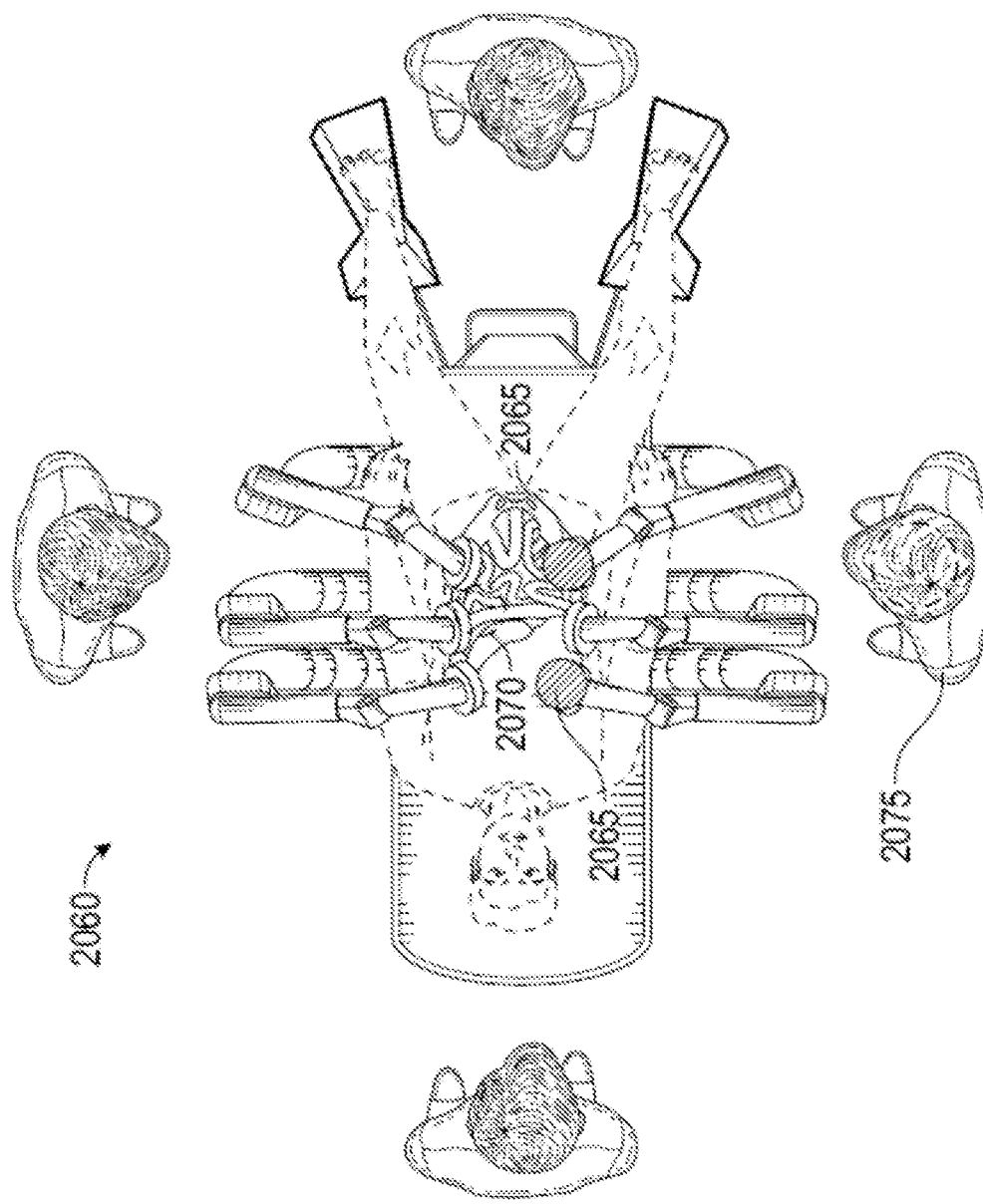

FIGS. 20C and 20D respectively illustrate a third perspective 2040 and a fourth perspective 2060 which include selection of two robotic arms 2045 and 2065. The selection of robotic arms 2045 and 2065 may respectively enable the physician to operate in a third anatomical space 2050 and a fourth anatomical space 2070. In the third perspective 2040, the selection of the robotic arms 2045 may correspond to a third virtual operating position 2055 while in fourth perspective 2060, the selection of the robotic arms 2065 may correspond to a fourth virtual operating position 2075. The third perspective 2040 may correspond to a midline working caudal operating position 2055. The fourth perspective 2060 may correspond to a patient right-side working toward patient left-side operating position 2075.

Although not illustrated, the system may be configured to allow for the selection of any combination of one or two of the robotic arms. The selection of two robotic arms located diagonally from each other may not have a directly analogous traditional non-robotic operational perspective since it may not be possible for a physician to physically operate the surgical tools when the tools are docked to cannulas that are placed beyond a certain distance apart. Thus, the use of a surgical robotic system may advantageously enable the selection of combinations of surgical tools that would otherwise not be possible for a single physician to operate.

C. Repositionable/Articulatable Camera for Multiple Perspectives.

Figure 21:
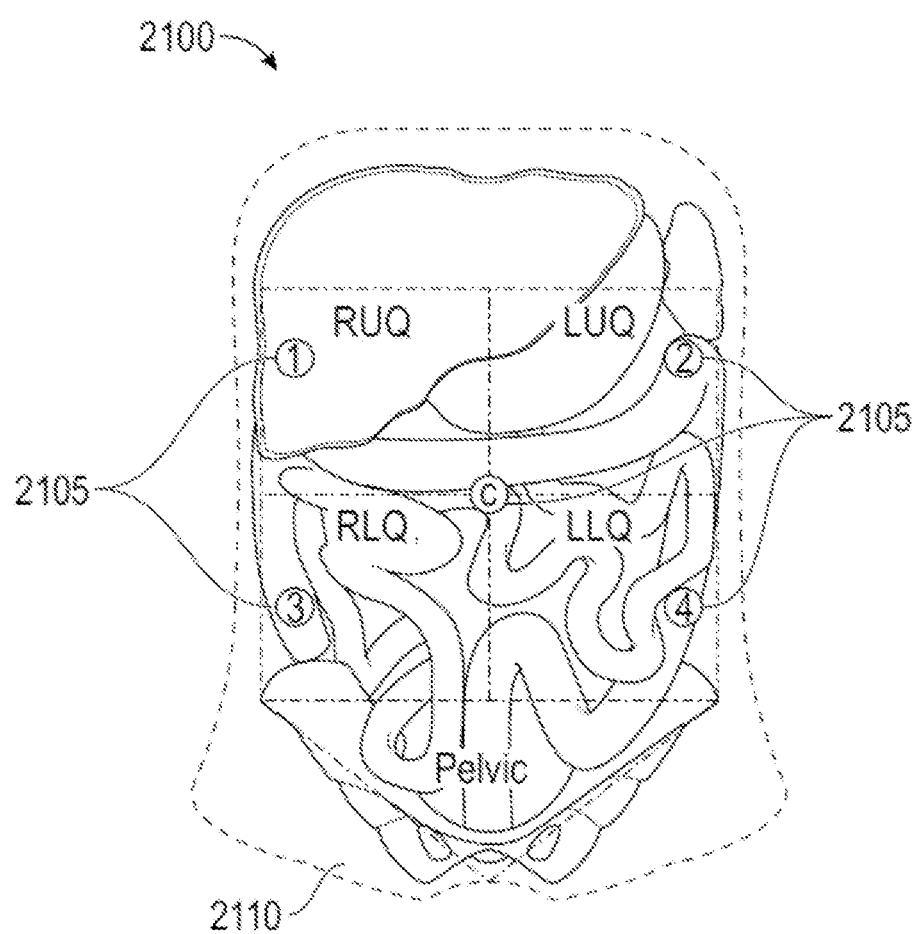
FIG. 21 illustrates an embodiment of an environment including the placement of multiple cannulas arranged for a laparoscopic procedure in accordance with aspects of this disclosure.

The present embodiments describe the ability to use an articulating camera to achieve multiple surgical perspectives with ease. In some embodiments, the articulating camera is capable of viewing multiple quadrants in a patient, such as a left upper quadrant, a right upper quadrant, a left lower quadrant and a right lower quadrant. Certain embodiments for providing multiple perspectives for a medical procedure as disclosed herein may involve the use of an adjustable and/or articulatable camera to provide the multiple perspectives. As an example, multiple perspectives provided by a camera may be particularly useful in a laparoscopic procedure. FIG. 21 illustrates an embodiment of an environment 2100 including the placement of multiple cannulas arranged for a laparoscopic procedure in accordance with aspects of this disclosure. In the example environment 2100, a plurality of cannulas 2105 may be inserted into a patient 2110 for a laparoscopic procedure.

Rather than the use of six cannulas 1805 as illustrated in the embodiment of FIG. 18, the environment 2100 of FIG. 21 includes five cannulas 2105 which include four cannulas 2105 labeled 1-4 configured to receive surgical tools and a fifth cannula 2105 labeled C configured to receive a camera. The robotic arm coupled to the camera may be configured to reposition the camera to obtain a perspective view of any portion of the patient's abdominal region in which the laparoscopic procedure is performed. Thus, in the embodiment of FIG. 21, it may not be necessary to perform camera hopping in order to obtain multiple perspectives for a surgery, as the camera itself can provide multiple perspective viewing via articulation.

Also illustrated in FIG. 21 are a number of anatomical quadrants, including the right upper quadrant (RUQ), left upper quadrant (LUQ), right lower quadrant (RLQ), and left lower quadrant (LLQ), and additionally the pelvic region. The general location of certain anatomical features including the hepatic flexure, splenic flexure, cecum, and sigmoid colon are illustrated, each which may be involved in a given laparoscopic procedure.

Figure 22A:
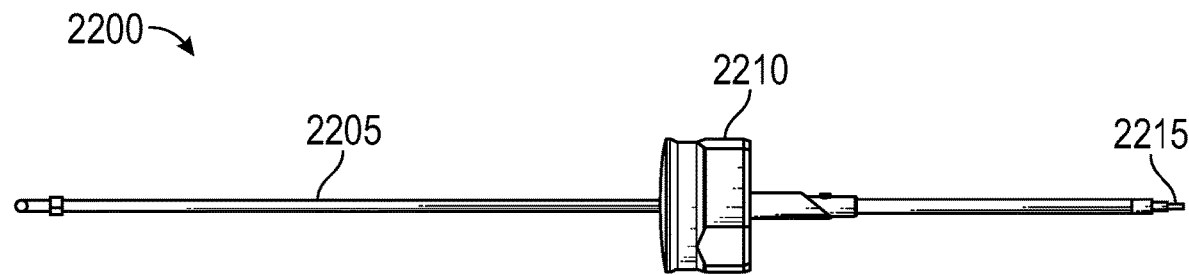
FIG. 22A is an example embodiment of a surgical tool which may be docked to a cannula in accordance with aspects of this disclosure.

As previously described, surgical tools may be docked to each of the cannulas 2105 labeled 1-4. FIG. 22A is an example embodiment of a surgical tool which may be docked to a cannula in accordance with aspects of this disclosure. As shown in FIG. 22A, the surgical tool or instrument 2200 includes a shaft 2205, a handle 2210, and an end effector 2215. The instrument 2200 may be attachable to one of the robotic arms at the handle 2210. The instrument may have a configuration that enables the shaft 2205, with the end effector 2215 at a distal end of the shaft 2205, to translate relative to the handle 2210 for insertion into the patient's anatomy. The instrument 2200 may be configured to be attached, via the handle 2210, to an active drive mechanism (ADM) formed at a distal end of the robotic arm.

The instrument 2200 may be capable of moving along an insertion axis via an instrument-based insertion architecture. Under an instrument-based insertion architecture, the architecture of the instrument allows it to move along an insertion axis, rather than having to rely primarily on a robotic arm, which therefore reduces swing mass of the system. In some embodiments, the instrument 2200 having instrument-based insertion architecture comprises a pulley architecture (not illustrated) which allows the shaft 2205 to translate relative to the handle 2210. Example implementations of such a pulley system are described in U.S. Provisional Patent Application No. 62/597,385, filed on Dec. 11, 2017, and in U.S. patent application Ser. No. 16/215,208, filed Dec. 10, 2018, issued as U.S. Pat. No. 10,470,830 on Nov. 12, 2019, each of which is herein incorporated by reference in its entirety.

In certain robotic systems, the insertion of a surgical tool or instrument may be performed via the movement of the distal end of the robotic arm (e.g., via the ADM). This may include a displacement of the ADM by a distance that is substantially equal to the insertion depth. This displacement of the ADM can result in a relatively large swung mass of the robot arm, which may lead to potential for collision between adjacent arms. In contrast, by using the instrument-based pulley insertion architecture as described herein, the robotic arms can advantageously be confined within a much smaller profile than the displacement methodology, thereby allowing the robotic arms to be docked to cannulas in multiple quadrants with a reduced risk of collision.

Figure 22B:
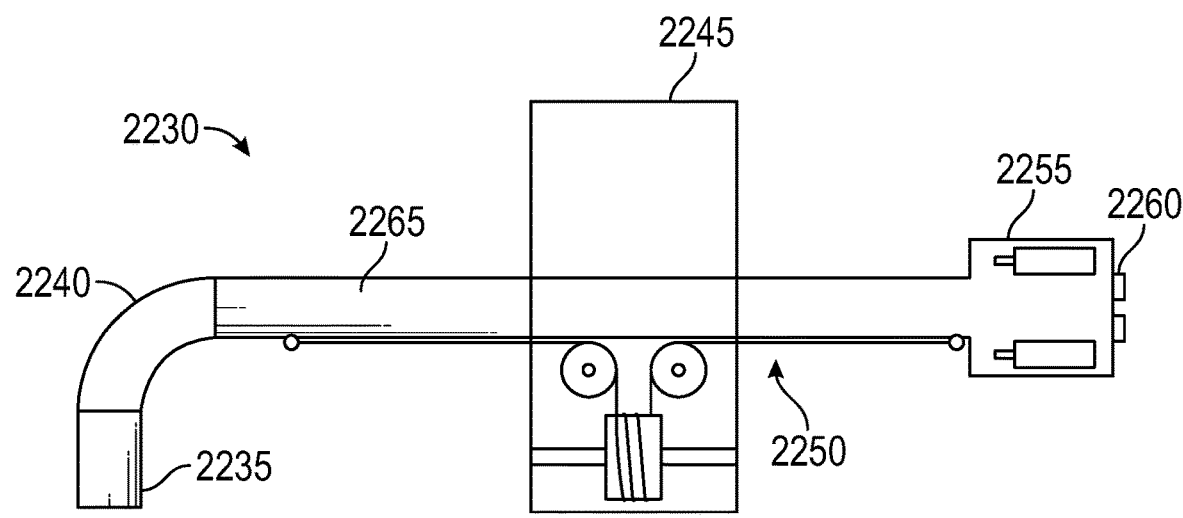
FIG. 22B is an example embodiment of an articulatable camera which may be docked to a cannula in accordance with aspects of this disclosure.

FIG. 22B is an example embodiment of an articulatable camera which may be docked to a cannula in accordance with aspects of this disclosure. As shown in FIG. 22B, the scope/camera (also referred to as an articulatable camera/scope) 2230 includes an articulatable scope tip 2235, an articulating section 2240 (also generally referred to as a snake wrist), a first handle 2245, an insertion cable 2250, a second handle 2255, and connections for light and camera 2260. The scope tip 2235 may include a camera (not illustrated) which is configured to receive images to provide a perspective view of an anatomical location. The scope tip 2235 may be articulated via the articulating section 2240 to set or adjust the view of the camera. Due to the inclusion of the articulating section 2240, the distal end of a shaft 2265 of the scope/camera is capable of articulation. The shaft 2265 extends through an upper surface and a lower surface of the first handle 2245.

The first handle 2245 may be configured to be couple to an ADM of a corresponding robotic arm and may include mechanical interface components which drive insertion of the scope tip 2235 based on forces applied thereto from the ADM. The scope/camera 2230 may include a similar pulley architecture discussed above in connection with the instrument 2200 capable of driving insertion of the scope tip 2235. Thus, the first handle 2245 may include one or more pulleys, cables and/or motors to assist in insertion of the scope tip 2235 into the patient. Additionally, the shaft 2265 may be capable of translating relative to the first handle 2245 as part of an instrument-based insertion architecture.

The second handle 2255 may be capable of attachment (e.g., via its backside) to a tower with a processor (not shown) that is designed to provide commands for the articulation of the scope tip 2235. The second handle 2255 may be coupled to a proximal portion of the shaft 2265. The second handle 2255 may include one or more motors that assist in articulation of the scope tip 2235. In other words, the scope/camera 2230 may include a first handle 2245 that assists in insertion of the scope tip 2235, while the second handle 3355 assists in articulation of the scope tip 2235. Advantageously, the design of the scope/camera 2230 enables instrument-based insertion architecture, thereby reducing the risk of collisions between robotic arms.

In some embodiments, the robotic system is capable of enabling multi-perspective surgery using an articulating camera. In some embodiments, multi-perspective surgery can include the ability to triangulate robotic laparoscopic instruments and a robotic laparoscope in multiple (e.g., two, three or four) quadrants of the abdomen, as well as the pelvis, with one set of five ports.

FIGS. 23A-27E show an exemplary colectomy surgery that can be performed in all four quadrants of the abdomen, as well as the pelvis, using one set of five ports or cannulas. The five cannulas can correspond to four instruments and one articulating camera, each of which remains docked to their respective port or cannula. Advantageously, each of the five robotic arms depicted can remain docked to their respective cannulas while using the articulating camera to view any of the quadrants. As shown in FIGS. 23A-23E, a physician can begin the colectomy surgery by articulating a camera to view the splenic flexure in a left upper quadrant of a patient. As shown in FIGS. 24A-24E, the physician can then articulate the camera to view the hepatic flexure in a right upper quadrant of a patient. As shown in FIGS. 25A-25E, the physician can then articulate the camera to view the cecum in the right lower quadrant. As shown in FIGS. 26A-26E, the physician can then articulate the camera to view the sigmoid colon in the left lower quadrant. As shown in FIGS. 27A-27E, the physician can then articulate the camera to view the pelvic region as part of the colectomy surgery. Notably, throughout each of the steps of the colectomy in FIGS. 23A-27E, each of the robotic arms can remain docked to their respective cannulas while simply adjusting the articulating camera to achieve multiple perspective viewing. Other robotic systems are simply not capable of achieving such multiple perspective viewing with such ease.

By providing an articulating scope or camera, a physician is advantageously capable of viewing multiple perspectives through a single port or cannula. FIGS. 23A-27E provide a plurality of views of a surgical robotic system arranged for an example colectomy surgery, which may be performed in each of the four abdominal quadrants using such an articulating camera through a single port or cannula. As explained in further detail below, five views are shown in each of FIGS. 23A-23E, FIGS. 24A-24E, FIGS. 25A-25E, FIGS. 26A-26E and FIGS. 27A-27E: a front view of the bed (in which the side-to-side tilt can be seen in each of the figures); a top down view (which illustrates cannula placement); a top perspective view of the bed (from which the front-to-back tilt, or trendelenberg tilt can be seen); an internal view of a surgical site including an articulating scope with an articulating section; and a camera view (what a physician would see in first person from the camera). In FIGS. 23A-27E, each of the robotic arms (labelled "1-4") is capable of holding a tool or instrument, while the robotic arm (labelled "C") is capable of holding an articulating camera. Notably, the robotic arms remain docked to their respective cannulas in each of the set of figures (FIGS. 23A-23E, FIGS. 24A-24E, FIGS. 25A-25E, FIGS. 26A-26E and FIGS. 27A-27E), with the articulating camera free to view the different quadrants. In some embodiments, such multi-quadrant viewing using an articulating scope can be made easier due to the bilateral placement of the robotic arms, as well as by the instrument-based insertion architecture of the instrument, which reduces the risk of collisions between the robotic arms.

Figure 23A:
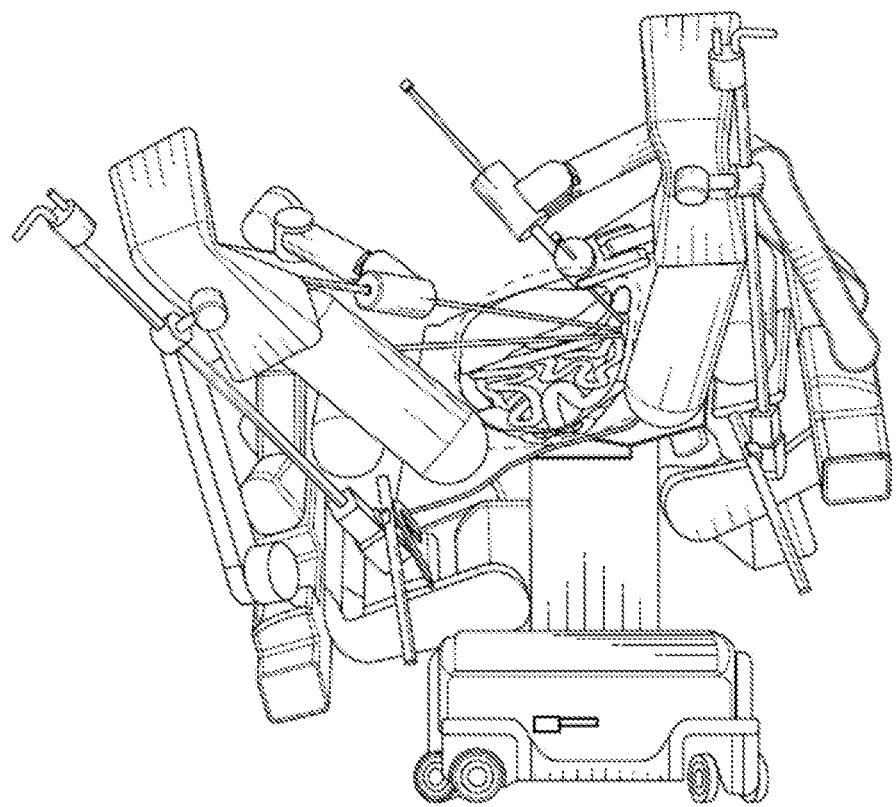
FIGS. 23A-23E illustrate example views of the arrangement of a surgical robotic system for a splenic flexure portion of an example colectomy surgery in accordance with aspects of this disclosure.
Figure 23B:
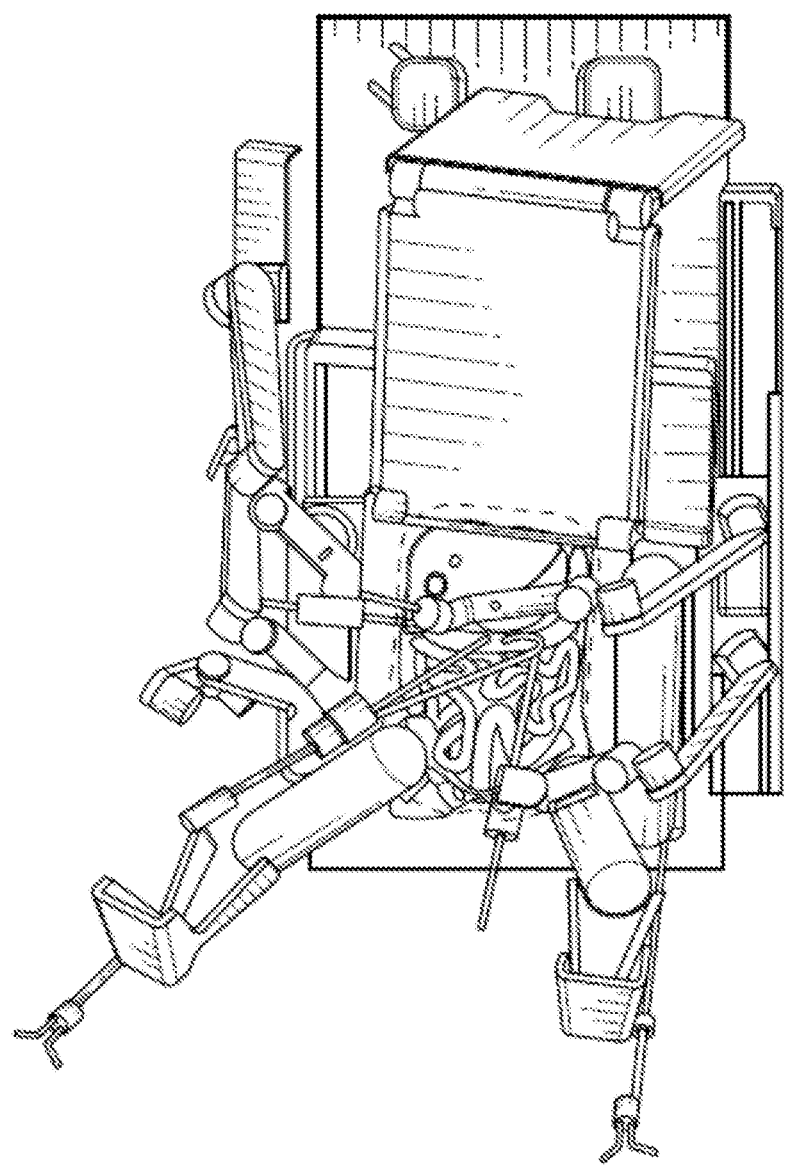
Figure 23C:
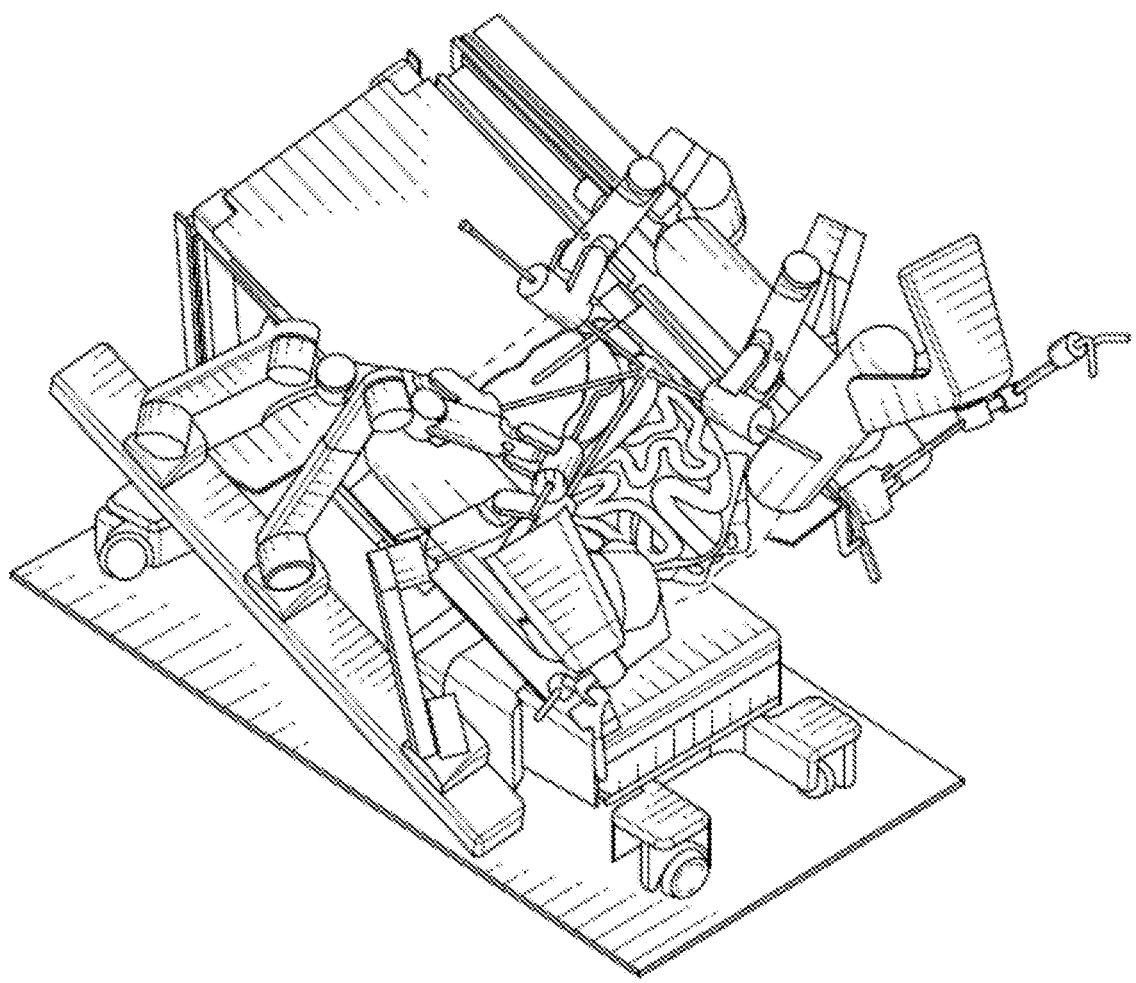
Figure 23D:
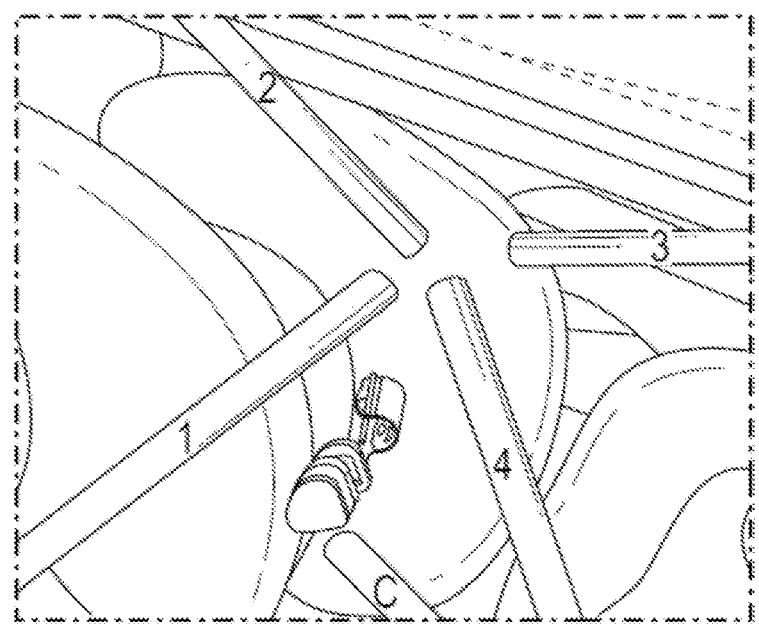
Figure 23E:
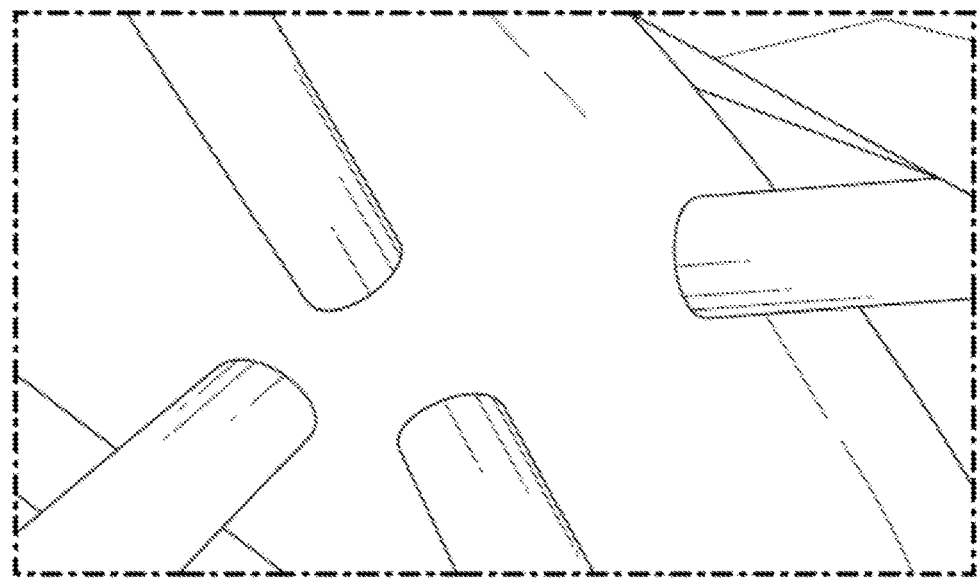

FIGS. 23A-23E illustrate example views of the arrangement of a surgical robotic system having an articulating camera for viewing a splenic flexure portion in a left upper quadrant of a patient as part of an example colectomy surgery in accordance with aspects of this disclosure. In more detail, FIGS. 23A-23C respectively illustrate a front view, a top down view, and a top perspective view of the bed arranged for the splenic flexure portion of the colectomy surgery. FIGS. 23D and 23E respectively illustrate an internal view of the surgical site and a camera view of the surgical site showing the view obtained by a repositionable and/or articulatable camera for the splenic flexure portion of the colectomy surgery.

Figure 24A:
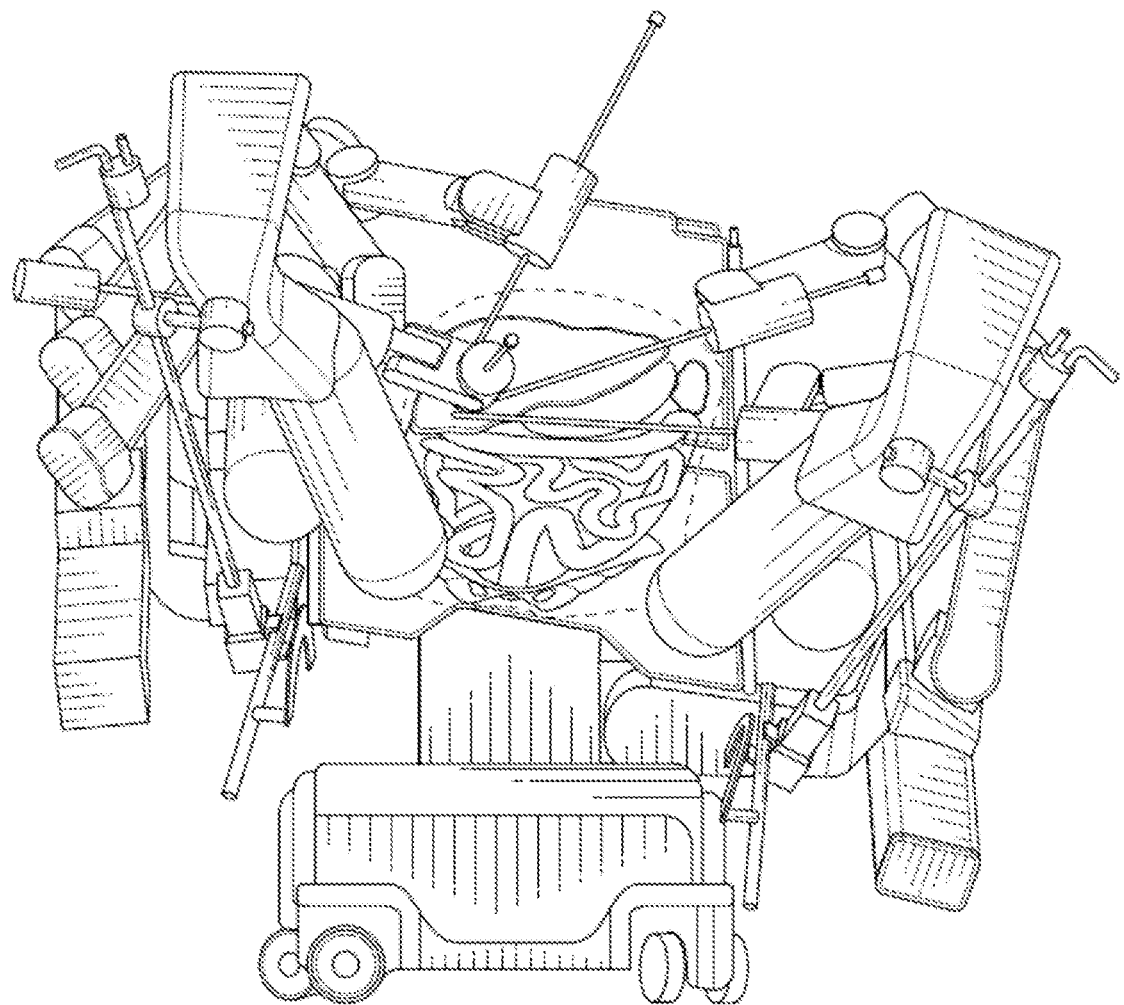
FIGS. 24A-24E illustrate example views of the arrangement of a surgical robotic system for a hepatic flexure portion of an example colectomy surgery in accordance with aspects of this disclosure.
Figure 24B:
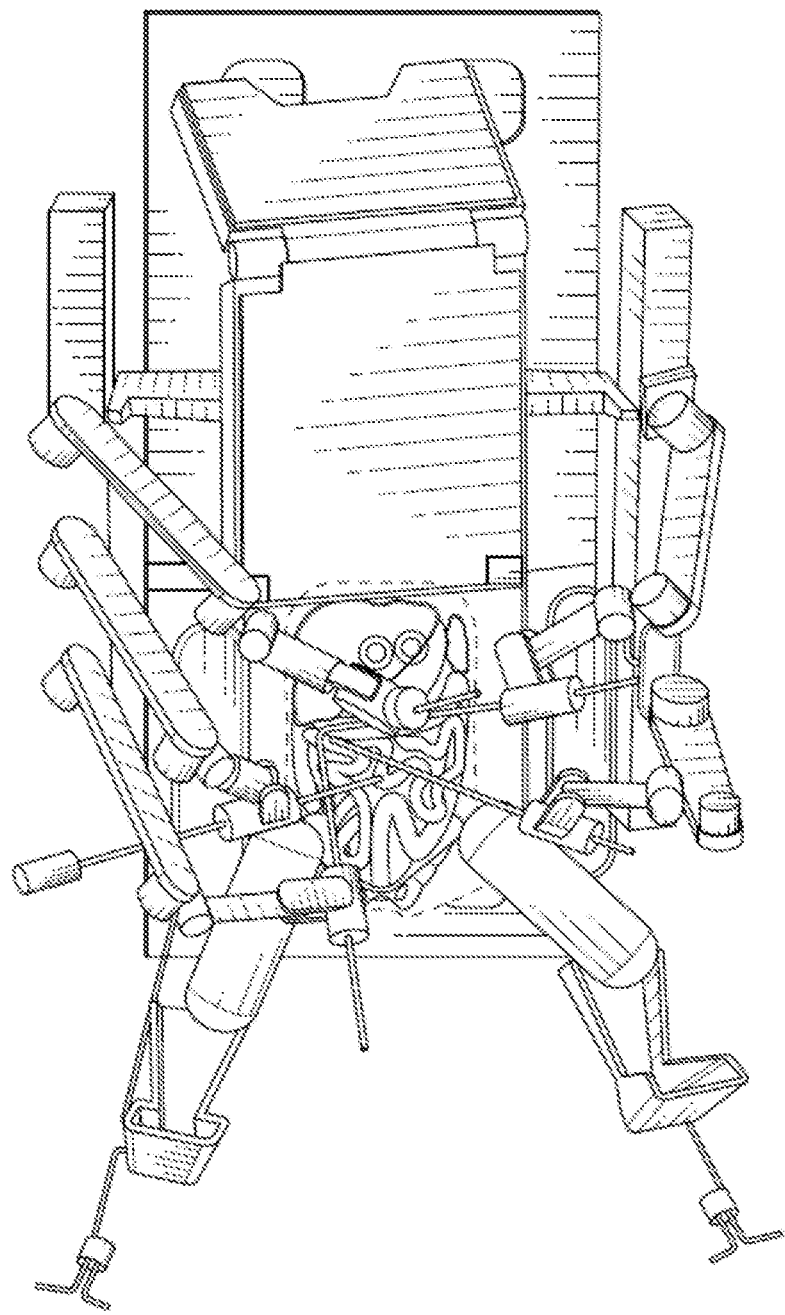
Figure 24C:
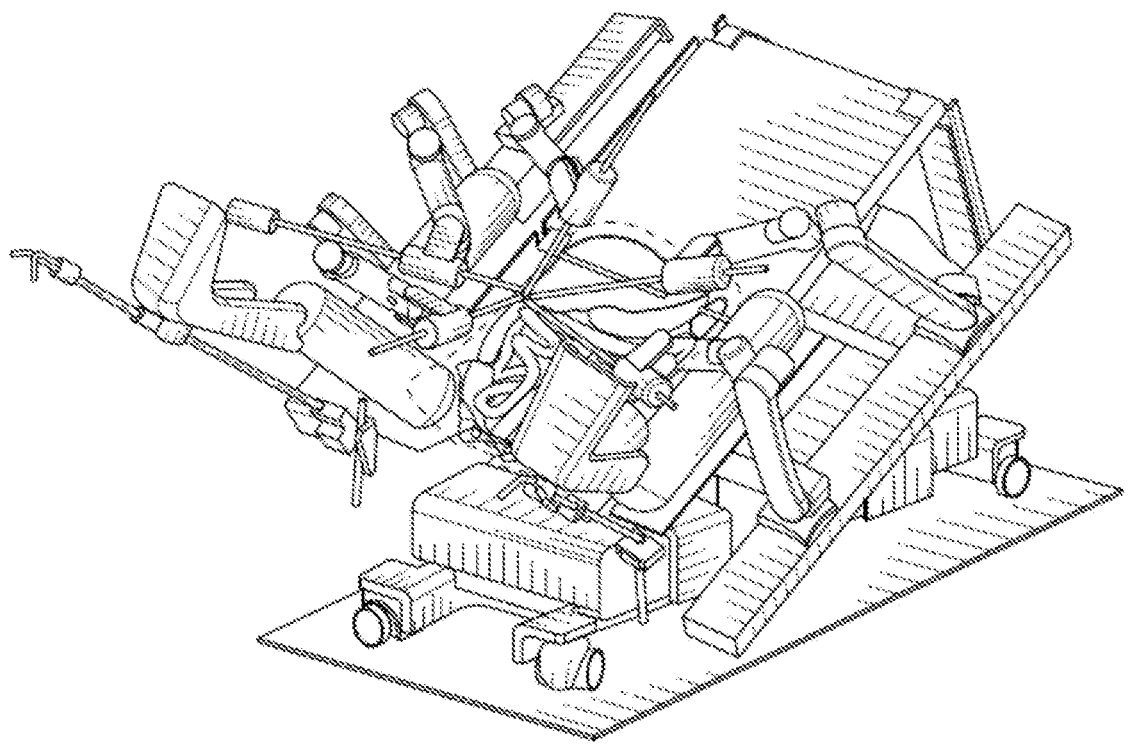
Figure 24D:
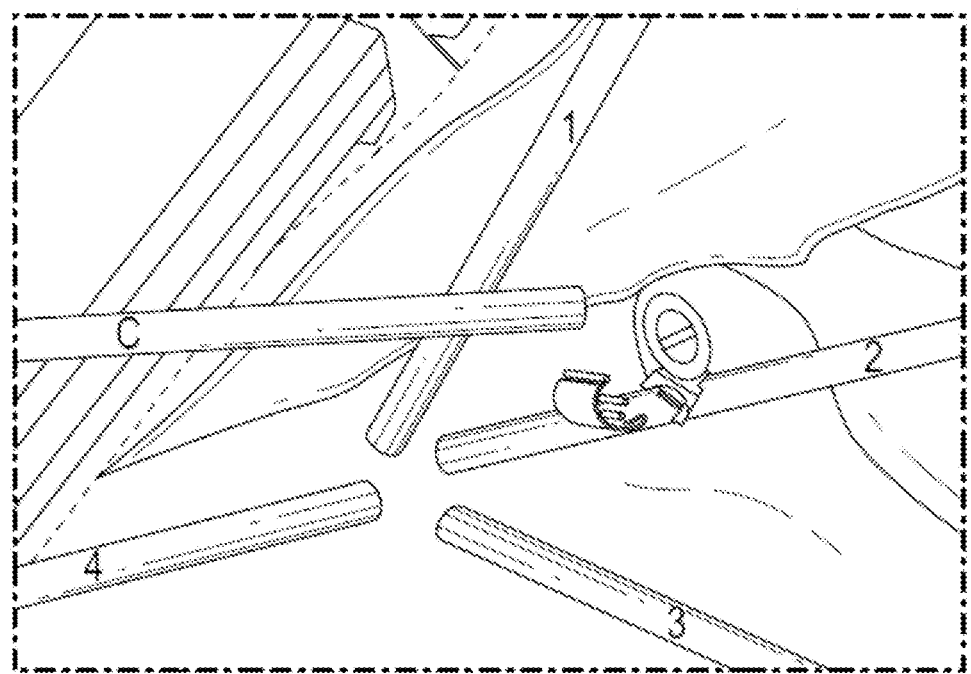
Figure 24E:
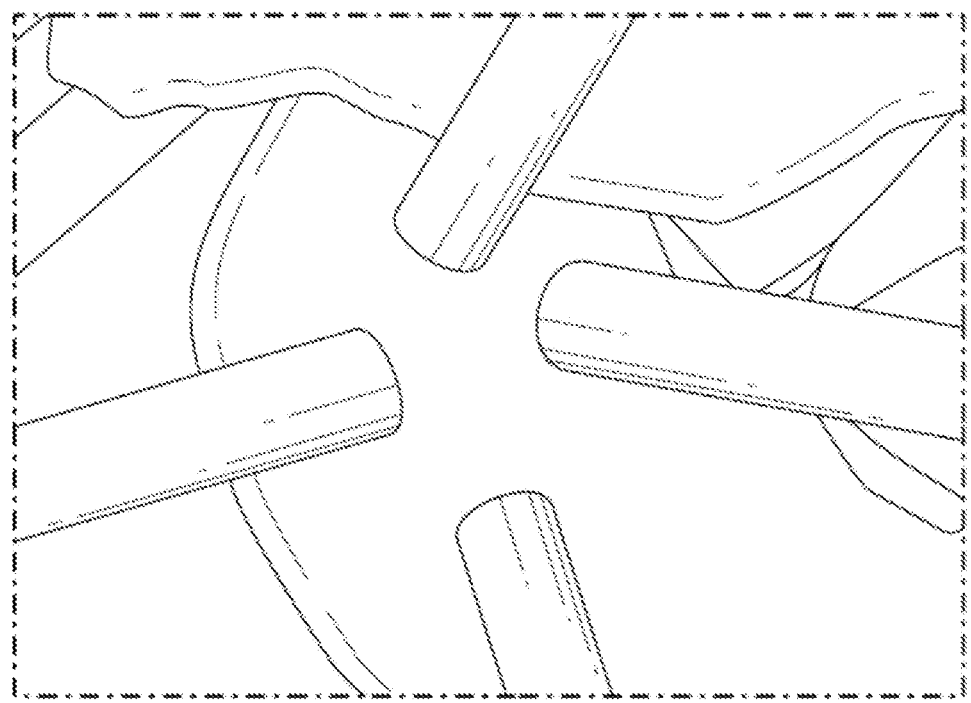

FIGS. 24A-24E illustrate example views of the arrangement of a surgical robotic system in which the articulating camera is adjusted to view a hepatic flexure portion in a right upper quadrant of the patient as part of the example colectomy surgery in accordance with aspects of this disclosure. In more detail, FIGS. 24A-24C respectively illustrate a front view, a top down view, and a top perspective view of the bed arranged for the hepatic flexure portion of the colectomy surgery. FIGS. 24D and 24E respectively illustrate an internal view of the surgical site and a camera view of the surgical site showing the view obtained by a repositionable and/or articulatable camera for the hepatic flexure portion of the colectomy surgery.

Figure 25A:
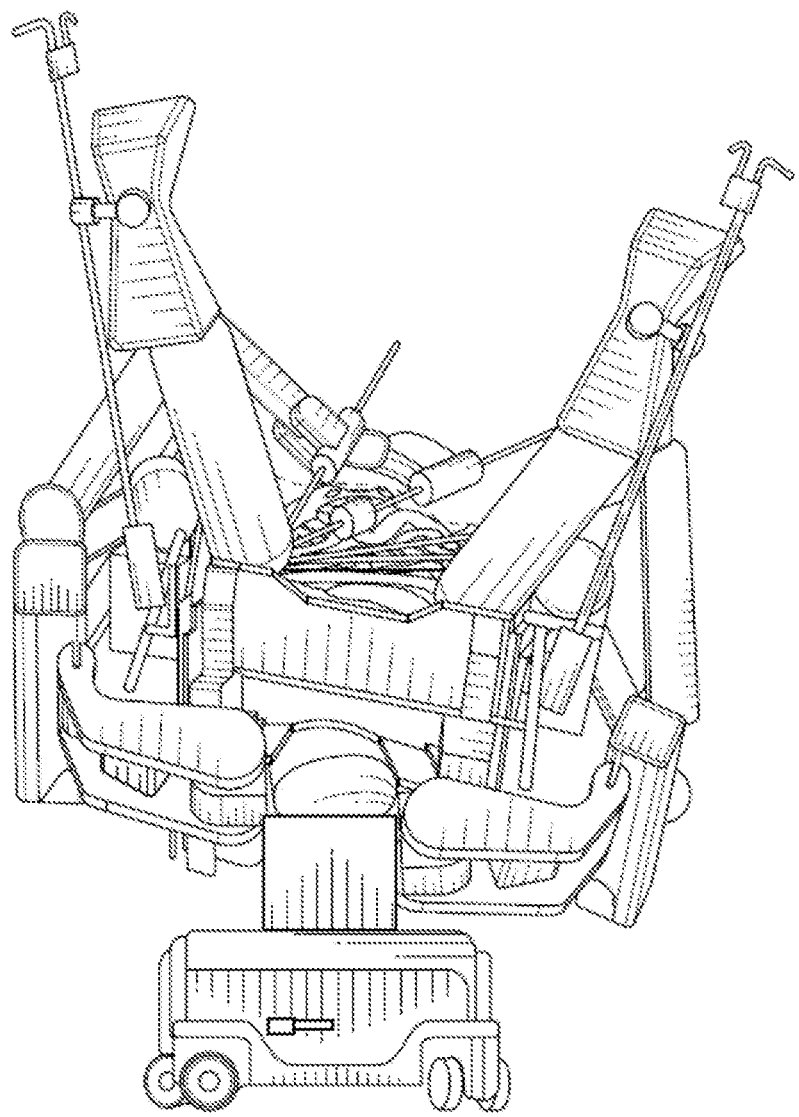
FIGS. 25A-25E illustrate example views of the arrangement of a surgical robotic system for a cecum portion of an example colectomy surgery in accordance with aspects of this disclosure.
Figure 25B:
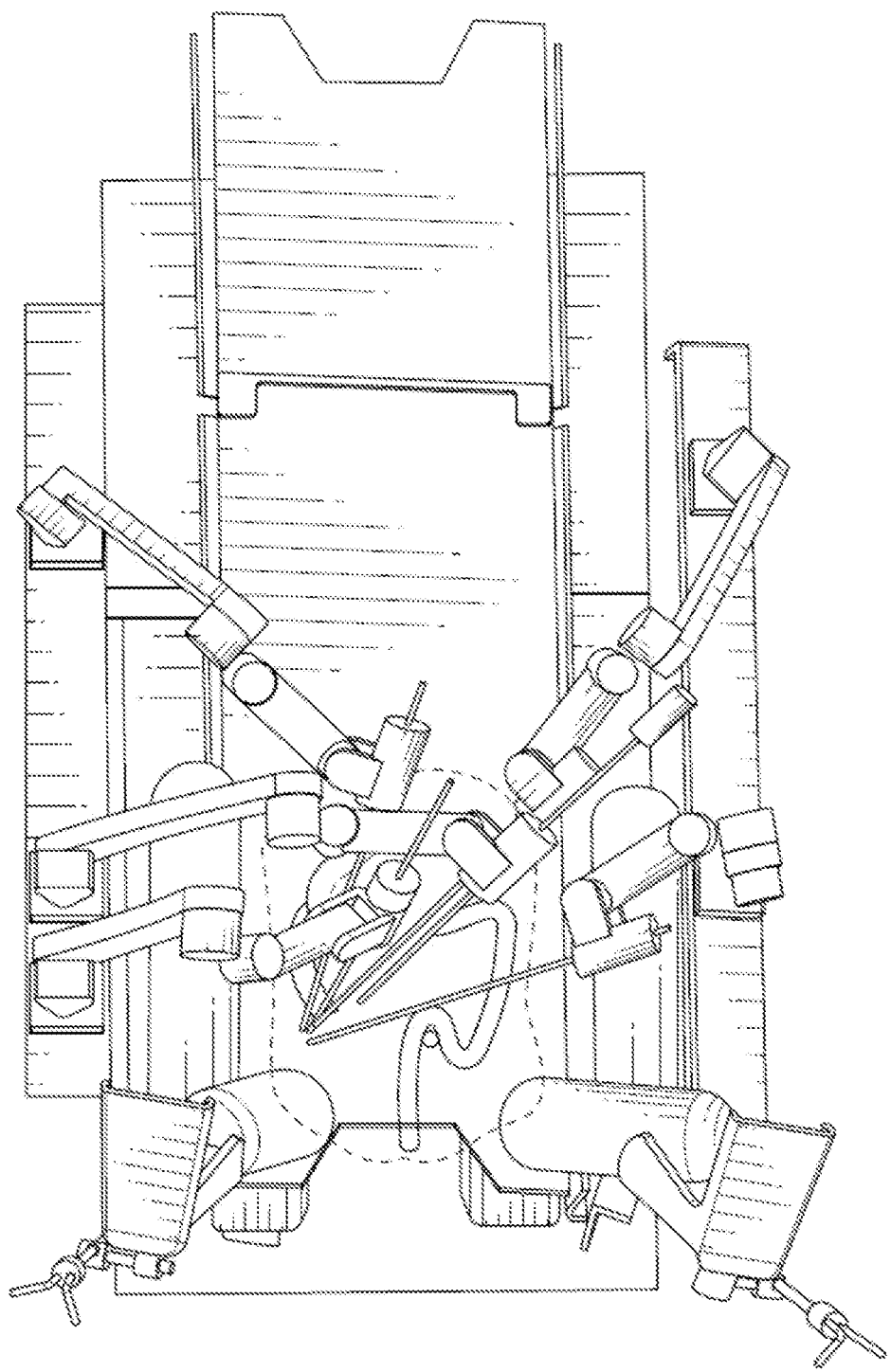
Figure 25C:
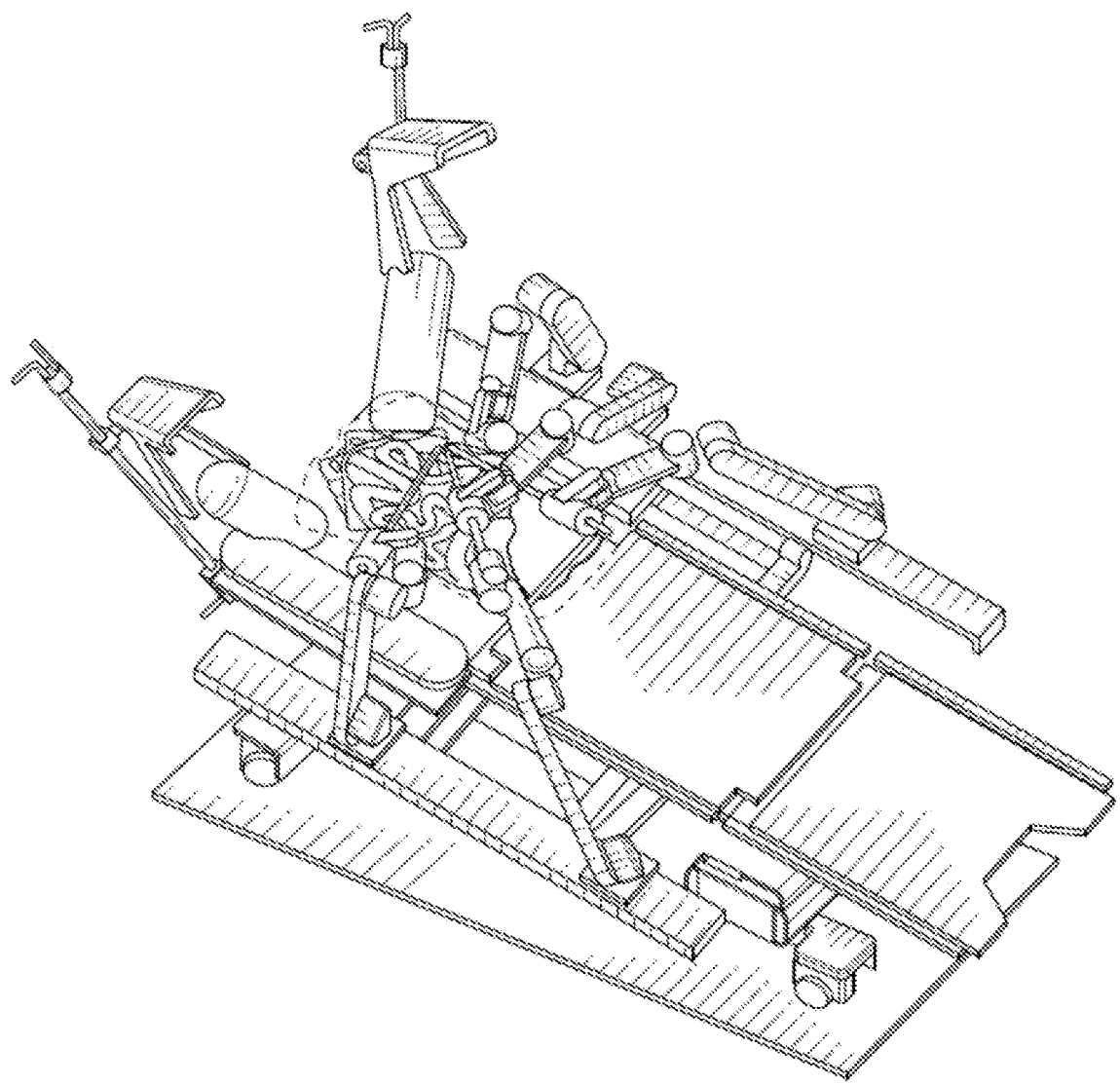
Figure 25D:
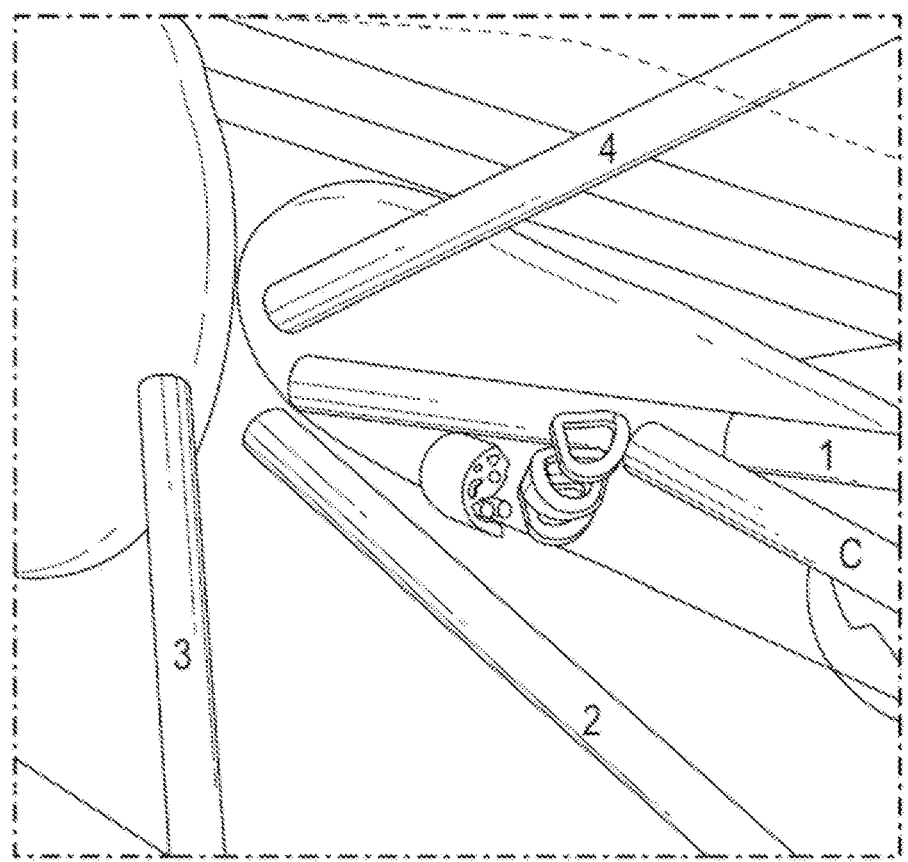
Figure 25E:
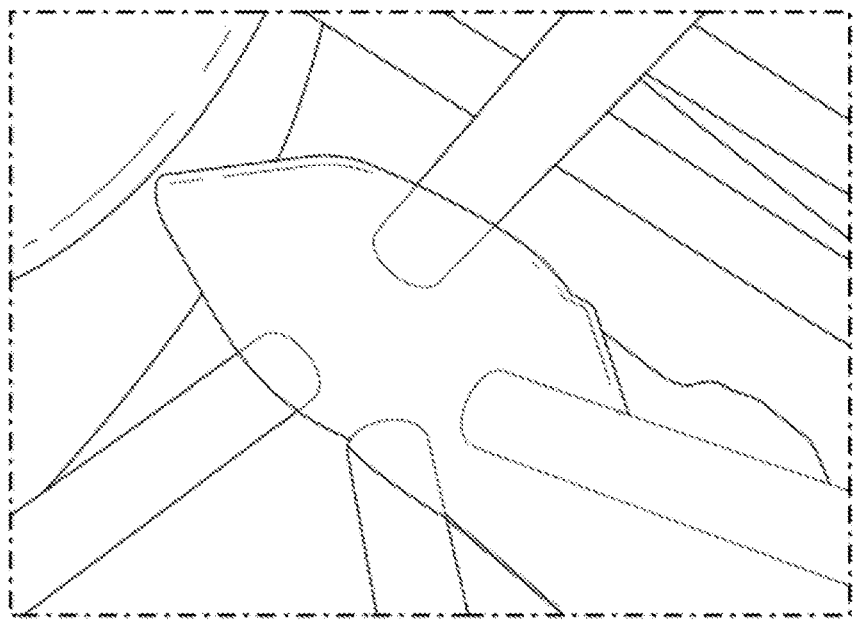

FIGS. 25A-25E illustrate example views of the arrangement of a surgical robotic system in which the articulating camera is adjusted to view a cecum portion in a right lower quadrant of the patient as part of the example colectomy surgery in accordance with aspects of this disclosure. In more detail, FIGS. 25A-25C respectively illustrate a front view, a top down view, and a top perspective view of the bed arranged for the cecum portion of the colectomy surgery. FIGS. 25D and 25E respectively illustrate an internal view of the surgical site and a camera view of the surgical site showing the view obtained by a repositionable and/or articulatable camera for the cecum portion of the colectomy surgery.

Figure 26A:
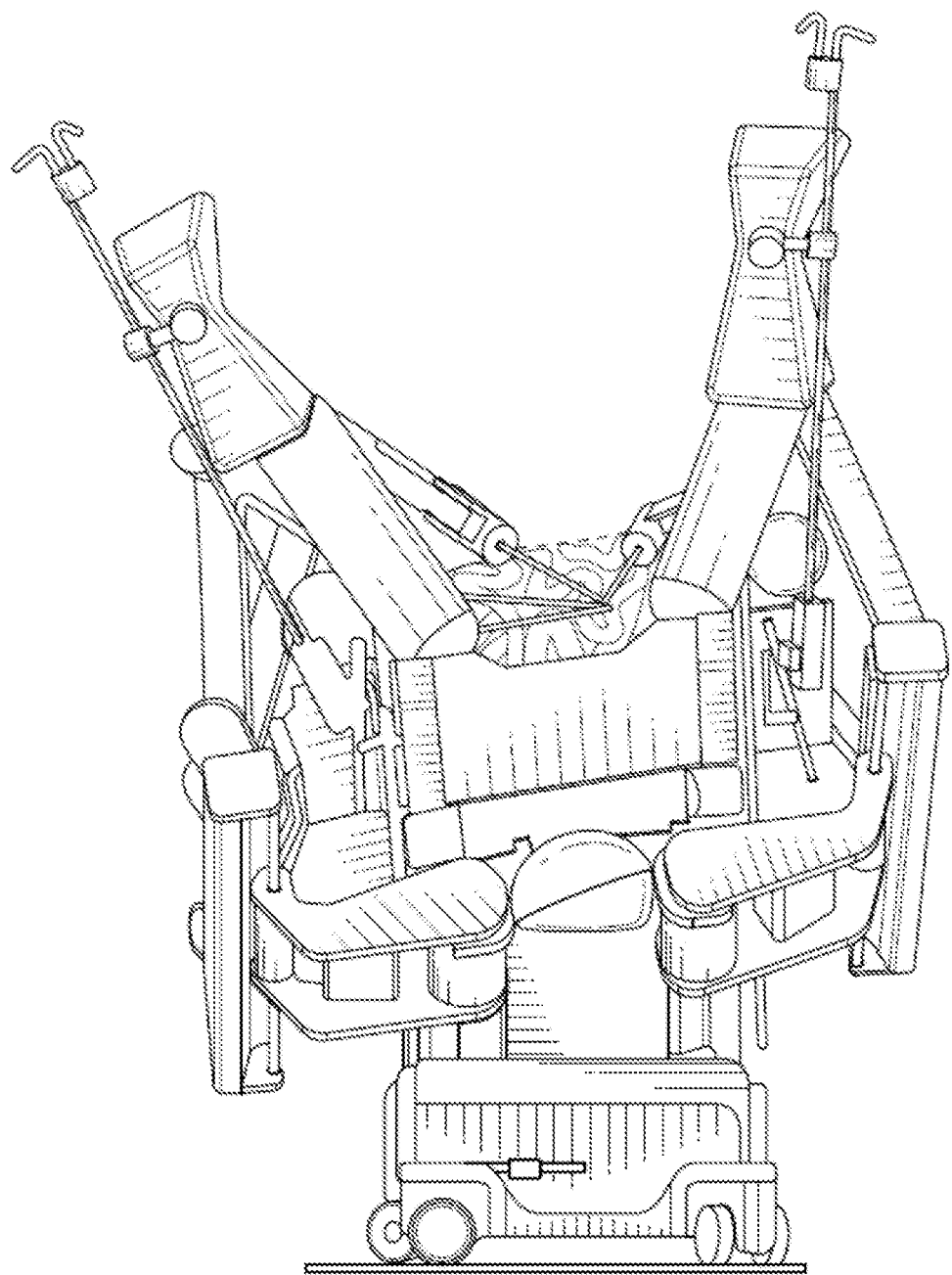
FIGS. 26A-26E illustrate example views of the arrangement of a surgical robotic system for a Sigmund portion of an example colectomy surgery in accordance with aspects of this disclosure.
Figure 26B:
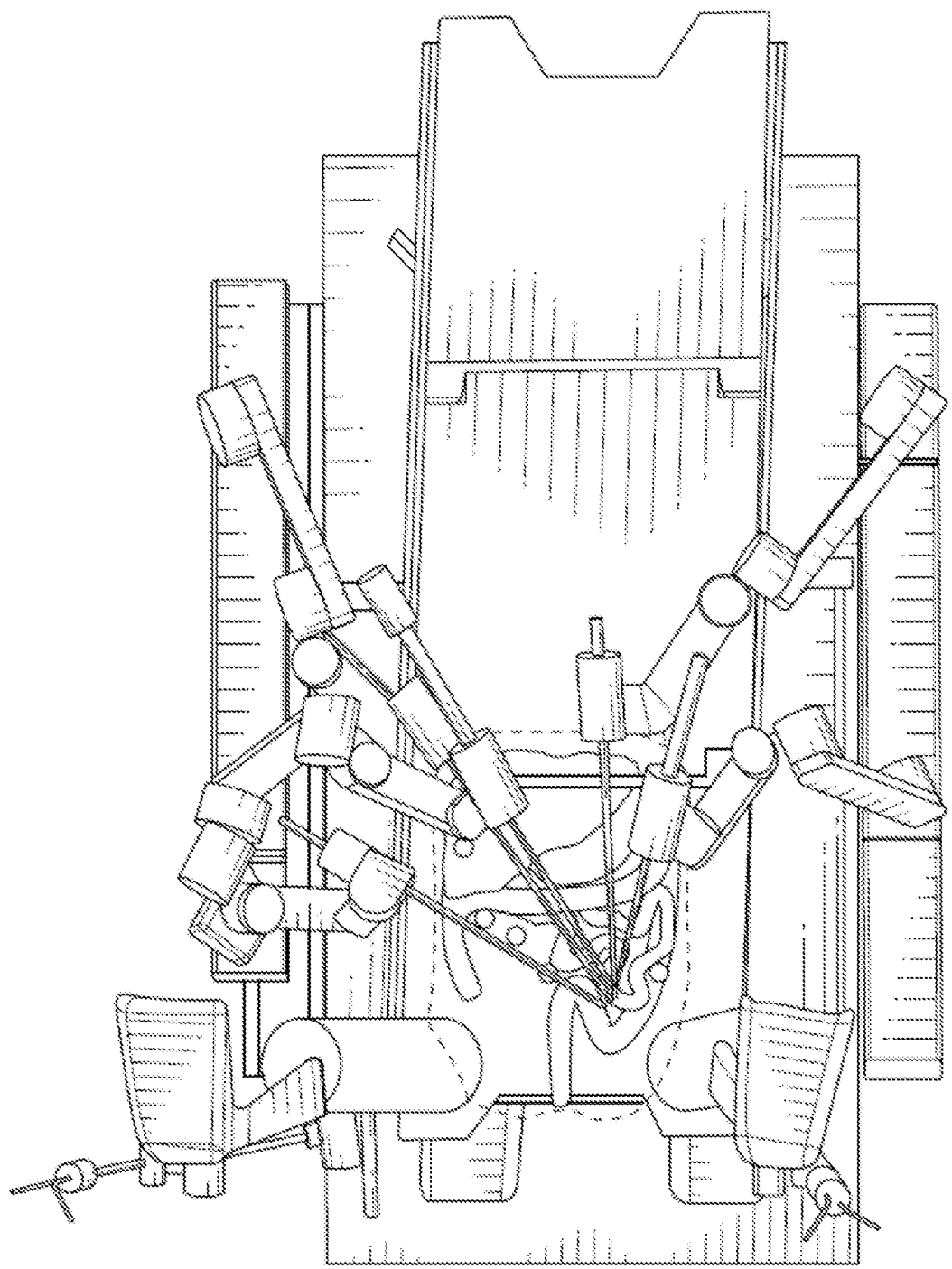
Figure 26C:
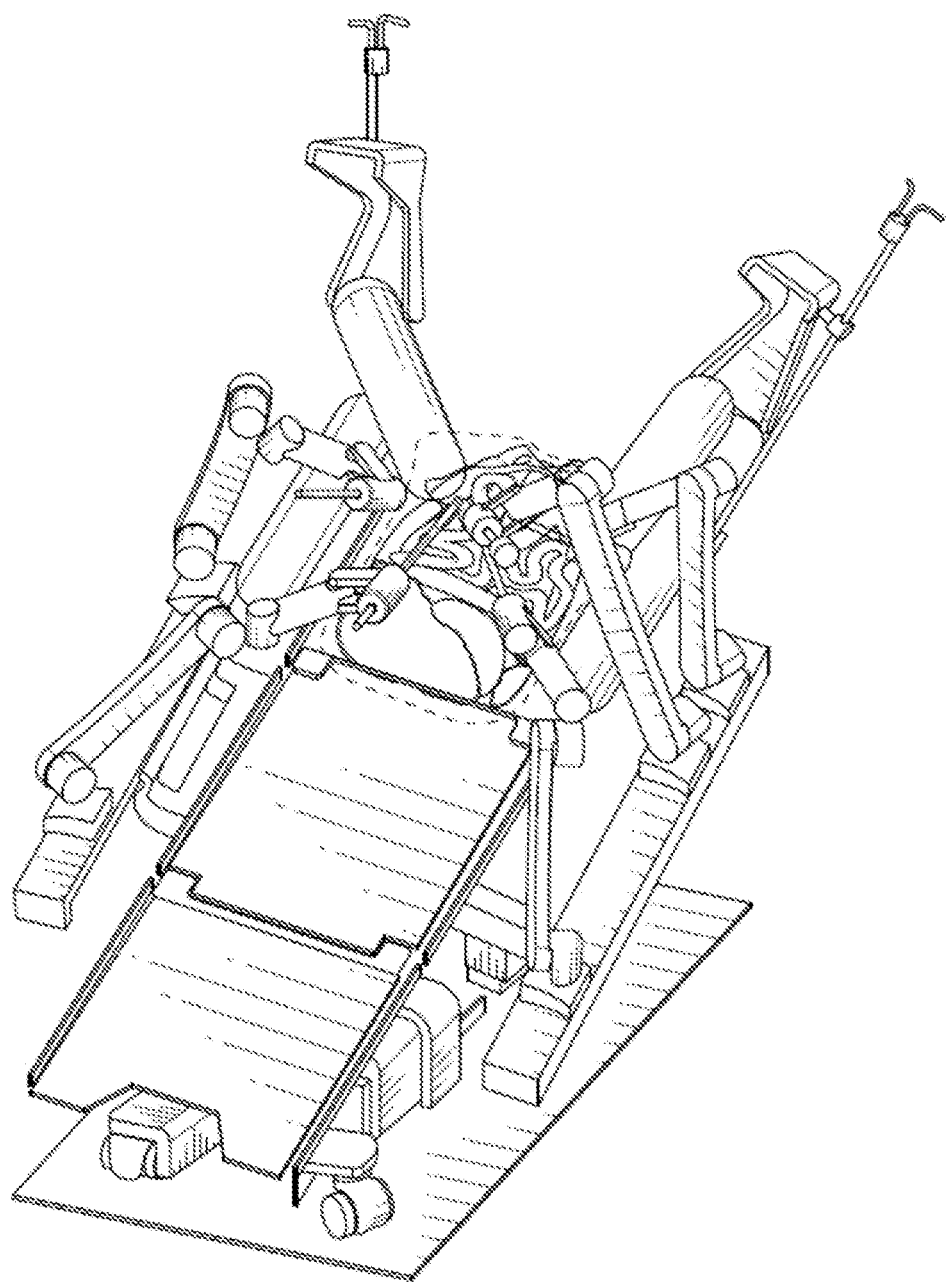
Figure 26D:
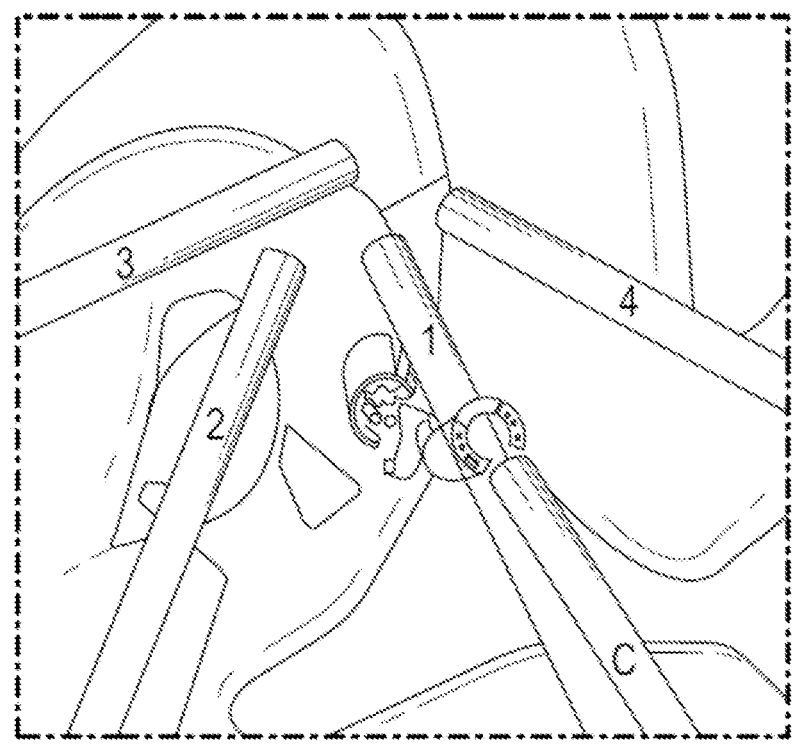
Figure 26E:
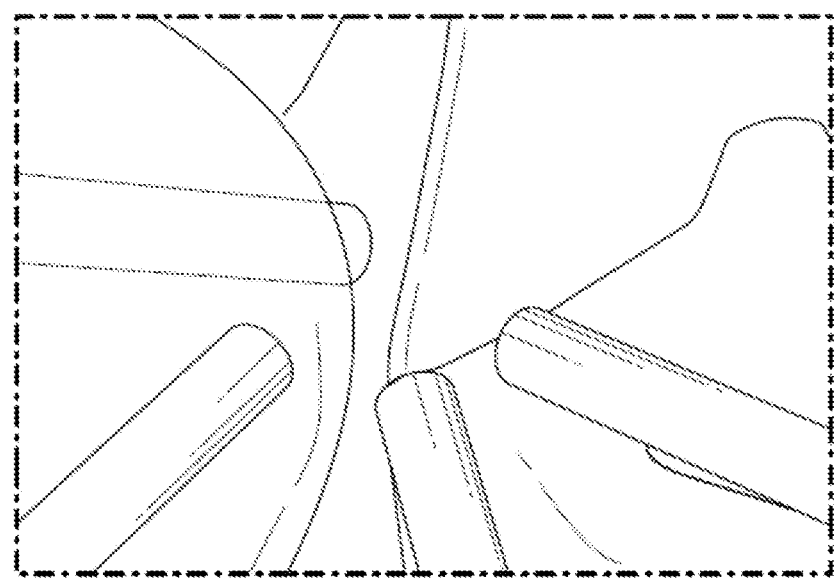

FIGS. 26A-26E illustrate example views of the arrangement of a surgical robotic system in which the articulating camera is adjusted to view a sigmund portion in a left lower quadrant of the patient as part of the example colectomy surgery in accordance with aspects of this disclosure. In more detail, FIGS. 26A-26C respectively illustrate a front view, a top down view, and a top perspective view of the bed arranged for the sigmund portion of the colectomy surgery. FIGS. 26D and 26E respectively illustrate an internal view of the surgical site and a camera view of the surgical site showing the view obtained by a repositionable and/or articulatable camera for the Sigmund portion of the colectomy surgery.

Figure 27A:
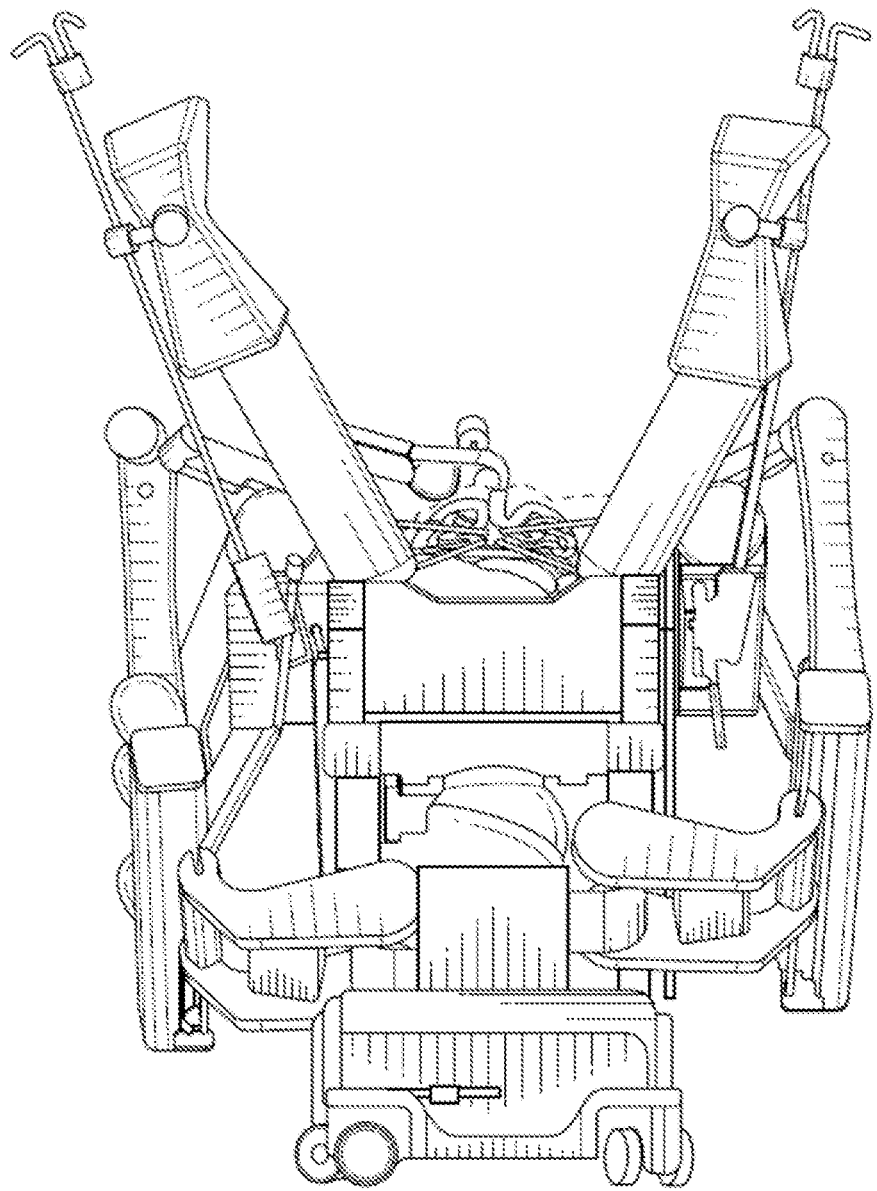
FIGS. 27A-27E illustrate example views of the arrangement of a surgical robotic system for a pelvic portion of an example colectomy surgery in accordance with aspects of this disclosure.
Figure 27B:
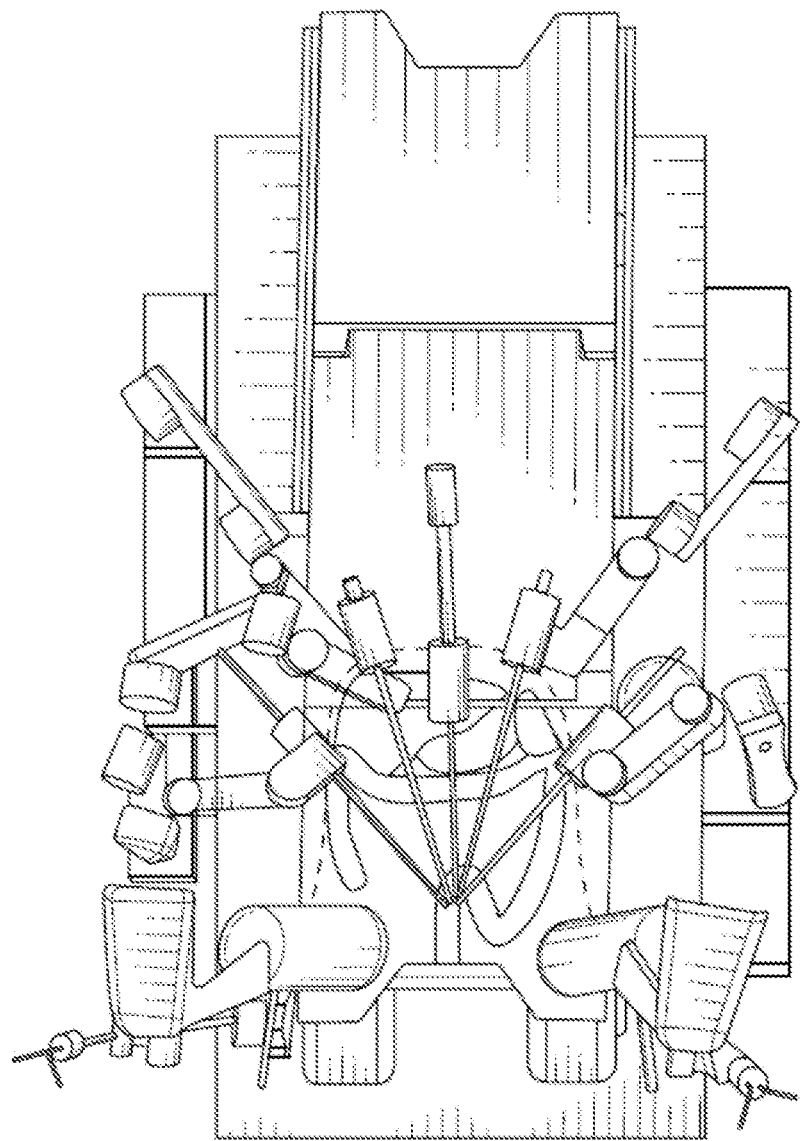
Figure 27C:
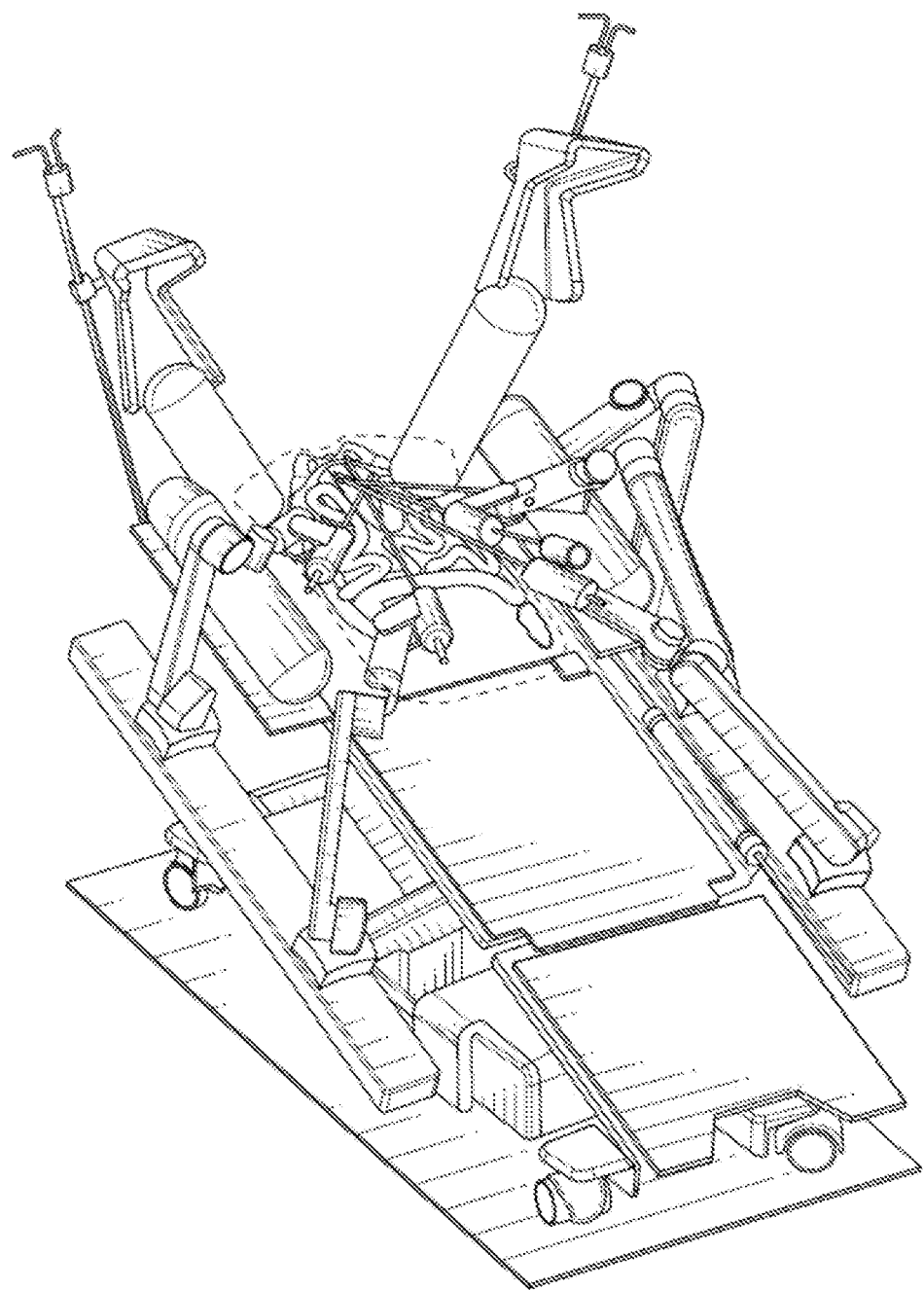
Figure 27D:
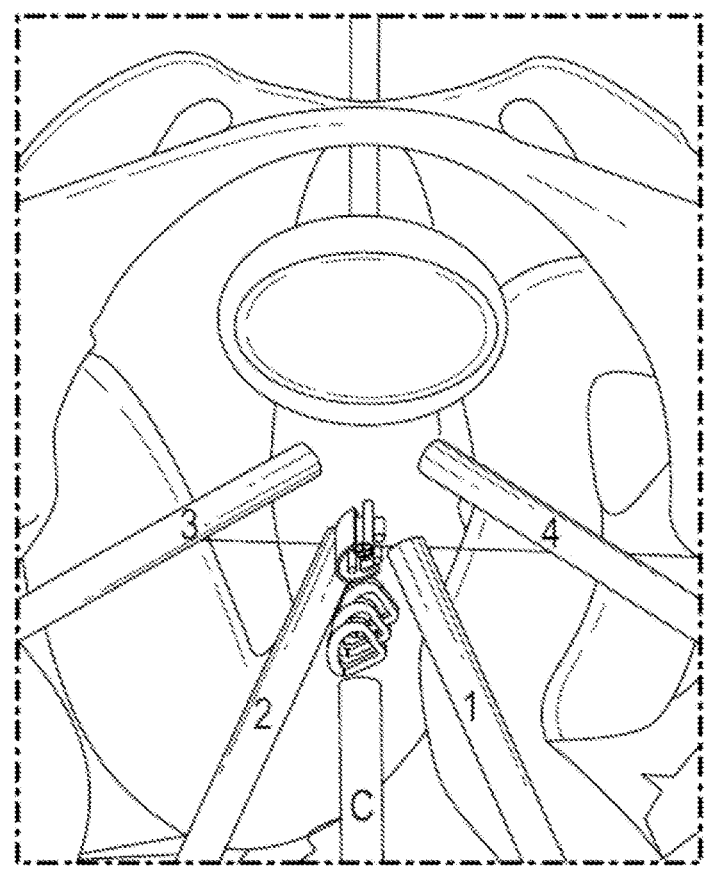
Figure 27E:
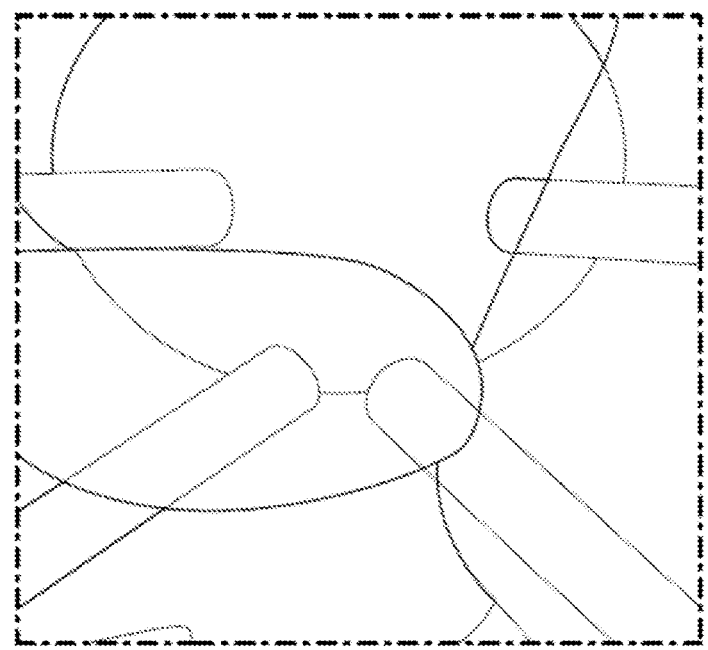

FIGS. 27A-27E illustrate example views of the arrangement of a surgical robotic system in which the articulating camera is adjusted to view a pelvic portion of the patient as part of the example colectomy surgery in accordance with aspects of this disclosure. In more detail, FIGS. 27A-27C respectively illustrate a front view, a top down view, and a top perspective view of the bed arranged for the pelvic portion of the colectomy surgery. FIGS. 27D and 27E respectively illustrate an internal view of the surgical site and a camera view of the surgical site showing the view obtained by a repositionable and/or articulatable camera for the pelvic portion of the colectomy surgery. The locations of the splenic flexure, hepatic flexure, cecum, sigmund, and pelvic surgical sites can also be seen from the illustration in FIG. 21.

This disclosure provides a number of different embodiments for the articulatable scope tip 2235 which can provide the multiple surgical views via the central cannula labeled C in each of FIGS. 21 and 23A-27E. FIGS. 28A-28H illustrate a number of different repositionable or articulatable scopes/cameras in accordance with aspects of this disclosure.

Figure 28A:
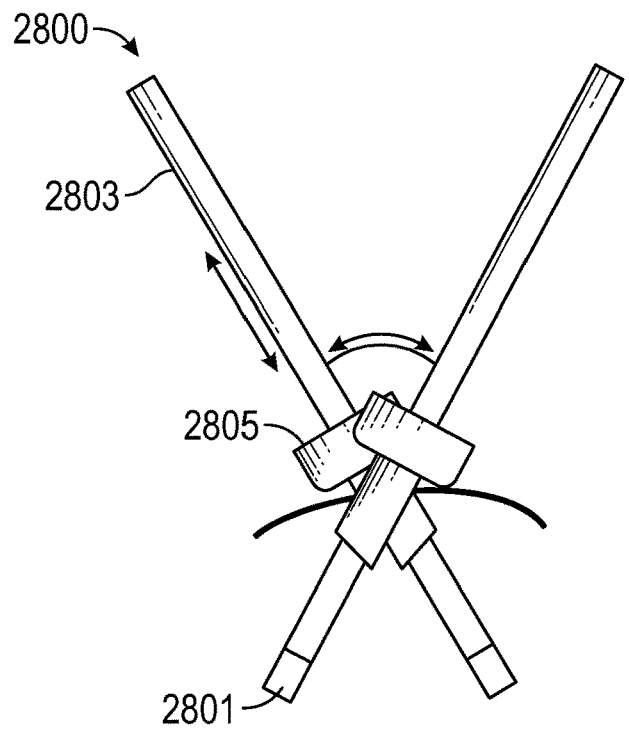
FIGS. 28A-28H illustrate a number of different repositionable or articulatable camera scopes in accordance with aspects of this disclosure.

In the embodiment of FIG. 28A the repositionable camera 2800 is a rigid camera which does not include an articulatable scope tip. The camera 2800 includes a scope tip 2801 and a shaft 2803 which are docked to a cannula 2805. Since the camera 2800 does not articulate in this embodiment, insertion and movement of the camera 2800 may require displacement of the ADM of the robotic arm. In the embodiment of FIG. 28A, there is no articulation in the shaft 2803 or distal end 2801, and thus the rigid scope may have to be moved or "camera hop" to different locations to enable multiple perspectives. One overall benefit of this embodiment is that the rigid scope is cheaper to manufacture than an articulatable camera.

To gain additional perspective, the camera 2800 may be moved between different port locations and a new coordinate frame may be established from location to location. The camera may be the same size diameter as surgical tools or instruments to allow the devices to be used interchangeably through the same cannulas 2801.

Figure 28B:
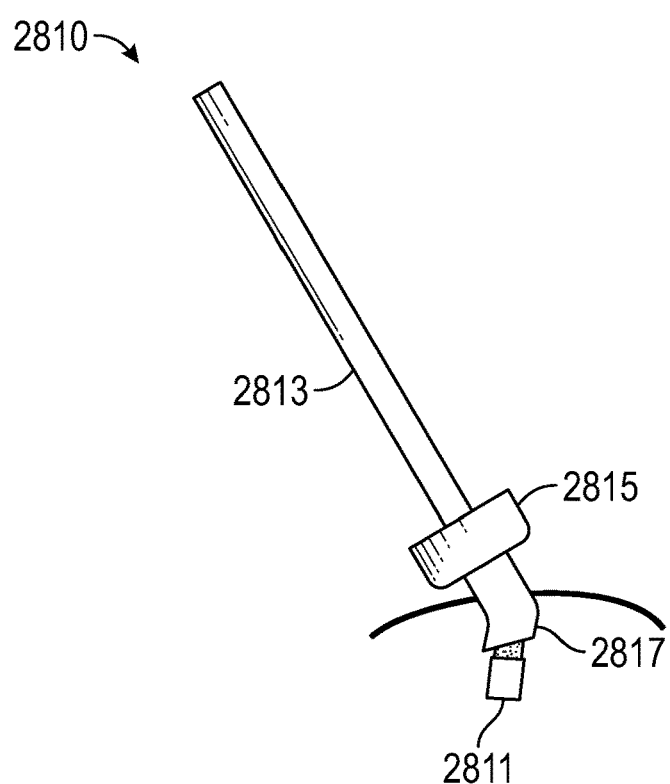

FIG. 28B illustrates an embodiment of a single articulation camera 2810 coupled with a flexible cannula 2815. The single articulation camera 2810 includes a distal end 2811 coupled to a shaft 2813 via an articulating section 2817. By articulating the camera 2810 via the articulating section 2817, the single articulation camera 2810 may provide enhanced perspective throughout a surgical procedure. Since the cannula 2815 is flexible, the physician may articulate the scope tip 2811 at any time without the robotic arm damaging the camera 2810, the cannula 2815 or the patient.

In one embodiment, the articulating camera may provide the only image sensor for the system. In another embodiment, the cannula may include a second imaging sensor (not illustrated) which enables a "gods-eye" view of the operative field. The gods-eye view can also be provided via model-based 3D virtual reality reconstruction without additional camera or hardware. The kinematic information used for robot control, combined with a patient model can be used to generate the virtual reality reconstruction. The patient model for the 3D virtual reality reconstruction, which can be based on estimated patient information, can be compared to a real environment inside the patient, and can adjust the size and location to find the best fit of all cannula port selection. In contrast to a fixed camera's view, the virtual reconstruction view can be generated for an arbitrary view point, arbitrary angle, and arbitrary zoom for maximum flexibility to user.

While the camera is not flexed and in a neutral position, in one embodiment, when the camera is articulated in any form or fashion, the robotic system compensates by recalculating a new coordinate frame to provide instinctive camera control and instrument motion. The camera can be inserted, retracted, pitched, and yawed in similar fashion to other surgical tools or instrument. The system may allow the physician to toggle into a camera control mode, in which the physician can uses his or her left and right hand interfaces to manipulate the image, thereby controlling the camera. By moving the control interfaces up, the image is can be panned up. Conversely, by moving the control interfaces down, the image can be panned down. Panning left and right can also be achieved by moving the control interfaces left and right, respectively. By articulating either the left hand or right hand control interface (which can be determined by system settings) in a leftward fashion, the camera can be articulated leftward, when a hand interface is articulated rightward, the camera can be articulated rightward, and so on for all other directions. The system may also enable commanding a neutral camera tip position in response to the articulation of the left and the right interfaces either away from or toward one another and the camera returns to neutral articulation. Additional detail regarding the control interface is provided below.

In another embodiment, the controls may be similar to those described above, except the articulation may be in response to both hand interfaces being articulated in the same direction. The articulation-based movements may or may not be constrained by haptic feedback.

In yet another embodiment, a second imaging sensor located near the cannula may provide a gods-eye view. In this embodiment, the camera may be controlled as described above. Alternatively, the system may include three driving modes (an instrument driving mode, and two camera driving modes). The first camera driving mode may function like the above described control for a rigid camera. To command articulation, the physician may select the second camera drive mode via a hand, foot, or other control toggle input. In the second camera drive mode, the gods-eye view may be displayed as the primary image. The image from the single articulation camera 2810 (also referred to as laparoscopic view) may be displayed as a secondary image via picture-in-picture or other means. The single articulation camera 2810 articulation can be controlled by using one of more of the left and right hand interfaces. The physician can thus utilize the gods-eye view and the laparoscopic view simultaneously to contextualize the camera location within the body cavity relative to the operative view(s). When articulation is complete, the physician may toggle back to either the instrument or first camera drive mode.

Figure 28C:
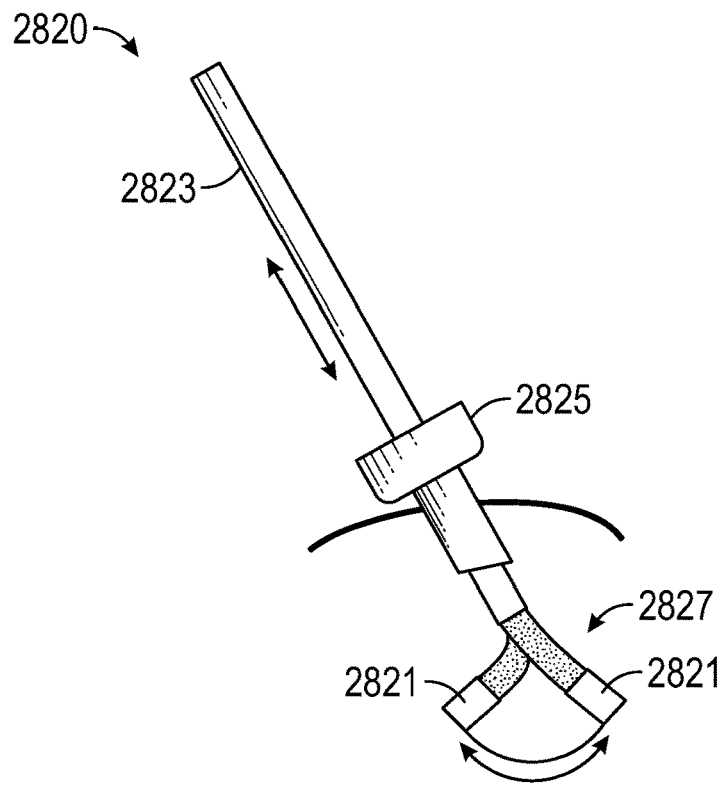

FIG. 28C illustrates an embodiment of a single articulation camera 2820 coupled with a rigid cannula 2825. The single articulation camera 2820 includes a distal end 2821 coupled to a shaft 2823 via an articulating section 2827. By articulating the camera 2820 via the articulating section 2827, the single articulation camera 2820 may provide enhanced perspective throughout a surgical procedure. Since the cannula 2825 of the FIG. 28C embodiment is rigid and does not bend with articulation of the single articulation camera 2820, at least a portion of the articulating section 2827 must be inserted past the end of the rigid cannula 2825 to articulate the distal end 2821 of the single articulation camera 2820.

The cannula for the single articulation camera 2820 may be placed in a position in accordance with the arrangement illustrated in FIG. 21. The physician may be able to use the articulation of the single articulation camera 2820 to provide a perspective view of the at least a portion of an anatomical region, such as a surgical target, a surgical site, and/or a general focal point throughout a surgical procedure. Although the embodiments disclosed herein may refer to providing a perspective view of a surgical site, those skilled in the art will recognize that a system configured to provide a perspective view of a surgical site may also be modified provide a perspective view of another anatomical region including a surgical target and/or general focal point, unless limited specifically by the context of the embodiment.

Since the cannula 2835 in the FIG. 28C embodiment is rigid, the physician may only be able to articulate the single articulation camera 2820 once the entirety of the articulating section 2831 (e.g., snake wrist) is distal to the cannula 2835. The robotic system may be configured to disable articulation until at least a portion of the articulating section 2831 is inserted past the distal end of the cannula 2835. In the event that the distal end 2831 of the single articulation camera 2830 is articulated as it is removed from the cannula 2835, the system may also be configured to force relaxation of the articulation to a neutral positing as the articulating section 2831 exits the cannula 2835.

In one embodiment, the single articulation camera 2830 may be the only image sensor which provides a perspective view of the surgical site for the system. In another embodiment, the cannula 2835 may include a second imaging sensor which enables a "gods-eye" view of the surgical site (e.g., operative field).

The single articulation camera 2820 of FIG. 28C may be controlled in a manner similar to the control techniques described in connection with FIG. 28B above.

Figure 28D:
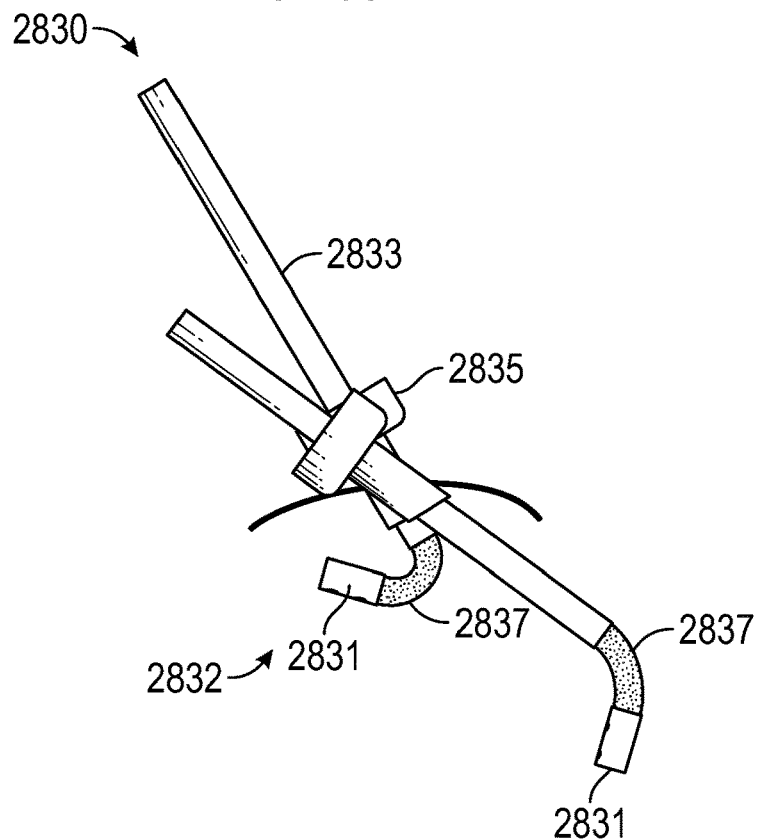

FIG. 28D illustrates another embodiment of a single articulation camera 2830. The single articulation camera 2830 includes a distal end 2831 coupled to a shaft 2833 via an articulating section 2837. The single articulation camera 2830 is configured to be docked to a cannula 2835, which may be rigid. The distal end 2831 may further include one or more imaging sensors 2832 located on a side of the distal end 2831. By utilizing the side-viewing imaging sensors 2832 which may be configured to provide a high-quality stereo image, the diameter of the distal end 2831 of the single articulation camera 2830 can be smaller than a 3D laparoscope of the related technology (e.g., the diameter of the distal end 2831 may be less than or equal to about 10 mm), thereby allowing for the use of a smaller cannula 2835.

In certain embodiments, the single articulation camera 2830 may not include a front-viewing image sensor, and thus, the single articulation camera 2830 may be inserted blindly until the device is sufficiently inserted through the cannula 2835, at which point the system may enable the user to articulate the single articulation camera 2830 to achieve a stereoscopic view and/or automate the articulation.

In another embodiment, the cannula 2835 may feature an additional imaging sensor to enable a gods-eye view of the operative field, thereby providing a view which may assist in insertion of the single articulation camera 2830 before a view can be obtained using the side-viewing imaging sensors 2832.

In yet another embodiment, this gods-eye view may be generated via model-based 3D virtual reality reconstruction without the inclusion of an additional camera or hardware. As previously discussed, the kinematic information used for robot control, combined with a patient model may be sufficient to generate the reconstruction. The patient model can adjust the size and location to best register with actual cannula port selections. This reconstructed view can have arbitrary view point, angle, and/or zoom to provide maximum flexibility to a physician.

In embodiments that feature a single or multi-side-viewing stereo cameras 2832 without a front-viewing camera, the single articulation camera 2830 may be articulated either by the physician or by the system once inserted through the cannula before an image of the surgical site can be obtained.

In embodiments which include the use of a single sided camera 2832, the physician may articulate the single articulation camera 2830 in a fashion similar to the embodiments outlined above. In another embodiment, the physician may experience similar controls, but can utilize hand gestures to articulate the camera slightly to enhance perspective throughout a medical procedure.

In embodiments which employ multi-sided stereoscopic cameras 2832, the physician may select his or her primary view using a hand-switch, foot-switch, or other input interface device. The secondary view may be hidden, displayed sequentially in a picture-in-picture format, and/or displayed as a series of images through which the physician can cycle using the input interface.

The system may also be configured to stitch together images received from multi-sided sensors 2832. Rather than articulating the single articulation camera 2830, the system may feature a drive mode whereby the physician utilizes hand interfaces to tilt or pan around the stitched images.

Figure 28E:
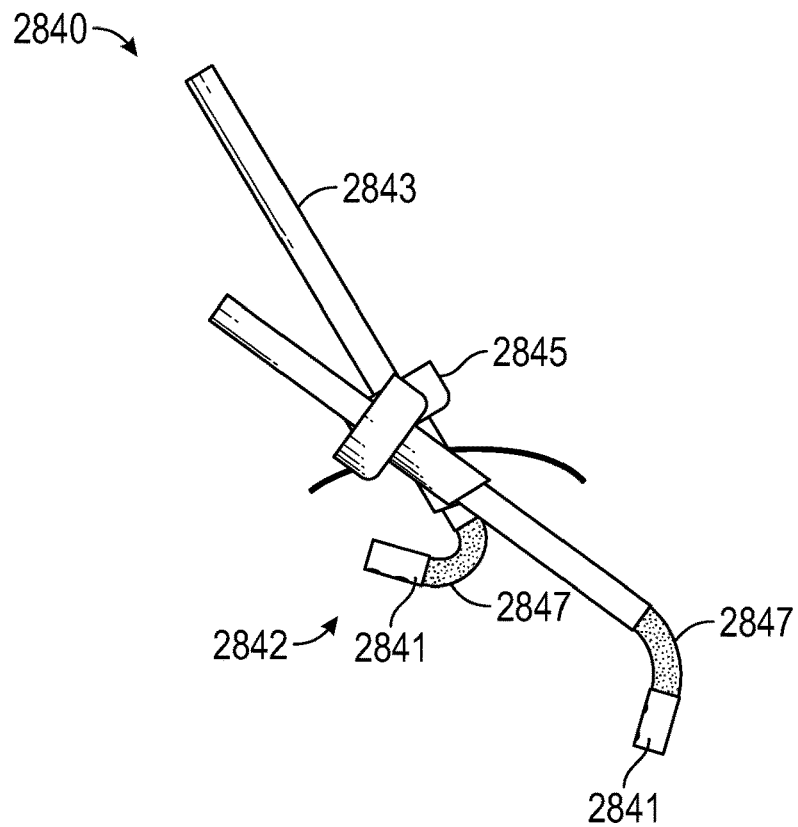

FIG. 28E illustrates yet another embodiment of a single articulation camera 2840. The single articulation camera 2840 includes a distal end 2841 coupled to a shaft 2843 via an articulating section 2847. The single articulation camera 2840 is configured to be docked to a cannula 2845, which may be rigid. The distal end 2841 may further include one or more imaging sensors 2842 located on a side of the distal end 2841. Similar to the embodiment of FIG. 28D, by utilizing the side-viewing imaging sensors 2842 which may be configured to provide a high-quality stereo image, the diameter of the distal end 2841 of the single articulation camera 2840 can be smaller than a 3D laparoscope of the related technology. The arrangement of the cannula 2845 and driving of the single articulation camera 2840 may also be performed in a manner similar to the embodiments discussed in connection with FIG. 28D.

Figure 28F:
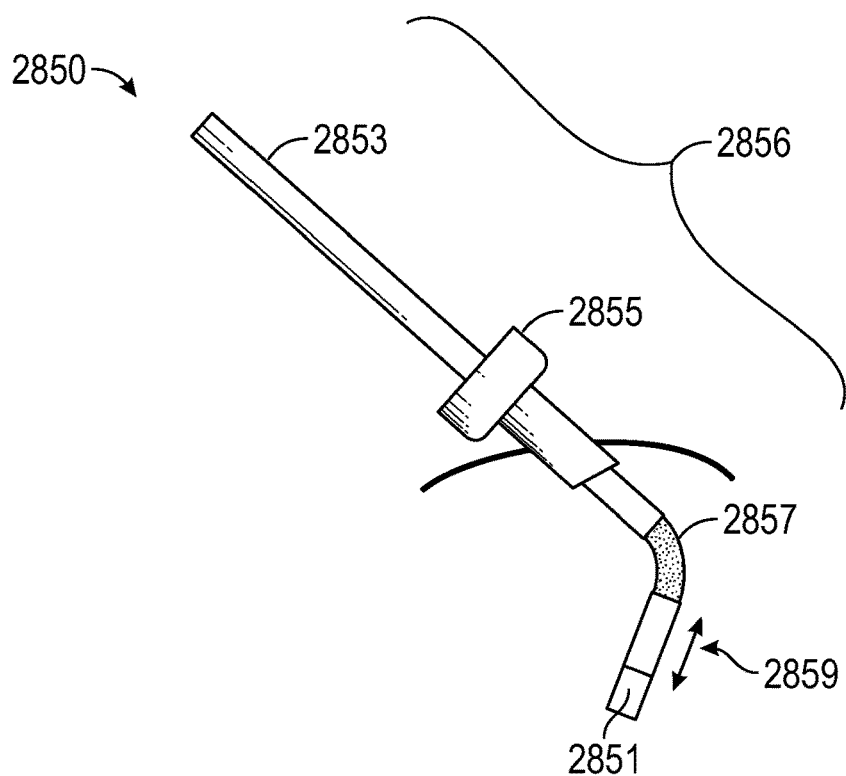

FIG. 28F illustrates another embodiment of an articulation camera 2850. The articulation camera 2850 includes a distal end 2851 coupled to a shaft 2853 via an articulating section 2857. The articulation camera 2850 is configured to be docked to a cannula 2855, which may be rigid. The articulation camera 2850 may further comprise a leader-shaft structure having an outer sheath 2856 formed by the shaft 2853 and the articulating section 2857 and an inner leader 2859 terminating at the distal end 2851. The sheath 2856 can be inserted through the cannula 2855 and articulated at the articulating section 2857. Once the sheath 2856 is parked, the leader 2859 can be independently driven to be inserted further into the patient from the distal end of the sheath 2856 which terminates past the articulating section 2857.

The placement of the cannula 2855 may be similar to the above-described embodiments. Since the FIG. 28F embodiment may not include a flexible cannula, the physician may only articulate the articulation camera 2850 once the entirety or at least a portion of the articulating section 2857 is distal to the cannula 2855. The robotic system may be configured to disable articulation until at least a portion of the articulating section 2857 is inserted past the cannula 2855. As described above, the system may automatically relax the articulation section 2857 if the articulation section 2857 is retracted into the cannula 2855 in an articulated state.

The driving of the articulation camera 2850 may be similar to the driving methods and modes discussed above in connection with FIGS. 28A-28E. In addition, the system may include an additional method for toggling between control of the leader 2859 and the sheath 2856. In leader control mode, the system may allow the physician to telescope the leader 2859 in and out of the sheath 2856. The system may further enable the physician to pan and tilt the camera located at the distal end 2851. The system may provide commands to pan and tilt of both the leader 2859 and the sheath 2856 to ensure safe movement between the two devices.

Figure 28G:
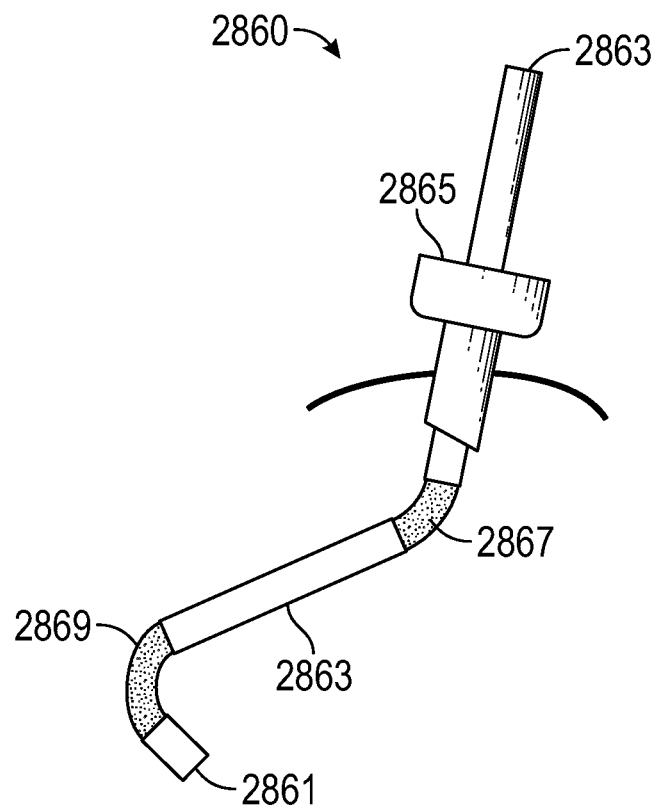

FIG. 28G illustrates an embodiment of a double articulation camera 2860. The double articulation camera 2860 includes a distal end 2861 coupled to a shaft 2863 via a first articulating section 2867 and a second articulating section 2869. The double articulation camera 2860 is configured to be docked to a cannula 2865, which may be rigid. The double articulation camera 2850 may be configured to be inserted through the cannula 2865 until each of the first and second articulating sections 2867 and 2869 are inserted past the cannula 2865. Each of the first and second articulating sections 2867 and 2869 can be articulated independently, allowing for greater DoF in repositioning the distal end 2861 of the double articulation camera 2860 compared to a single articulation embodiment.

The control mode and interface for the double articulation camera 2860 may be similar to the control techniques discussed above. In addition, the control interface may be configured to translate user input received from a user input interface (an example of which is provided below) to a 6-DoF distal end 2861 reference frame, which may provide the intended camera view to the physician. As will be discussed in greater detail below, the control techniques may generate a kinematic solution, so that the distal end 2861 including the camera moves to the referenced 6-DoF location. The double articulation embodiment may have at least two 2-DoF articulation sections 2867 and 2869 with the link lengths therebetween selected for optimization e.g., for providing a length capable of bending or articulation. The control mode in the double articulation camera 2860 embodiment may include redundancy resolution. For example, the double articulation camera 2860 may provide at least 2-DoF redundancy, which the system may use to select to achieve different optimization targets. For example, the redundancy may be used by the system to minimize the motion of the controlling robotic arms outside of the patient's body, while still providing increased range of motion to achieve multiple perspective views of a surgical site.

Figure 28H:
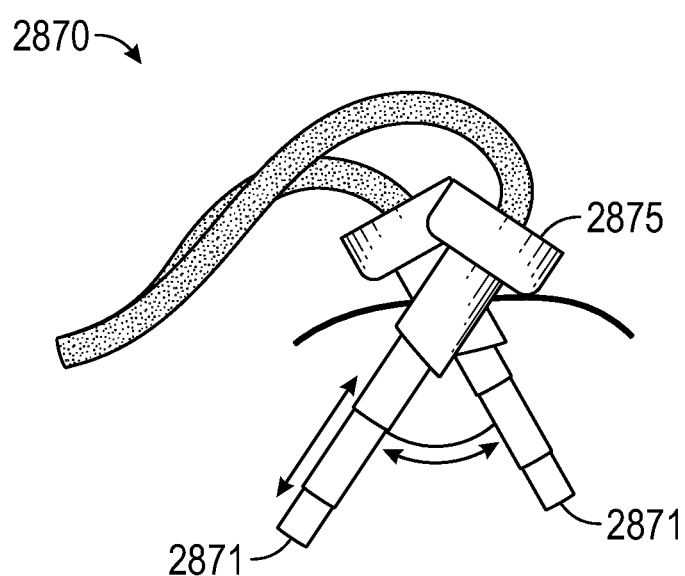

FIG. 28H illustrates an embodiment of a fully flexible camera 2870 that is configured to be docked to a motorized telescoping cannula 2875. The fully flexible camera 2870 includes a distal end 2871 which may be inserted through a cannula 275. The cannula 2875 in this FIG. 28H embodiment may be motorized to adjust the angle formed by the distal end 2871 of the fully flexible camera 2870 with respect to the patient. In addition to the angle adjustments provided by the motorized cannula 2875, the distal end 2871 of the fully flexible camera 2870 may have a telescoping section enabling the distal end 2871 to be inserted or retracted from the cannula 2875. In some embodiments, the telescoping section may be formed as a portion of the cannula 2875.

One advantage of the embodiment of FIG. 28H is that the motorized cannula can mimic the movements of a flexible laparoscope while effectively eliminating workspace requirements outside of the body. That is, the distal end 2871 of the fully flexible camera 2870 can be repositioned to obtain a desired view of a surgical site without requiring a spatial area for movement of a corresponding robotic arm. This can free up more space for the control of other surgical tools via the movement of corresponding robotic arms.

While a physician may use "camera hopping" to achieve multiple perspectives via either a rigid or articulatable scope, in some embodiments, the use of a repositionable and/or articulatable scope can enable multi-quadrant viewing without having to perform camera hopping. One advantage to the use of a repositionable and/or articulatable camera is that the camera can be inserted into a single cannula and can be angulated in multiple directions to obtain a triangulated view in one or more quadrants-all without having to move the scope into another port. This improves workflow since the undocking and redocking associated with camera hopping may involve a substantial interruption to the medical procedure. Any of the repositionable and/or articulatable cameras illustrated in the embodiments of FIGS. 28A-28H can be used to view multiple quadrants or perform "triangulation" in multiple quadrants. The location of the camera in achieving a given triangulated view may be referred to as a viewpoint of the camera.

In some embodiments, the system enables multi-perspective surgery which can include the ability to triangulate robotic laparoscopic instruments and a robotic laparoscope in all four quadrants of the abdomen, as well as the pelvis, with one set of five ports. This type of surgery can also be referred to as single-dock, multi-quadrant surgery. The placement of the ports for this embodiment is shown in FIG. 21, which is described above.

Using a repositionable and/or articulatable camera, such as one of embodiments described in connection with FIGS. 28A-28H, a physician can control the location and/or orientation of the camera to provide multiple perspective views of a surgical site, such as an abdominal region. As an example, a laparoscopic surgery can be performed in all four quadrants of the abdomen, as well as the pelvis, using one set of five ports (four instruments and one articulating camera) as shown in FIG. 21. Advantageously, each of the four robotic arms remain can docked to their respective cannulas 2105 labeled 1-4 during surgery in any of the quadrants. The bed (and thus the patient) may be tilted or angulated as desired to enable the multi-quadrant surgery as shown in FIGS. 23A-27E. One exemplary surgery is a colectomy, which involves the removal of part or all of a colon in all four quadrants and the pelvis. The four parts of the colon, not including the pelvic region, include the splenic flexure in the LUQ, the hepatic flexure in the RUQ, the cecum in the RLQ, and the Sigmund in the LLQ. The system described herein allows for surgery in each of these areas via an articulating camera.

Figure 29:
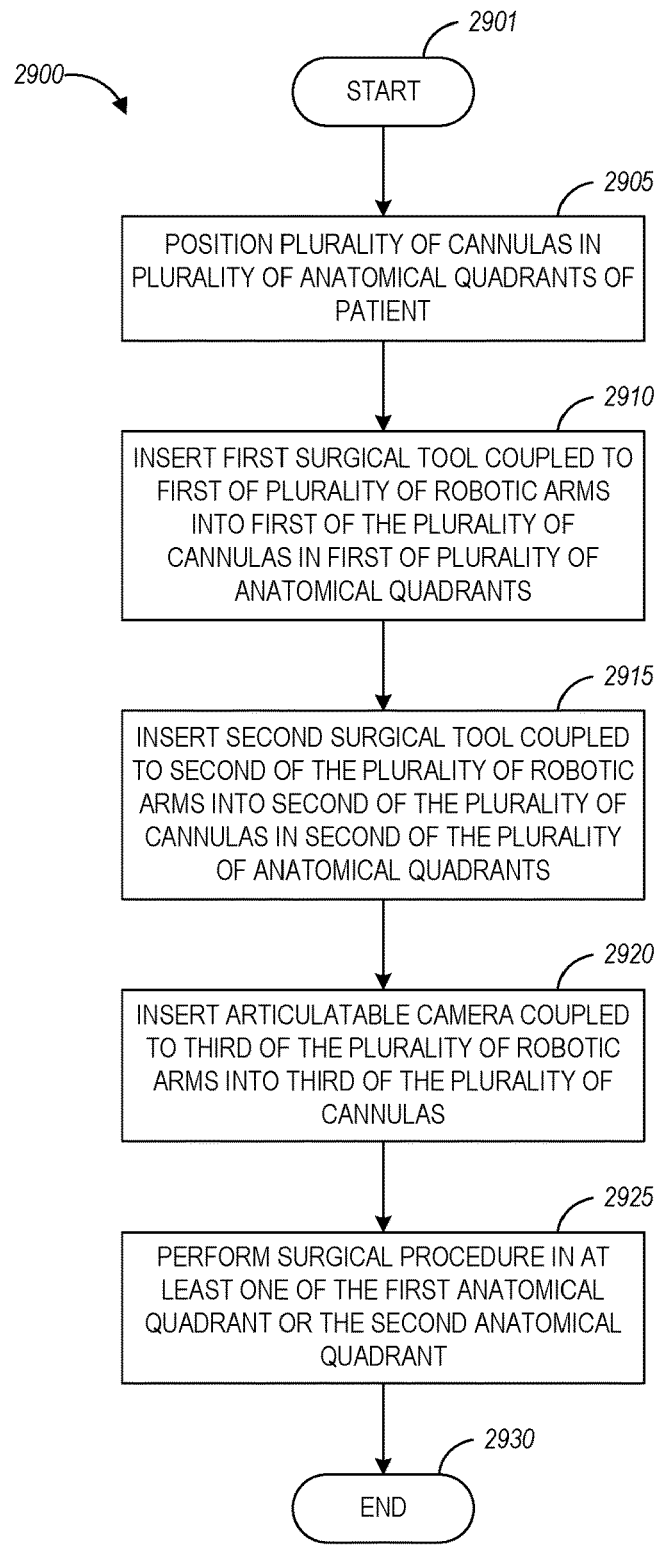
FIG. 29 is a flowchart illustrating an example method operable by a robotic system, or component(s) thereof, for obtaining multiple perspectives of a medical procedure in accordance with aspects of this disclosure.

FIG. 29 is a flowchart illustrating an example method operable by a robotic system, or component(s) thereof, for obtaining multiple perspectives of a medical procedure in accordance with aspects of this disclosure. For example, the steps of method 2900 illustrated in FIG. 29 may be performed by processor(s) and/or other component(s) of a medical robotic system (e.g., robotically-enabled system 10 or the surgical robotics system 1700) or associated system(s). For convenience, the method 2900 is described as performed by the "system" in connection with the description of the method 2900.

The method 2900 begins at block 2901. At block 2905, the method 2900 may involve positioning a plurality of cannulas in a plurality of anatomical quadrants of a patient. A first of the plurality of cannulas may be positioned in a first anatomical quadrant and a second of the plurality of cannulas may be positioned in a second anatomical quadrant. When performed in the example environment 2100 of FIG. 21, the cannulas 2105 labeled 1-4 may be positioned in each of the abdominal quadrants of the patient 2110 by a physician or an assistant. A cannula 2105 labeled C may also be placed on the positioned on the patient 1810 in a central location. Each of the plurality of cannulas 2105 may be capable of receiving therein at least one of a surgical tool or an articulatable camera. Thus, in certain embodiments, the plurality of cannulas comprises at least five cannulas, four of which are positioned in different anatomical quadrants from one another and one of which is placed at a central location relative to the four cannulas.

At block 2910, the method 2900 may involve the system inserting a first surgical tool coupled to a first of a plurality of robotic arms into the first of the plurality of cannulas in the first anatomical quadrant. At block 2915, the method 2900 may involve the system inserting a second surgical tool coupled to a second of the plurality of robotic arms into the second of the plurality of cannulas in the second anatomical quadrant.

At block 2920, the method 2900 may involve the system inserting an articulatable camera coupled to a third of the plurality of robotic arms into a third of the plurality of cannulas. The articulatable camera may be capable of showing a first view including the first surgical tool in the first anatomical quadrant and articulating to show a second view including the second surgical tool in the second anatomical quadrant.

At block 2925, the method 2900 may involve the system performing a surgical procedure in at least one of the first anatomical quadrant or the second anatomical quadrant. In certain embodiments, the surgical procedure may include the system receiving a selection of two of the robotic arms and performing, from the view of the camera, the surgical procedure with the two selected robotic arms. The surgical procedure may be performed based on user commands received from a master controller device (e.g., the controller 3002 of FIG. 30) comprising a first user input element and a second user input element. The first and the second input elements may be respectively mapped to control the selected robotic arms such that the system can control a first one of the two selected robotic arms based on first user commands received from the first user input element and control a second one of the two selected robotic arms based on second user commands received from the second user input element. The method 2900 ends at block 2930.

D. Multiple Perspective View Camera Interface and Control.

Figure 30:
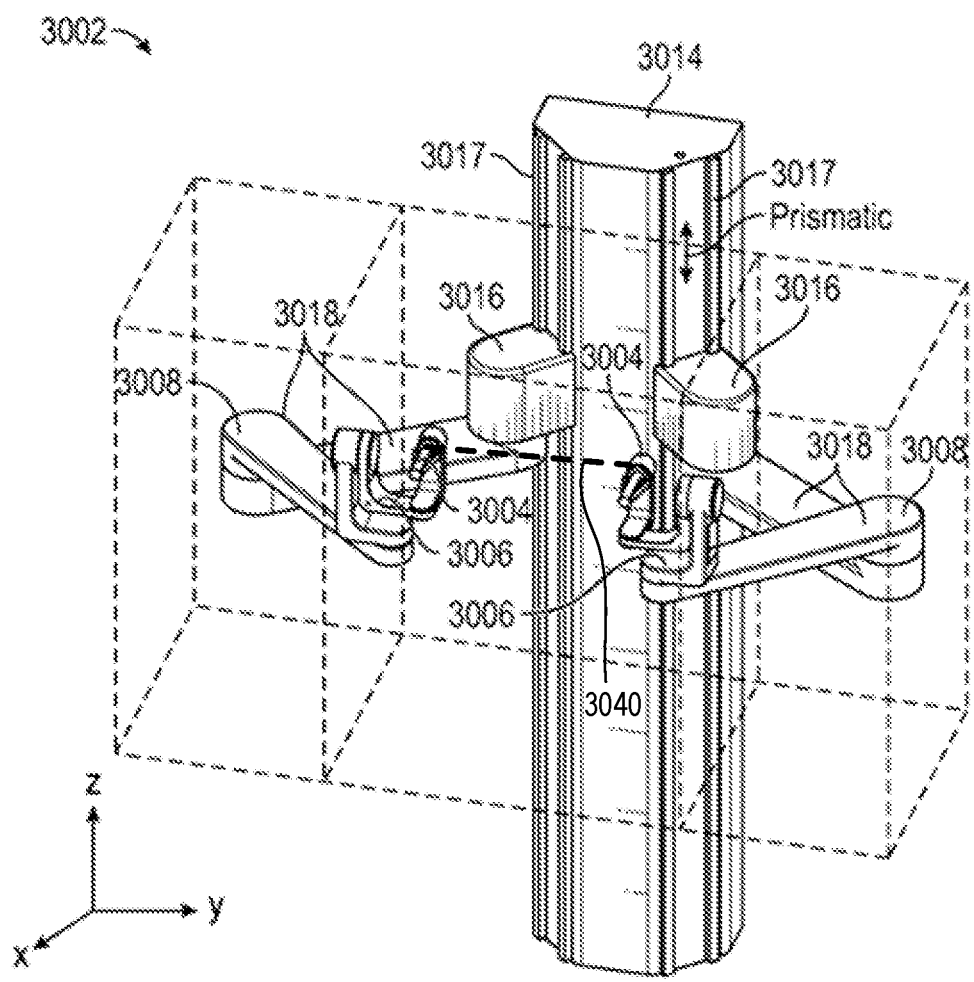
FIG. 30 is an example control interface which can control a repositionable and/or articulatable camera in accordance with aspects of this disclosure.

Certain aspects of this disclosure relate to a control interface configured to control a surgical robotic system to achieve multiple perspective views of a surgical site. FIG. 30 is an example control interface that can control a repositionable and/or articulatable camera in accordance with aspects of this disclosure. In particular, FIG. 30 provides a perspective view of an embodiment of a controller 3002. In the illustrated embodiment, the controller 3002 is configured to allow manipulation of one or more medical instruments. In the illustrated embodiment, the controller 3002 includes a pair handles 3004. In some embodiments, the pair of handles 3004 operate a single instrument, while in other embodiments, the pair of handles 3004 wherein each handle 3004 operates a different instrument. Each handle 3004 may be connected to a gimbal 3006. Each gimbal may be connected to a positioning platform 3008. In some embodiments, the handle 3004 is considered distal from the gimbal 3006, which is considered distal to the positioning platform 3008.

As shown in FIG. 30, in the illustrated embodiment, each positioning platform 3008 includes a selective compliance assembly robot arm (SCARA) arm 3018 having a plurality of links coupled to a column 3014 by a prismatic joint 3016. The prismatic joints 3016 are configured to translate along the column 3014 (e.g., along rails 3017) to allow the handle 3004 to be translated in the z-direction, providing a first degree of freedom. The SCARA arm 3018 may be configured to allow motion of the handle 3008 in an x-y plane, providing two additional DoF. Thus, each of the positioning platforms 3008 illustrated in FIG. 30 are configured to provide three degrees of positional or translational freedom and allow the operator to position the handles 3004 at any position (within reach of the positioning platform) in three dimensional (e.g., x, y, z) space. The SCARA 3018 arms may thus be configured to be manipulated by a user (e.g., via the handles 3004) and configured to generate controller output data. A further description of an example control interface which can be used to control a repositionable or articulatable camera is described in U.S. Provisional Patent Application No. 62/673,531, filed on May 18, 2018, the entirety of which is herein incorporated by reference.

Figure 31:
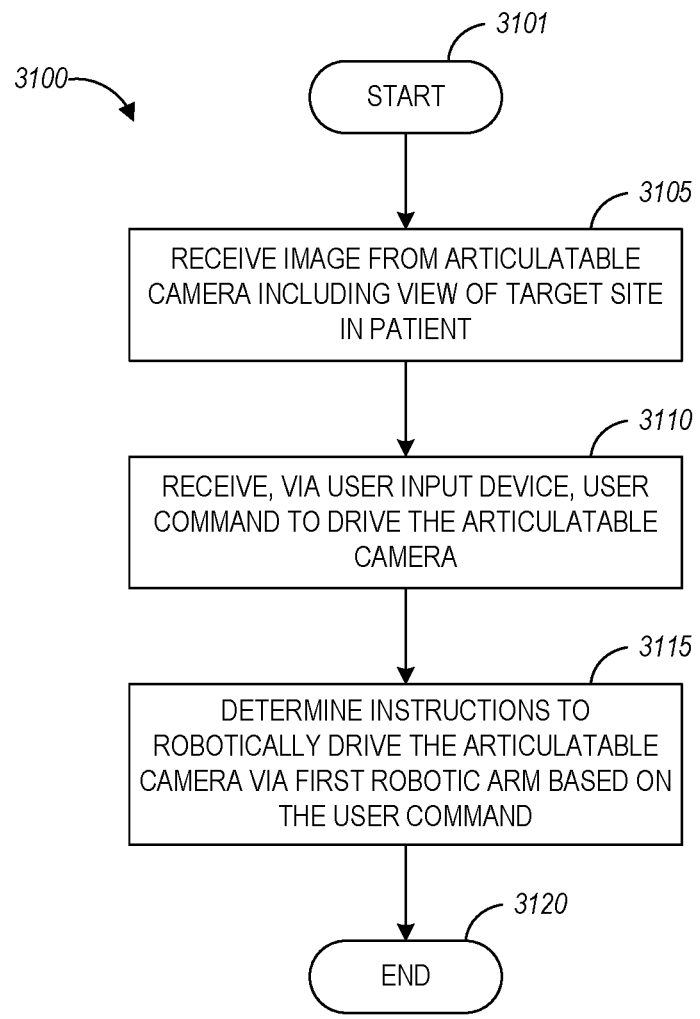
FIG. 31 is a flowchart illustrating an example method operable by a robotic system, or component(s) thereof, for driving an articulatable camera in accordance with aspects of this disclosure.

Using a control interface such as the controller 3002 of FIG. 30, the system may drive an articulatable camera to provide multiple perspective views of a surgical site. FIG. 31 is a flowchart illustrating an example method operable by a robotic system, or component(s) thereof, for driving an articulatable camera in accordance with aspects of this disclosure. For example, the steps of method 3100 illustrated in FIG. 31 may be performed by processor(s) and/or other component(s) of a medical robotic system (e.g., robotically-enabled system 10 or the surgical robotics system 1700) or associated system(s). For convenience, the method 3100 is described as performed by the "system" in connection with the description of the method 3100.

The method 3100 begins at block 3101. At block 3105, the system may receive an image from the articulatable camera including a view of a target site in the patient. Depending on the embodiment, the articulatable camera may have a viewing angle of greater than or equal to 180 degrees. At block 3110, the system may receive, via the user input device, a user command to drive the articulatable camera.

At block 3115, the system may determine instructions to robotically drive the articulatable camera via the first robotic arm based on the user command. The system may be configured to restrain at least one of the DoFs of the user input device so as to maintain orientation alignment between the first tool and the user input device during driving of the articulatable camera. Based on the driving and/or articulation motion of the camera, the articulatable camera may be capable of viewing an entire 4π spatial angle with a combination of articulation motion and field of view of the articulatable camera. In other embodiments, the articulatable camera may be capable of viewing greater than or equal 2π spatial angle with a combination of articulation motion and field of view of the articulatable camera. The method 3100 ends at block 3120.

Figure 32:
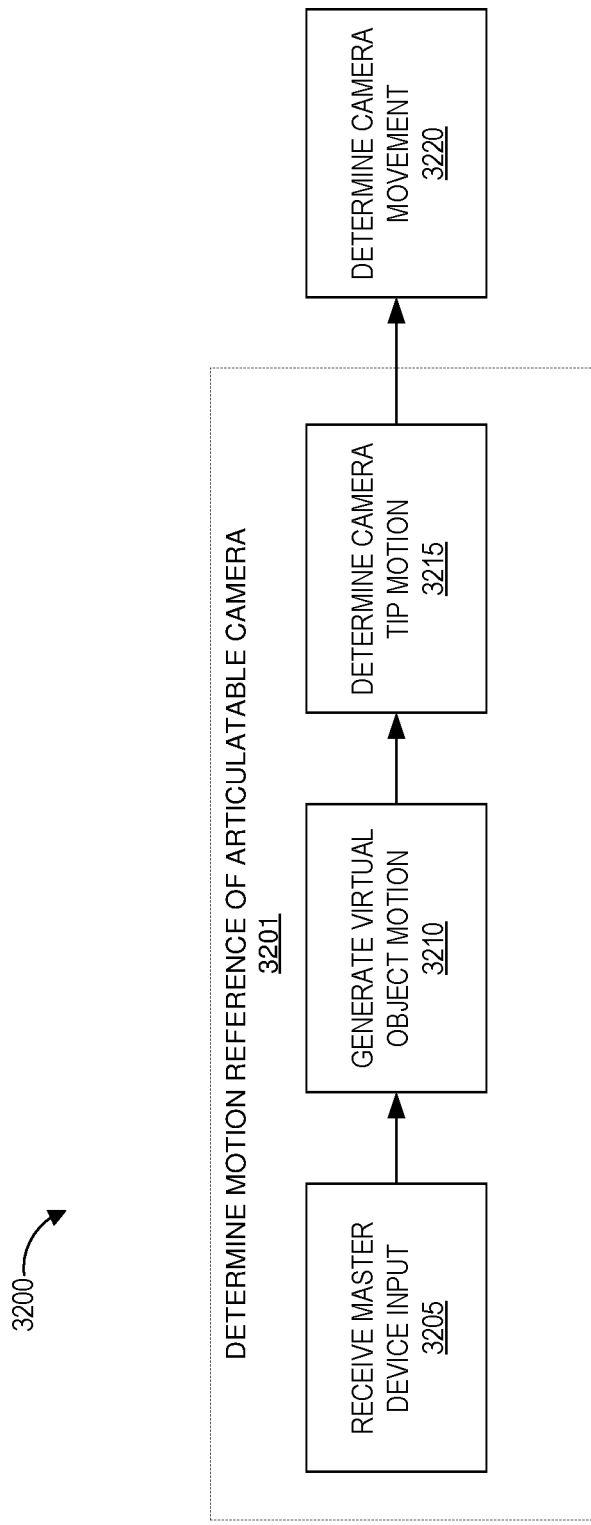
FIG. 32 is a block diagram which illustrates one exemplary method which can be used to translate user input commands received from a master device input and determine camera movement which may include robotic command data provided to drive the repositionable and/or articulatable camera in accordance with aspects of this disclosure.

The determination of the instructions by the system based on the user input may be logically divided into a number of different steps. FIG. 32 is a block diagram which illustrates one exemplary method 3200 which can be used to translate user input commands received from a master device input (e.g., the controller 3002 of FIG. 30) and determine camera movement which may include robotic command data provided to drive the repositionable and/or articulatable camera (hereinafter referred to as an articulatable camera in the context of FIG. 32 for ease of description).

As shown in FIG. 32, the method 3200 may involve at block 3201 the system determining a motion reference of the articulatable camera. The motion reference of the articulatable camera may include 6-DoF motion from a previous position to a current position based on the user commands. The 6-DoF motion may include a 3-DOF translation and a 3-DoF change in orientation for the camera tip. Using the motion reference, at block 3220 the system may determine the camera movement required to achieve the motion reference of the articulatable camera using inverse kinematics. The determined camera movement may include the robotic data commands required to achieve the commanded change in position from the user (e.g., the physician).

In certain embodiments, the master controller may include more than 6-DoF for the user input commands. For example, in the controller 3002 of FIG. 30, each of the handles 3004 may be configured to measure user input in 6-DOF (3-DOF of translation and 3-DOF of orientation). Thus, the total number of DoF measurable using both handles 3004 is 12-Dof. Since movement of the camera tip at block 3220 requires at most 6-DoF, the system may be able to use the additional DoF provided by the user input As discussed above, the user may be able to control the system via the controller 3002 in at least two different driving modes. The driving modes may include a first driving mode (also referred to as a first modality) for operating one or more of the surgical tools (e.g., a grasper and a cutter may be respectively driven using user commands received from the handles 3004) and a second driving mode (also referred to as a second modality) for repositioning the camera tip to obtain a different perspective view of the surgical site. In the first driving mode, the user commands received from the controller may be mapped to driving of surgical tool(s) and in the second driving mode, the user commands received from the controller may be mapped to driving of the articulatable camera via a corresponding robotic arm. Although not illustrated, the system may include an addition input device (e.g., a toggle switch) configured to allow the user to switch between the driving modes. Example embodiments of the toggle switch include a foot pedal, finger switch, etc.

In certain embodiments, when the user switched from the first diving mode (e.g., the surgical tool driving mode) to the second driving mode (e.g., the camera driving mode), the robot commands to the surgical tool tips may freeze with respect to the world coordinate frame (e.g., the pre-existing inertial reference frame as opposed to a moving camera frame).

While the user is in the camera driving mode, the system may display the view of the surgical site received from the camera. The displayed view may include the relative locations of the target anatomy, the surgical tool tips, and/or the camera tip.

Freezing the surgical tool tips within the world coordinate frame within the displayed view may take up 3-DoF of the total 12-DoF available from the controller 3002, thereby leaving up to 9 independent DoF which may be used for user input to control the camera in the camera driving mode. For example, the 3-DoF used to freeze the surgical tool tips may be used to constrain the orientation alignment of the surgical tool tips with the orientation of the controller 3002 such that the right-hand handle 3004 is mapped to the surgical tool located on the right side of the displayed view (and similarly the left-hand handle 3004 is mapped to the surgical tool located on the left side of the view). Without such a constraint, the location of the surgical tools within the display image may be reversed, increasing the cognitive load on the user to remember the mapping between the handles 3004 and the displayed locations of the surgical tools.

Figure 33A:
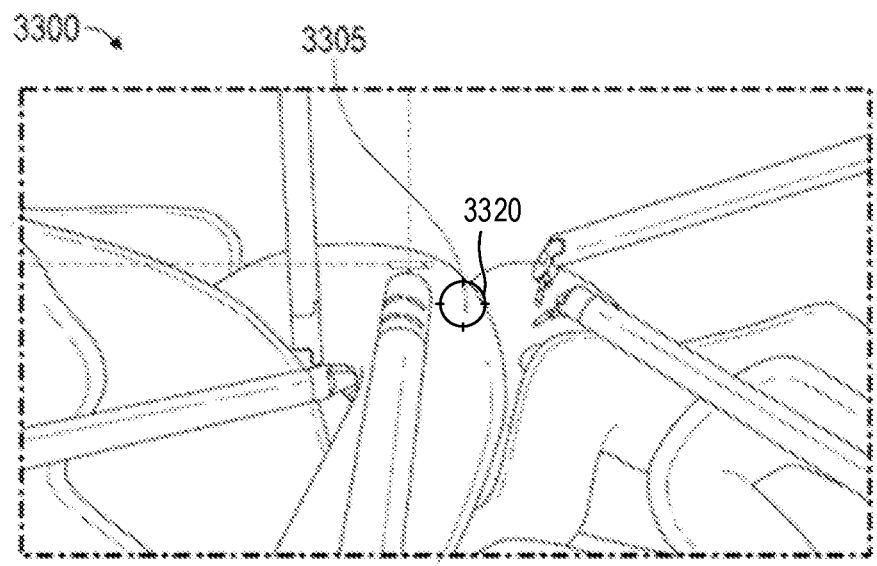
FIGS. 33A and 33B are views which may be provided by an articulating camera or generated as a virtual reconstruction showing an enhanced perspective of a focal point in accordance with aspects of this disclosure.

With continued reference to FIG. 32, block 3201 may include a number of sub-blocks. At block 3205, the system may receive master device input from the controller 3002. The master device input may include 12-DoF, 3-DoF of which are used to constrain the orientation of the surgical tool tips within the displayed camera view. In some embodiments, at block 3210 the system may use one or more of the remaining 9-DOF of the controller 3002 to generate virtual object motion in the camera view. The system may generate and display a virtual object within the camera view (e.g., the virtual object 3340 shown in FIG. 33A) to aid the user in driving the camera. The virtual object may refer to an object displayed within the camera view (e.g., the top perspective view 3300 of a splenic fixture 3305 shown in FIG. 33A) that provides a visual feedback hint to the user for driving the camera. The virtual object may align with a real object within the view, such as a portion of an anatomy within the view (e.g., as shown in FIG. 33A, the virtual object 3340 may align with the splenic fixture 3305 in the top perspective view 3300), or may be a completely virtual object created by the system to be overlaid on the displayed camera view, such as a focal point within the view. The user may "drive" movement of the virtual object within the camera view, which then may be used by the system to generate the robot data used to move the camera in block 3220. The master device input may thus be anchored to the coordinate frame of the camera view.

At block 3215, the system may determine the camera tip motion using the virtual object motion determined in block 3210. This may involve a transform of the virtual object motion from the camera coordinate frame into the world coordinate frame. Those skilled in the art will recognize that any technique which can suitable transform translation and orientation data between coordinate frames may be used to generate the camera tip motion based on the virtual object motion. As previously described, the system may determine the robot data representative of the camera movement in the world coordinate frame used to drive the camera based on the camera tip motion from block 3215.

There are a number of embodiments which can be used to map the master device input received in block 3205 into the virtual object motion determined in block 3210. For example, in one embodiment, the user may use one hand to control a single handle 3004 of the controller 3002 in 6-DOF of orientational and translational movement for the virtual object motion. In this embodiment, the relative translation of the handle 3004 may be mapped to the virtual object's translation in camera view and the relative orientation of the handle 3004 may be mapped to the virtual object's orientation. During the camera drive mode, the handle 3004 may be clutched off its matching slave tool tip for any translation, but the handle's 3004 orientation may be automatically aligned with the slave tool tip in the camera view without requiring any new DoF. The other handle's 3004 3-DoF orientation may be constrained to align with the corresponding slave tool tip's orientation under the changing camera view, while that 3-DOF translation can be either ignored or locked entirely. This embodiment may receive both rotation and translation input from user and may lack the capability to change amplification on orientation control of the camera, and thus, there may be a learning curve for the user to get used to the orientation control of camera view.

In another embodiment, the user may use two hands two manipulate two handles 3004 in 6-DoF by mapping position along a virtual bar 3040 connecting the two handles 3004 to the motion of the virtual object. That is, the 3-DOF common translations of the two handles' 3004 end-effectors may become the translation reference, and two of the 3-DoF differential translation may be used to calculate 2-DoF rotation of the virtual bar 3040 and the virtual object. The third differential translation along the bar may be either constrained for user to feel a rigid bar, or may not be used by the system. All of the 6-DoF for orientation of the two handles 3004 may be used to align to the corresponding tool tips' orientation under the changing camera view. In this way, the virtual object's motion reference may be within a 5D subspace, missing any rotation about the axis along the virtual bar 3040. However, the system may clutch to change the locations of the two arms' end-effectors. The system may realign the virtual bar 3040 to provide a different 5D subspace. Eventually, user could still explore the whole 6D workspace for camera control.

The virtual bar 3040 mapping may be more computationally complex than mapping a single handle to virtual object motion, but this embodiment may have the advantage of providing a better user experience since the driving of the virtual object in this fashion may provide a similar experience to a steering wheel or joystick. Further, in this embodiment, the system may use 6-DoF to maintain alignment of the surgical tool tips to the camera view, using all 12-DoF of the controller 3002.

In a modified version of the virtual bar mapping embodiment, the system may use only 5-DoF to maintain surgical tool alignment with the camera view. In this embodiment, the system may use the last DoF for camera control. In this embodiment, the common rotation of the two handles' 3004 end-effectors about the axis along the virtual bar 3040 may be used together with the two differential translations to form a rotational matrix reference, while the differential rotation along the axis may be constrained, for the need of orientation alignment of tool tips and for user to feel a rigid bar.

In another embodiment, the system may map 3-DoF translation from one of the handles 3004 to the translation of virtual object and map 3-DoF translation from the other handle 3004 to the orientation of the virtual object. All the 6-DoF orientation of the two arms may then be used to align to the corresponding tool tips' orientation under the changing camera view. From translation to orientation mapping, a scale can be introduced to convert each translation to a Euler angle value for the synthesis of the rotational matrix. In this way, the user can set a preferred amplification for camera control, not only on translation but also independently on orientation.

In a modification of the above embodiment, the system may enable translation and orientation control of the virtual object in tandem, e.g., by switching between translation and orientation control sub-modes via a user pedal input, which can let user focus on one type of motion at a time. The system may maintain the center of rotation during orientation control, and the camera tip's rotation induced translation can thus be minimized. This embodiment may potentially reduce complexity in user input and unintentional motion on camera tip.

Embodiment of this disclosure provide for the use of a robotically controlled articulatable camera to obtain enhanced perspective view(s) of a surgical target, surgical site or general focal point. Robotic systems of the related technology may be capable of viewing a focal point from a limited number of perspectives. For example, certain robotic systems may be able to view a front side of a focal point, but may not be able to view the sides or back of the focal point. In enhanced perspective surgery, the systems can provide surgical views and maneuvers about an anatomy, in a single or multiple quadrants.

Figure 33B:
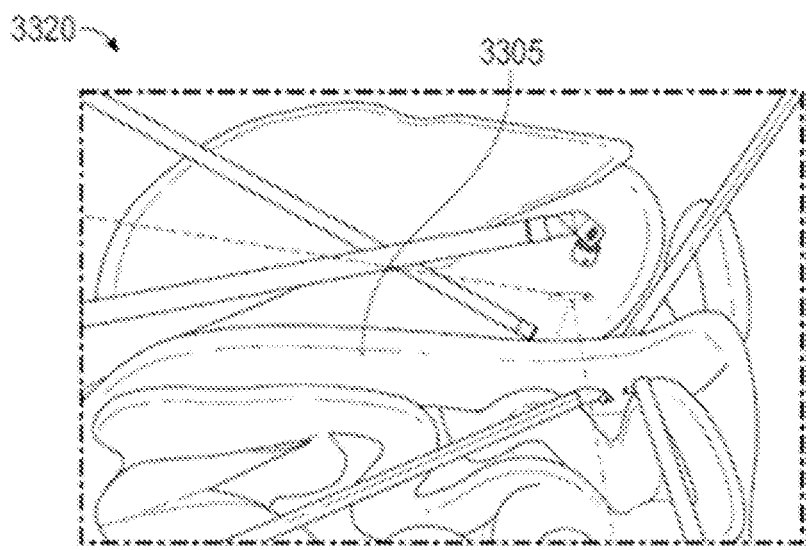

Using one or more of the articulatable cameras described herein, a physician can view a surgical target, surgical site, or focal point from multiple perspectives, including front, back and side views. In some embodiments, the articulating camera is capable of articulating potentially up to 360 degrees around the focal point. In some embodiments, the articulating camera is capable of articulating 180 degrees around the focal point. In some embodiments, the articulating camera can move and up and down so as to achieve various top and bottom views from different perspectives. In some embodiments, the articulatable camera is capable of viewing an entire $4\pi$ spatial angle with a combination of articulation motion and field of view of the articulatable camera. In some embodiments, the articulatable camera is capable of viewing greater than or equal $2\pi$ spatial angle with a combination of articulation motion and field of view of the articulatable camera. In some embodiments, the view comprises at least one of: a front view, a side view, and a back view of the target site. FIGS. 33A and 33B are views which may be provided by an articulating camera or generated as a virtual reconstruction showing an enhanced perspective of a focal point in accordance with aspects of this disclosure.

FIG. 33A provides a top perspective view 3300 of a splenic fixture 3305 (e.g., relative to the virtual object 3340). In the view 3320 of FIG. 33B, the articulating camera has been articulated such that a side view of the splenic fixture 3305 is more visible. Each of the top perspective view 3300 and the side view 3320 may be provided by a scope/camera according to one of the embodiments of this disclosure, a gods-eye view sensor located in one or more of the cannulas, and/or a virtual reconstruction representative of the location of the patient's anatomy, surgical tools, and the camera. In other embodiments, the camera can articulate such that an enhanced perspective view can be provided, whereby a top, bottom or sides of a focal point can be viewed. Further, in other embodiments, the views 3300 and 3320 may correspond to gods-eye views provided by an imaging sensor located in one or more of the cannulas placed in the patient or may be a virtual reconstruction generated by the system based on kinematic information used for robot control a patient model.

3. Implementing Systems and Terminology.

Implementations disclosed herein provide systems, methods and apparatuses for providing multiple perspectives during medical procedures.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number of corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A system, comprising:
a first robotic arm configured to be coupled to a first cannula positioned in a first anatomical location of a patient and drive an articulatable camera, the articulatable camera configured to be driven in a first number of degrees-of-freedom (DoFs);
a second robotic arm configured to be coupled to a second cannula positioned in a second anatomical location of the patient and drive a first tool;
a user input device configured to be manipulated by a user in a second number of DoFs;
one or more processors; and
memory storing computer-executable instructions to cause the one or more processors to:
receive an image from the articulatable camera including a view of a target site in the patient,
receive, via the user input device, a user command to drive the articulatable camera, and
determine instructions to robotically drive the articulatable camera via the first robotic arm based on the user command, wherein at least one of the DoFs of the user input device is constrained so as to maintain orientation alignment between the first tool and the user input device,
wherein, upon the user command to drive the articulatable camera, movement of a first handle of the user input device is mapped to translation and orientation of the articulatable camera, and the movement of the first handle is aligned with orientation of the first tool while being clutched off translation of the first tool.

2. The system of claim 1, wherein:
wherein the memory further has stored thereon computer-executable instructions to cause the one or more processors to toggle between a first modality in which motion of the user input device is mapped to driving of the first tool via the second robotic arm and a second modality in which motion of the user input device is mapped to driving of the articulatable camera via the first robotic arm.

3. The system of claim 1, wherein the user input device comprises a pair of input arms configured to be manipulated by the user and generate master controller output data.

4. The system of claim 3, wherein the memory further has stored thereon computer-executable instructions to cause the one or more processors to:
display a virtual object within the view received from the articulatable camera, the virtual object aligning with an object in the view.

5. The system of claim 4, wherein the memory further has stored thereon computer-executable instructions to cause the one or more processors to:
constrain differential translation between the pair of input arms to simulate a virtual bar connecting the pair of input arms as a rigid bar.

6. The system of claim 1, further comprising:
a third robotic arm configured to be connected to a third cannula positioned in a third anatomical location of the patient and drive a second tool,
wherein to determine the instructions to drive the articulatable camera via the first robotic arm, the computer-executable instructions further cause the one or more processors to maintain a relative orientation of the first tool and the second tool within the view of the articulatable camera by constraining one or more of the DoFs of the user input device.

7. The system of claim 1, wherein the memory further has stored thereon computer-executable instructions to cause the one or more processors to:
display a virtual object within the view received from the articulatable camera, wherein the virtual object is overlaid on the view, and wherein the user command includes a user command to drive motion of the virtual object within the view.

8. The system of claim 1, wherein the second number of DoFs are greater than or equal to the first number of DoFs.

9. The system of claim 1, wherein in a plane, the articulatable camera has a viewing angle of greater than or equal to 180 degrees.

10. The system of claim 1, wherein the articulatable camera is configured to view a $4\pi$ spatial angle with a combination of articulation motion and field of view of the articulatable camera.

11. The system of claim 1, wherein the articulatable camera is configured to view greater than or equal to a $2\pi$ spatial angle with a combination of articulation motion and field of view of the articulatable camera.

12. The system of claim 1, wherein the view comprises at least one of: a front view, a side view, and a back view of the target site.

13. A surgical method, comprising:
receiving an image from an articulatable camera including a view of a target site in a patient, the articulatable camera configured to be driven in a first number of degrees-of-freedom (DoFs) via a first robotic arm configured to be coupled to a first cannula positioned in a first anatomical location of the patient;
receiving, via a user input device, a user command to drive the articulatable camera, the user input device configured to be manipulated by a user in a second number of DoFs; and
determining instructions to robotically drive the articulatable camera via the first robotic arm based on the user command, wherein at least one of the DoFs of the user input device is constrained so as to maintain orientation alignment between the user input device and a first tool configured to be driven via a second robotic arm configured to be coupled to a second cannula positioned in a second anatomical location of the patient,
wherein, upon the user command to drive the articulatable camera, movement of a first handle of the user input device is mapped to translation and orientation of the articulatable camera, and the movement of the first handle is aligned with orientation of the first tool while being clutched off translation of the first tool.

14. The method of claim 13, wherein the method further comprises:
toggling between a first modality in which motion of the user input device is mapped to driving of the first tool via the second robotic arm and a second modality in which motion of the user input device is mapped to driving of the articulatable camera via the first robotic arm.

15. The method of claim 13, wherein the user input device comprises a pair of input arms configured to be manipulated by the user and generate master controller output data.

16. The method of claim 15, further comprising:
displaying a virtual object within the view received from the articulatable camera, the virtual object aligning with an object in the view.

17. The method of claim 13, wherein:
determining the instructions to drive the articulatable camera via the first robotic arm comprises maintaining a relative orientation of the first tool and a second tool within the view of the articulatable camera by constraining one or more of the DoFs of the user input device, and
the second tool is configured to be driven by a third robotic arm configured to be connected to a third cannula positioned in a third anatomical location of the patient.

18. The method of claim 13, further comprising:
displaying a virtual object within the view received from the articulatable camera, a position of the virtual object being based on the user command to drive the articulatable camera, wherein the user command includes a user command to drive motion of the virtual object within the view.

19. A system, comprising:
a first robotic arm configured to drive an articulatable camera, the articulatable camera configured to be driven in a first number of degrees-of-freedom (DoFs);
a second robotic arm configured to drive a first tool;
a user input device configured to be manipulated by a user in a second number of DoFs, wherein the user input device comprises a pair of handles, the pair of handles comprising a first handle and a second handle;
one or more processors; and
memory storing computer-executable instructions to cause the one or more processors to:
receive an image from the articulatable camera including a view of a portion of an anatomy of a patient,
receive, via the user input device, a user command to drive the articulatable camera, and
robotically drive the articulatable camera via the first robotic arm based on the user command, wherein at least one of the DoFs of the user input device is constrained to maintain orientation alignment between the first tool and the user input device, and wherein the articulatable camera is driven from a first quadrant of the patient to a second quadrant of the patient without undocking the first robotic arm from a cannula placed in the patient,
wherein, upon the user command to drive the articulatable camera, movement of the first handle is mapped to translation and orientation of the articulatable camera, and the movement of the first handle is aligned with orientation of the first tool while being clutched off translation of the first tool.

* * * * *